(12) United States Patent
Chen et al.

(10) Patent No.: US 9,195,796 B2
(45) Date of Patent: Nov. 24, 2015

(54) MALIGNANCY-RISK SIGNATURE FROM HISTOLOGICALLY NORMAL BREAST TISSUE

(75) Inventors: Dung-Tsa Chen, Tampa, FL (US); Timothy J. Yeatman, Thonotosassa, FL (US)

(73) Assignees: H. Lee Moffitt Cancer Center and Research Institute, Inc., Tampa, FL (US); University of South Florida, Tampa, FL (US)

( * ) Notice: Subject to any disclaimer, the term of this patent is extended or adjusted under 35 U.S.C. 154(b) by 157 days.

(21) Appl. No.: 12/812,215

(22) PCT Filed: Jan. 12, 2009

(86) PCT No.: PCT/US2009/030778
§ 371 (c)(1),
(2), (4) Date: Oct. 29, 2010

(87) PCT Pub. No.: WO2009/089548
PCT Pub. Date: Jul. 16, 2009

(65) Prior Publication Data
US 2011/0039723 A1 Feb. 17, 2011

Related U.S. Application Data

(60) Provisional application No. 61/020,575, filed on Jan. 11, 2008.

(51) Int. Cl.
C12Q 1/68 (2006.01)
G06F 19/20 (2011.01)

(52) U.S. Cl.
CPC .............. *G06F 19/20* (2013.01); *C12Q 1/6886* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

2004/0018525 A1* 1/2004 Wirtz et al. ............... 435/6

OTHER PUBLICATIONS

Ma et al. PNAS. 2003. 100(10): 5974-5979.*
Gur-Dedeoglu. BMC Cancer. 2008. 8: 396.*
Chan. G&P. magazine. 2006. 6(3): 20-26.*
Hoshikawa et al. Physical Genomics. 2003. 12: 209-219.*
Finak. Breast Cancer Research 2006 8:R58.*
Ellsworth. The Lancet Oncol 2004; 5: 753-58.*
Bair E, Tibshirani R (2004) Semi-supervised methods to predict patient survival from gene expression data. PLoS Biol 2(4):E108. doi:10.1371/journal.pbio.002010.

(Continued)

*Primary Examiner* — Dave Nguyen
*Assistant Examiner* — Joseph G Dauner
(74) *Attorney, Agent, or Firm* — Meunier Carlin & Curfman LLC

(57) ABSTRACT

The invention provides for malignancy-risk gene signatures that predict the risk of developing breast cancer, the recurrence of breast cancer, and/or the metastasis of breast cancer. These signatures have numerous clinical applications including assessing risk of breast cancer development following routine breast biopsy, assessing the need for adjuvant radiotherapy after lumpectomy, and determining the need for completion mastectomy following lumpectomy for the breast cancer patient and other treatment plans that are personalized for the patient.

22 Claims, 54 Drawing Sheets

(56) References Cited

OTHER PUBLICATIONS

Berry DA, Cronin KA, Plevritis SK, Fryback DG, Clarke L, Zelen M et al (2005) Effect of screening and adjuvant therapy onmortality from breast cancer. N Engl J Med 353(17):1784-1792. doi:10.1056/NEJMoa050518.

Botti C, Pescatore B, Mottolese M, Sciarretta F, Greco C, Di Filippo F, et al (2000) Incidence of chromosomes 1 and 17 aneusomy in breast cancer and adjacent tissue: an interphase cytogenetic study. J Am Coll Surg 190(5):530-539. doi: 10.1016/S1072-7515(00)00252-0.

Breiman L., Friedman, J., Olshen, R & Stone, C. Classification and Regression Trees, (Wadsworth & Brooks, Monterey, CA, 1984).

Carter SL, Eklund AC, Kohane IS, Harris LN, Szallasi Z (2006) A signature of chromosomal instability inferred from gene expression profiles predicts clinical outcome in multiple human cancers. Nat Genet 38(9):1043-1048. doi:10.1038/ng1861.

Change HY, Nuyten DS, Sneddon JB, Hastie T, Tibshirani R, Sorlie T et al (2005) Robustness, scalability, and integration of a wound-response gene expression signature in predicting breast cancer survival. Proc Natl Acad Sci USA 102(10):3738-3743. doi:10.1073/pnas.0409462102.

Chanrion M, Negre V, Fontaine H, Salvetat N, Bibeau F, Mac Grogan G et al (2008) A gene expression signature that can predict the recurrence of tamoxifen-treated primary breast cancer. Clin Cancer Res 14(6):1744-1752. doi:10.1158/1078-0432.CCR-07-1833.

Chen D-T, Nasir A, Culhane A, Venkataramu C, Fulp W, Rubio R et al (2009) Proliferative genes dominate malignancy-risk signature in histologically normal breast tissue. Breast Cancer Res Treat. doi:10.1007/s10549-009-0344-y, p. 335-346.

Chung CH, Bernard PS, Perou CM (2002) Molecular portraits and the family tree of cancer. Nat Genet 32(Suppl):533-540. doi:10.1038/ng1038.

Deng GR, Lu Y, Zlotnikov G, Thor AD, Smith HS (1996) Loss of heterozygosity in normal tissue adjacent to breast carcinomas. Science 274(5295):2057-2059. doi:10.1126/science.274.5295.2057.

Ellsworth DL, Ellsworth RE, Love B, Deyarmin B, Lubert SM, Mittal V et al (2004) Outer breast quadrants demonstrate increased levels of genomic instability. Ann Surg Oncol 11(9):861-868. doi:10.1245/ASO.2004.03.024.

Finak G, Bertos N, Pepin F, Sadekova S, Souleimanova M, Zhao H et al (2008) Stromal gene expression predicts clinical outcome in breast cancer. Nat Med 14(5):518-527. doi:10.1038/nm1764.

Fisher, B., et al. Ten-year results of a reandomized clinical trial comparing radical mastectomy and total mastectomy with or without radiation. New England Journal of Medicine 312, 674-681 (1985).

Fitzgibbons PL, De Henson, Hutter RV (1998) Benign breast changes and the risk for subsequent breast cancer: an update of the 1985 consensus statement. Cancer Committee of the College of American Pathologists. Arch Pathol Lab Med 122(12):1053-1055.

Fredriksson I, Liljegren G, Palm-Sjovall M, Arnesson LG, Emdin SO, Fornander T et al (2003) Risk factors for local recurrence after breast-conserving surgery. Br J Surg 90(9):1093-1102. doi: 10.1002/bjs.4206.

Giordano SH, Buzdar AU, Smith TL, Kau SW, Yang Y, Hortobagyi GN (2004) Is breast cancer survival improving? Cancer 100(1):44-52. doi:10.1002/cncr.11859.

Glas AM, Floore A, Delahaye LJ, Witteveen AT, Pover RC, Bakx N et al (2006) Converting a breast cancer microarry signature into a high-throughput diagnostic test. BMC Genomics 7:278. doi:10.1186/1471-2164-7-278.

Hartigan JA, W.M. A K—Means Clustering Algorithm. Applied Statistics 28, 100-108 (1979).

Huang E, Cheng SH, Dressman H, Pittman J, Tsou MH, Horng CF et al (2003) Gene expression predictors of breast cancer outcomes. Lancet 361(9369):1590-1596. doi:10.1016/S0140-6736(03)13308-9.

Irizarry RA, Bolstad BM, Collin F, Cope LM, Hobbs B, Speed TP (2003) Summaries of Affymetrix GeneChip probe level data. Nucleic Acids Res 31(4):e15.

Kaplan, J., et al. Breast conservation in patients with multiple ipsilateral synchronous cancers. Journal of the American College of Surgeons 197, 726-729 (2003).

Larson PS, De Las Morenas A, Bennett SR, Cupples LA, Rosenberg CL (2002) Loss of heterozygosity or allele imbalance in histologically normal breast epithelium is distinct from loss of heterozygosity or allele imbalance in co-existing carcinomas. Am J Pathol 161(1):283-290.

Lewis CM, Cler LR, Bu DW, Zochbauer-Muller S, Milchgrub S, Naftalis EZ et al (2005) Promoter hypermethylation in benign breast epithelium in relation to predicted breast cancer risk. Clin Cancer Res 11(1):166-172.

Li Z, Moore DH, Meng ZH, Ljung BM, Gray JW, Dairkee SH (2002) Increased risk of local recurrence is associated with allelic loss in normal lobules of breast cancer patients. Cancer Res 62(4):1000-1003.

Ma XJ, Salunga R, Tuggle JT, Gaudet J, Enright E, Mcquary P et al (2003) Gene expression profiles of human breast cancer progression. Proc Natl Acad Sci USA 100(10):5974-5979. doi: 10.1073/pnas.0931261100.

Miller RG (1981) Simultaneous statistical inference, 2nd edn. Springer-Verlag, New York, NY.

Page, D.L., Dupont, W.D., Rogers, L.W., Jensen, R.A. & Schuyler, P.A. Continued local recurrence of carcinoma 15-25 years after a diagnosis of low-grade ductal carcinoma in-situ of the breast treated only by biospsy. Cancer 76,1197-1200 (1995).

Paik S, Shak S, Tang G, Kim C, Baker J, Cronin M et al (2004) A multigene assay to predict recurrence of tamoxifen-treated, nodenegative breast cancer. N Engl J Med 351(27):2817-2826. doi: 10.1056/NEJMoa041588.

Perou CM, Sorlie T, Eisen MB, Van De Rijn M, Jeffrey SS, Rees CA et al (2000) Molecular portraits of human breast tumours. Nature 406(6797):747-752. doi: 10.1038/35021093.

Poola I, Dewitty RL, Marshalleck JJ, Bhatnagar R, Abraham J, Leffall LD (2005) Identification of MMP-1 as a putative breast cancer predictive marker by global gene expression analysis. Nat Med 11(5):481-483. doi:10.1038/nm1243.

Price, P., et al. Duct carcinoma insitu: predictors of local recurrence and progreassion in patients treated by surgery alone. British Journal of Cancer 61, 869-872 (1990).

Robbins P, Pinder S, Deklerk N, Dawkins H, Harvey J, Sterrett G et al (1995) Histological grading of breast carcinomas—a study of interobserver agreement. Hum Pathol 26(8):873-879. doi: 10.1016/0046-8177(95)90010-1.

Rosenwald A, Wright G, Wiestner A, Chan WC, Connors JM, Campo E et al (2003) The proliferation gene expression signature is a quantitative integrator of oncogenic events that predicts survival in mantle cell lymphoma. Cancer Cell 3(2):185-197. doi:10.1016/S1535-6108(03)00028-X.

Schnitt SJ, Morrow M (1999) Lobular carcinoma in situ: current concepts and controversies. Semin Diagn Pathol 16(3):209-223.

Shah VI, Raju U, Chitale D, Deshpande V, Gregory N, Strand V (2003) False-negative core needle biopsies of the breast—an analysis of clinical, radiologic, and pathologic findings in 27 consecutive cases of missed breast cancer. Cancer 97(8):1824-1831. doi:10.10021cncr.11278.

Sorlie T, Perou CM, Tibshirani R, Aas T, Geisler S, Johnsen H et al (2001) Gene expression patterns of breast carcinomas distinguish tumor subclasses with clinical implications. Proc Natl Acad Sci USA 98(19):10869-10874. doi:10.1073/pnas.19136709.

Tripathi A, King C, De La Morenas A, Perry VK, Burke B, Antoine GA et al (2008) Gene expression abnormalities in histologically normal breast epithelium of breast cancer patients. Int J Cancer 122(7):1557-1566. doi:10.1002/ijc.23267.

Turashvili G, Bouchal J, Baumforth K, Wei W, Dziechciarkova M, Ehrmann J, Klein J, Fridman E, Skarda J, Srovnal J, Hajduch M, Murray P, Kolar Z (2007) Novel markers for differentiation of lobular and ductal invasive breast carcinomas by laser microdissection and microarray analysis. BMC Cancer 7:55.

(56) References Cited

OTHER PUBLICATIONS

Tusher VG, Tibshirani R, Chu G (2001) Significance analysis of microarrays applied to the ionizing radiation response. Proc Natl Acad Sci USA 98(9):5116-5121. doi:10.1073/pnas.091062498.

Tuttle, T.M., Habermann, E., Grund, E., Morris, T. & Virnig, B. Increasing use of contralateral prophylactic mastectomy among breast cancer patients: a trend toward more aggressive surgical treatment. Journal of Clinical Oncology 25(33):5203-5209 (2007).

Van De Vijver MJ, He YD, Van't Veer LJ, Dai H, Hart AAM, Voskuil DW et al (2002) A gene-expression signature as a predictor of survival in breast cancer. N Engl J Med 347(25):1999-2009. doi:10.1056/NEJMoa021967.

Wang Y, Klijn JG, Zhang Y, Sieuwerts AM, Look MP, Yang F et al (2005) Gene-expression profiles to predict distant metastasis of lymph-node-negative primary breast cancer. Lancet 365(9460): 671-679.

Wapnir I, Anderson SEM, Mamounas E et al (2005) Survival after IBTR in NSABP Node Negative Protocols B-13, B-14, B-19, B-20 and B-23. J Clin Oncol 23:8s (suppl; abstr 517).

Wapnir IL, Anderson SJ, Mamounas EP, Geyer CE Jr, Jeong JH, Tan-Chiu E et al (2006) Prognosis after ipsilateral breast tumor recurrence and locoregional recurrences in five National Surgical Adjuvant Breast and Bowel Project node-positive adjuvant breast cancer trials. J Clin Oncol 24(13):2028-2037. doi:10.1200/JCO.2005.04.3273.

Whitfield ML, George LK, Grant GD, Perou CM (2006) Common markers of proliferation. Nat Rev Cancer 6(2):99-106. doi: 10.1038/nrc 1802.

Whitfield ML, Sherlock G, Saldanha AJ, Murray JI, Ball CA, Alexander KE et al (2002) Identification of genes periodically expressed in the human cell cycle and their expression in tumors. Mol Biol Cell 13(6):1977-2000. doi:10.1091/mbc.02-02-0030.

\* cited by examiner

| Cell adhesion | | | | |
|---|---|---|---|---|
| Map | Cell process | p-Value | Number of Genes in IDC gene signature | Total Number of Genes |
| * ECM remodeling | cell adhesion | 1.62E-07 | 17 | 60 |
| * Keratin filaments | cell adhesion | 8.06E-06 | 13 | 48 |
| * Plasmin signaling | cell adhesion | 1.70E-04 | 11 | 47 |
| * Cytoskeleton remodeling | cell adhesion | 4.69E-04 | 24 | 176 |
| * Chemokines and adhesion | cytokine and chemokine mediated signaling pathway, cell adhesion | 3.96E-04 | 24 | 174 |
| * Integrin outside-in signaling | cell adhesion | 1.69E-03 | 13 | 79 |
| * Role of tetraspanins in the integrin-mediated cell adhesion | cell adhesion | 3.04E-03 | 10 | 56 |
| * Endothelial cell contacts by non-junctional mechanisms | cell adhesion | 3.77E-03 | 8 | 40 |
| * Cell-matrix glycoconjugates | cell adhesion | 4.70E-03 | 7 | 33 |
| * TGF, WNT and cytoskeletal remodeling | cell adhesion | 7.25E-03 | 23 | 204 |
| * Slit-Robo signaling | cell adhesion | 9.76E-03 | 9 | 56 |
| * Angiotensin signaling via STATs | G-protein coupled receptor protein signaling pathway, response to extracellular stimulus | 6.79E-03 | 9 | 53 |
| * FGF-family signaling | intracellular receptor-mediated signaling pathway, response to extracellular stimulus | 2.44E-04 | 9 | 34 |
| * PDGF activation of prostacyclin synthesis | intracellular receptor-mediated signaling pathway, response to extracellular stimulus | 4.90E-03 | 5 | 18 |
| | | | | |
| Cell cycle | | | | |
| Map | Cell process | p-Value | Number of Genes in IDC gene signature | Total Number of Genes |
| * The metaphase checkpoint | cell cycle | 2.24E-09 | 15 | 36 |
| * Chromosome condensation in prometaphase | cell cycle | 4.38E-06 | 11 | 33 |
| * Role APC in cell cycle regulation | cell cycle | 2.59E-05 | 13 | 53 |
| * Nucleocytoplasmic transport of CDK/Cyclins | cell cycle | 3.52E-04 | 7 | 22 |
| * Spindle assembly and chromosome separation | cell cycle | 4.06E-04 | 15 | 86 |
| * Initiation of mitosis | cell cycle | 3.44E-03 | 9 | 48 |
| * Sister chromatid cohesion | cell cycle | 6.60E-03 | 7 | 35 |
| * Role of Nek in cell cycle regulation | cell cycle, protein kinase cascade | 4.85E-05 | 13 | 56 |

Figure 1.

| Sample | Predominant histological features |
|---|---|
| N8607A1 | Unremarkable breast tissue; no ADH/ALH; no in-situ or invasive carcinoma. Single duct with mild-moderate epithelial hyperplasia, usual type (UDH) |
| N11451A4 | Unremarkable breast tissue; no epithelial hyperplasia; no ADH/ALH; no in-situ or invasive carcinoma |
| N11123D3 | Unremarkable breast tissue; no epithelial hyperplasia; no ADH/ALH; no in-situ or invasive carcinoma |
| N11103G2 | Unremarkable breast tissue; no epithelial hyperplasia; no ADH/ALH; no in-situ or invasive carcinoma |
| N10910A4 | Unremarkable breast tissue; no ADH/ALH; no in-situ or invasive carcinoma. Fibrocystic changes (20%) |
| N10910A3 | Unremarkable breast tissue; no ADH/ALH; no in-situ or invasive carcinoma Fibrocystic changes (20%) |
| N10739D4 | Unremarkable breast tissue; no epithelial hyperplasia; no ADH/ALH; no in-situ or invasive carcinoma Occasional focus of sclerosing adenosis, columnar cell change, microcyst formation |
| N10180C2 | Unremarkable breast tissue; no epithelial hyperplasia; no ADH/ALH; no in-situ or invasive carcinoma Rare benign microcyst, mild focal chronic inflammatory infiltrate |
| N8627A2 | Unremarkable breast tissue; no epithelial hyperplasia; no ADH/ALH; no in-situ or invasive carcinoma |
| N8463I2 | Unremarkable breast tissue; no epithelial hyperplasia; no ADH/ALH; no in-situ or invasive carcinoma |
| N8380A2 | Unremarkable breast tissue; no epithelial hyperplasia; no ADH/ALH; no in-situ or invasive carcinoma |

Figure 4.

| Affy probe set id | Gene Symbol | Fold change | FDR (q value) | Regulation | DNA replication | Mitosis | CIN | MaADHC | Metastasis | Gene.Title |
|---|---|---|---|---|---|---|---|---|---|---|
| 222608_s_at | ANLN | 4.01 | <0.01 | Up-Regulated | | Y | | Y | | MAD2 mitotic arrest deficient-like 1 (yeast) |
| 206632_s_at | APOBEC3B | 3.11 | <0.01 | Up-Regulated | | | | | | cyclin-dependent kinase inhibitor 3 (CDK2-associated dual specificity phosphatase) |
| 208750_s_at | ARF1 | 2.05 | <0.01 | Up-Regulated | | | | | | H2A histone family, member Z |
| 201096_s_at | ARF4 | 2.16 | <0.01 | Up-Regulated | | | | | | ADP-ribosylation factor 4 |
| 216266_s_at | ARFGEF1 | 2.43 | <0.01 | Up-Regulated | | | | | | proliferating cell nuclear antigen |
| 219918_s_at | ASPM | 4.16 | <0.01 | Up-Regulated | | | | | | topoisomerase (DNA) II alpha 170kDa |
| 208079_s_at | AURKA | 2.98 | <0.01 | Up-Regulated | | | | | | topoisomerase (DNA) II alpha 170kDa |
| 202095_s_at | BIRC5 | 2.95 | <0.01 | Up-Regulated | | Y | | Y | | MOB1, Mps One Binder kinase activator-like 1B (yeast) |
| 209642_at | BUB1 | 2.71 | <0.01 | Up-Regulated | | Y | | Y | Cell cycle check point | BUB3 budding uninhibited by benzimidazoles 3 homolog (yeast) |
| 203755_at | BUB1B | 3.05 | <0.01 | Up-Regulated | | Y | | | | peptidylprolyl isomerase F (cyclophilin F) |
| 201457_x_at | BUB3 | 2.03 | <0.01 | Up-Regulated | | | | | | non-metastatic cells 1, protein (NM23A) expressed in |
| 223361_at | C6orf115 | 2.40 | <0.01 | Up-Regulated | | | | | | structural maintenance of chromosomes 4 |
| 228323_at | CASC5 | 2.26 | <0.01 | Up-Regulated | | | | | | ribonucleotide reductase M2 polypeptide |
| 214710_s_at | CCNB1 | 4.03 | <0.01 | Up-Regulated | | Y | CIN70 | Cell cycle check point | | baculoviral IAP repeat-containing 5 (survivin) |
| 202705_at | CCNB2 | 2.35 | <0.01 | Up-Regulated | | Y | CIN25 | Cell cycle check point | | minichromosome maintenance complex component 2 |
| 205034_at | CCNE2 | 3.99 | <0.01 | Up-Regulated | Y | | | | Y | thymidine kinase 1, soluble |
| 203213_at | CDC2 | 5.50 | <0.01 | Up-Regulated | | Y | CIN25 | Cell cycle check point | | KIAA0101 |
| 203214_x_at | CDC2 | 2.89 | <0.01 | Up-Regulated | | Y | CIN25 | Cell cycle check point | | forkhead box M1 |
| 210559_s_at | CDC2 | 4.14 | <0.01 | Up-Regulated | | Y | CIN25 | Cell cycle check point | | CTP synthase |
| 202870_s_at | CDC20 | 3.34 | <0.01 | Up-Regulated | | Y | CIN70 | Cell cycle check point | | cyclin B2 |
| 223307_at | CDCA3 | 2.24 | <0.01 | Up-Regulated | | Y | CIN70 | | | ubiquitin-conjugating enzyme E2S /// similar to Ubiquitin-conjugating enzyme E2S (Ubiquitin-conjugating enzyme E2-24 kDa) (Ubiquitin-protein ligase) (Ubiquitin carrier protein) (E2-EPF5) |
| 224753_at | CDCA5 | 2.21 | <0.01 | Up-Regulated | Y | | | | | cell division cycle 20 homolog (S. cerevisiae) |

Figure 7

| Probe ID | Gene | CIN | Fold | p-value | Regulation | | | Description |
|---|---|---|---|---|---|---|---|---|
| 1555758_a_at | CDKN3 | | 2.85 | <0.01 | Up-Regulated | | Y | ubiquitin-conjugating enzyme E2C |
| 209714_s_at | CDKN3 | | 2.97 | <0.01 | Up-Regulated | | Y | angiomotin like 2 |
| 204962_s_at | CENPA | | 2.71 | <0.01 | Up-Regulated | Cell cycle check point | Y | timeless homolog (Drosophila) |
| 207828_s_at | CENPF | | 2.60 | <0.01 | Up-Regulated | Cell cycle check point | | cell division cycle 2, G1 to S and G2 to M |
| 222848_at | CENPK | | 2.18 | <0.01 | Up-Regulated | | | cell division cycle 2, G1 to S and G2 to M |
| 218542_at | CEP55 | CIN70 | 3.46 | <0.01 | Up-Regulated | | | platelet-activating factor acetylhydrolase, isoform Ib, gamma subunit 29kDa |
| 218252_at | CKAP2 | | 2.72 | <0.01 | Up-Regulated | Y | | enhancer of zeste homolog 2 (Drosophila) |
| 204170_s_at | CKS2 | CIN70 | 6.32 | <0.01 | Up-Regulated | Y | | high-mobility group box 3 |
| 205538_at | CORO2A | | 2.24 | <0.01 | Up-Regulated | | | BUB1 budding uninhibited by benzimidazoles 1 homolog beta (yeast) |
| 202613_at | CTPS | CIN70 | 2.04 | <0.01 | Up-Regulated | | | discs, large homolog 7 (Drosophila) |
| 222958_s_at | DEPDC1 | | 2.40 | <0.01 | Up-Regulated | | | ZW10 interactor |
| 218726_at | DKFZp762E1312 | | 2.00 | <0.01 | Up-Regulated | Y | | RAD51 associated protein 1 |
| 203764_at | DLG7 | | 2.84 | <0.01 | Up-Regulated | Y | | NDC80 homolog, kinetochore complex component (S. cerevisiae) |
| 221677_s_at | DONSON | | 2.42 | <0.01 | Up-Regulated | | | CDC28 protein kinase regulatory subunit 2 |
| 218567_x_at | DPP3 | | 2.33 | <0.01 | Up-Regulated | | | structural maintenance of chromosomes 2 |
| 232510_s_at | DPP3 | | 2.20 | <0.01 | Up-Regulated | | | coagulation factor III (thromboplastin, tissue factor) |
| 218585_s_at | DTL | | 4.78 | <0.01 | Up-Regulated | | Y | kinesin family member 11 |
| 219787_s_at | ECT2 | CIN70 | 3.89 | <0.01 | Up-Regulated | Y | | dystonin |
| 203358_s_at | EZH2 | | 2.69 | <0.01 | Up-Regulated | Y | | NMA (never in mitosis gene a)-related kinase 2 |
| 225687_at | FAM83D | CIN70 | 3.33 | <0.01 | Up-Regulated | | | kinesin family member 23 |
| 213007_at | FANCI | | 2.25 | <0.01 | Up-Regulated | | | G protein-coupled receptor associated sorting protein 1 |
| 202580_x_at | FOXM1 | CIN25 | 2.37 | <0.01 | Up-Regulated | Y | | TTK protein kinase |
| 206102_at | GINS1 | | 3.27 | <0.01 | Up-Regulated | | | maternal embryonic leucine zipper kinase |
| 205436_s_at | H2AFX | CIN70 | 2.14 | <0.01 | Up-Regulated | | | centromere protein A |
| 200853_at | H2AFZ | CIN25 | 2.23 | <0.01 | Up-Regulated | | | cyclin E2 |

Figure 7 (cont...)

| ID | Gene | | Value | p | Regulation | | CIN | Checkpoint | Description | |
|---|---|---|---|---|---|---|---|---|---|---|
| 213911_s_at | H2AFZ | | | <0.01 | Up-Regulated | | CIN25 | | H2A histone family, member X | |
| 208490_x_at | HIST1H2BF | | 2.50 | <0.01 | Up-Regulated | | | | coronin, actin binding protein, 2A | |
| 203744_at | HMGB3 | | 2.71 | <0.01 | Up-Regulated | | | | extracellular matrix protein 2, female organ and adipocyte specific | |
| 207165_at | HMMR | | 3.05 | <0.01 | Up-Regulated | | | | GINS complex subunit 1 (Psf1 homolog) | |
| 217755_at | HN1 | | 3.40 | <0.01 | Up-Regulated | | Y | | apolipoprotein B mRNA editing enzyme, catalytic polypeptide-like 3B | |
| 229538_s_at | IQGAP3 | | 2.51 | <0.01 | Up-Regulated | | | | hyaluronan-mediated motility receptor (RHAMM) | |
| 202503_s_at | KIAA0101 | | 5.89 | <0.01 | Up-Regulated | | | | centromere protein F, 350/400ka (mitosin) | |
| 204444_at | KIF11 | | 3.22 | <0.01 | Up-Regulated | Y | | | aurora kinase A | |
| 218755_at | KIF20A | | 2.93 | <0.01 | Up-Regulated | | CIN25 | | histone cluster 1, H2bf | |
| 204709_s_at | KIF23 | | 2.14 | <0.01 | Up-Regulated | Y | | | ADP-ribosylation factor 1 | |
| 218355_at | KIF4A | | 2.67 | <0.01 | Up-Regulated | | CIN70 | | squalene epoxidase | |
| 211762_s_at | KPNA2 | | 3.03 | <0.01 | Up-Regulated | | | | glypican 3 | |
| 219061_s_at | LAGE3 | | 2.29 | <0.01 | Up-Regulated | | | | PDZ domain containing 2 | |
| 202779_s_at | LOC731049 /// UBE2S | | 2.36 | <0.01 | Up-Regulated | | | | nuclear cap binding protein subunit 1, 80kDa | |
| 1554768_a_at | MAD2L1 | | 2.29 | <0.01 | Up-Regulated | | CIN25 | Cell cycle check point | BUB1 budding uninhibited by benzimidazoles 1 homolog (yeast) | |
| 210058_at | MAPK13 | | 2.01 | <0.01 | Up-Regulated | Y | | | cyclin-dependent kinase inhibitor 3 (CDK2-associated dual specificity phosphatase) | |
| 202107_s_at | MCM2 | | 2.08 | <0.01 | Up-Regulated | Y | CIN25 | | membrane associated guanylate kinase, WW and PDZ domain containing 2 | |
| 212141_at | MCM4 | | 2.14 | <0.01 | Up-Regulated | Y | | | chordin-like 1 | |
| 222036_s_at | MCM4 | | 2.69 | <0.01 | Up-Regulated | Y | | | ribonucleotide reductase M2 polypeptide | |
| 204825_at | MELK | | 3.76 | <0.01 | Up-Regulated | | CIN25 | | secreted phosphoprotein 1 (osteopontin, bone sialoprotein I, early T-lymphocyte activation 1) | Y |
| 218883_s_at | MLF1IP | | 4.23 | <0.01 | Up-Regulated | Y | | | leptin receptor | |
| 201298_s_at | MOBK1B | | 2.10 | <0.01 | Up-Regulated | | | | TPX2, microtubule-associated, homolog (Xenopus laevis) | |
| 217919_s_at | MRPL42 | | 2.03 | <0.01 | Up-Regulated | | | | mitogen-activated protein kinase 13 | |
| 218663_at | NCAPG | | 2.11 | <0.01 | Up-Regulated | | | | cell division cycle 2, G1 to S and G2 to M | |

Figure 7 (cont...)

| | | | | | |
|---|---|---|---|---|---|
| 209520_s_at | NCBP1 | 2.30 | <0.01 | Up-Regulated | | | | karyopherin alpha 2 (RAG cohort 1, importin alpha 1) |
| 204162_at | NDC80 | 2.41 | <0.01 | Up-Regulated | | | Y | minichromosome maintenance complex component 4 |
| 204641_at | NEK2 | 5.55 | <0.01 | Up-Regulated | | CIN70 | Cell cycle check point | | nucleoporin 210kDa |
| 201577_at | NME1 | 2.15 | <0.01 | Up-Regulated | Y | | | | chromobox homolog 7 |
| 212316_at | NUP210 | 2.23 | <0.01 | Up-Regulated | | | | | Fanconi anemia, complementation group I |
| 218039_at | NUSAP1 | 6.41 | <0.01 | Up-Regulated | Y | | | Y | Homo sapiens, clone IMAGE:4214654, mRNA |
| 219978_s_at | NUSAP1 | 5.00 | <0.01 | Up-Regulated | Y | | | Y | Cyclin-dependent kinase inhibitor 1C (p57, Kip2) |
| 203228_at | PAFAH1B3 | 2.68 | <0.01 | Up-Regulated | | Y | | | H2A histone family, member Z |
| 219148_at | PBK | 3.06 | <0.01 | Up-Regulated | Y | | | | cyclin B1 |
| 201202_at | PCNA | 2.45 | <0.01 | Up-Regulated | Y | CIN25 | | | ADP-ribosylation factor guanine nucleotide-exchange factor 1(brefeldin A-inhibited) |
| 201490_s_at | PPIF | 2.40 | <0.01 | Up-Regulated | | | | | metallothionein 1M |
| 218009_s_at | PRC1 | 3.72 | <0.01 | Up-Regulated | | CIN25 | Cell cycle check point | Y | hematological and neurological expressed 1 |
| 222077_s_at | RACGAP1 | 3.36 | <0.01 | Up-Regulated | Y | | | | mitochondrial ribosomal protein L42 |
| 204146_at | RAD51AP1 | 2.79 | <0.01 | Up-Regulated | | CIN25 | | | protein regulator of cytokinesis 1 |
| 201890_at | RRM2 | 8.07 | <0.01 | Up-Regulated | Y | CIN70 | Nucleic Acid Biosynthesis | | nucleolar and spindle associated protein 1 |
| 209773_s_at | RRM2 | 6.73 | <0.01 | Up-Regulated | Y | CIN70 | Nucleic Acid Biosynthesis | Y | cytoskeleton associated protein 2 |
| 204240_s_at | SMC2 | 2.01 | <0.01 | Up-Regulated | Y | | | | Zwilch, kinetochore associated, homolog (Drosophila) |
| 201663_s_at | SMC4 | 2.44 | <0.01 | Up-Regulated | Y | | | | kinesin family member 4A |
| 209875_s_at | SPP1 | 5.70 | <0.01 | Up-Regulated | | | | | centrosomal protein 55kDa |
| 209218_at | SQLE | 3.25 | <0.01 | Up-Regulated | | | | Y | dipeptidyl-peptidase 3 |
| 203046_s_at | TIMELESS | 2.12 | <0.01 | Up-Regulated | | | | | denticleless homolog (Drosophila) |
| 1554408_a_at | TK1 | 2.72 | <0.01 | Up-Regulated | Y | | Nucleic Acid Biosynthesis | | non-SMC condensin 1 complex, subunit G |
| 202338_at | TK1 | 2.86 | <0.01 | Up-Regulated | Y | | Nucleic Acid Biosynthesis | Y | hypothetical protein DKFZp762E1312 |
| 222642_s_at | TMEM33 | 2.01 | <0.01 | Up-Regulated | | | | | kinesin family member 20A |
| 201291_s_at | TOP2A | 7.56 | <0.01 | Up-Regulated | Y | CIN25 | | | MLF1 interacting protein |
| 201292_at | TOP2A | 6.03 | <0.01 | Up-Regulated | Y | CIN25 | | | L antigen family, member 3 |

Figure 7 (cont...)

| Probe | Gene | Fold | p-value | Regulation | | CIN | Category | Description |
|---|---|---|---|---|---|---|---|---|
| 210052_s_at | TPX2 | 3.73 | <0.01 | Up-Regulated | Y | CIN25 | | PDZ binding kinase |
| 204822_at | TTK | 3.27 | <0.01 | Up-Regulated | Y | CIN25 | | epithelial cell transforming sequence 2 oncogene |
| 1554696_s_at | TYMS | 2.05 | <0.01 | Up-Regulated | Y | | Nucleic Acid Biosynthesis | asp (abnormal spindle) homolog, microcephaly associated (Drosophila) |
| 202954_at | UBE2C | 3.26 | <0.01 | Up-Regulated | | CIN25 | | nucleolar and spindle associated protein 1 |
| 223229_at | UBE2T | 4.99 | <0.01 | Up-Regulated | | | | downstream neighbor of SON |
| 225655_at | UHRF1 | 6.34 | <0.01 | Up-Regulated | | | | minichromosome maintenance complex component 4 |
| 222804_x_at | WDR32 | 2.04 | <0.01 | Up-Regulated | | | | Rac GTPase activating protein 1 |
| 225676_s_at | WDSOF1 | 2.26 | <0.01 | Up-Regulated | | | | anillin, actin binding protein |
| 218349_s_at | ZWILCH | 2.11 | <0.01 | Up-Regulated | | | | transmembrane protein 33 |
| 204026_s_at | ZWINT | 4.46 | <0.01 | Up-Regulated | | CIN70 | | serum deprivation response (phosphatidylserine binding protein) |
| 228273_at | | 3.77 | <0.01 | Up-Regulated | | | | thymidine kinase 1, soluble |
| 229490_s_at | | 2.52 | <0.01 | Up-Regulated | | | | thymidylate synthetase |
| 203002_at | AMOTL2 | 2.39 | <0.01 | Down-Regulated | | | | WD repeats and SOF1 domain containing |
| 212914_at | CBX7 | 2.61 | <0.01 | Down-Regulated | | | | family with sequence similarity 83, member D |
| 228693_at | CCDC50 | 3.07 | <0.01 | Down-Regulated | | | | adult retina protein |
| 213348_at | CDKN1C | 3.65 | <0.01 | Down-Regulated | | | | CDNA FLJ34585 fis, clone KIDNE2008758 |
| 224352_s_at | CFL2 | 2.42 | <0.01 | Down-Regulated | | | | CDNA FLJ34585 fis, clone KIDNE2008758 |
| 209763_at | CHRDL1 | 8.05 | <0.01 | Down-Regulated | | | | MRNA; cDNA DKFZp586K1922 (from clone DKFZp586K1922) |
| 204455_at | DST | 11.94 | <0.01 | Down-Regulated | | | | MRNA; cDNA DKFZp586K1922 (from clone DKFZp586K1922) |
| 206101_at | ECM2 | 2.97 | <0.01 | Down-Regulated | | | | CDNA FLJ39389 fis, clone PLACE6003621 |
| 204363_at | F3 | 2.50 | <0.01 | Down-Regulated | | | | synaptopodin 2 |
| 209220_at | GPC3 | 3.87 | <0.01 | Down-Regulated | | | | Transcribed locus |
| 204793_at | GPRASP1 | 3.04 | <0.01 | Down-Regulated | | | | Transcribed locus |
| 209894_at | LEPR | 5.51 | <0.01 | Down-Regulated | | | | cancer susceptibility candidate 5 |
| 225956_at | LOC153222 | 2.22 | <0.01 | Down-Regulated | Y | | | coiled-coil domain containing 50 |
| 209737_at | MAGI2 | 2.06 | <0.01 | Down-Regulated | | | | Transcribed locus |

Figure 7 (cont...)

| | | | | |
|---|---|---|---|---|
| 217546_at | MT1M | 3.14 | <0.01 | Down-Regulated | IQ motif containing GTPase activating protein 3 |
| 209493_at | PDZD2 | 2.38 | <0.01 | Down-Regulated | dipeptidyl-peptidase 3 |
| 238447_at | RBMS3 | 5.26 | <0.01 | Down-Regulated | zinc finger and BTB domain containing 20 |
| 222717_at | SDPR | 6.01 | <0.01 | Down-Regulated | Transcribed locus |
| 227662_at | SYNPO2 | 4.91 | <0.01 | Down-Regulated | CDNA FLJ36544 fis, clone TRACH2006378 |
| 225093_at | UTRN | 2.24 | <0.01 | Down-Regulated | RNA binding motif, single stranded interacting protein |
| 235308_at | ZBTB20 | 2.89 | <0.01 | Down-Regulated | Transcribed locus |
| 213158_at | | 3.84 | <0.01 | Down-Regulated | WD repeat domain 32 |
| 226250_at | | 2.81 | <0.01 | Down-Regulated | centromere protein K |
| 226252_at | | 2.89 | <0.01 | Down-Regulated | DEP domain containing 1 |
| 227082_at | | 3.51 | <0.01 | Down-Regulated | ubiquitin-conjugating enzyme E2T (putative) |
| 227121_at | | 2.55 | <0.01 | Down-Regulated | cell division cycle associated 3 |
| 227646_at | | 5.35 | <0.01 | Down-Regulated | chromosome 6 open reading frame 115 |
| 227719_at | | 2.21 | <0.01 | Down-Regulated | cofilin 2 (muscle) |
| 235556_at | | 2.18 | <0.01 | Down-Regulated | cell division cycle associated 5 |
| 235570_at | | 4.02 | <0.01 | Down-Regulated | utrophin |
| 243584_at | | 3.93 | <0.01 | Down-Regulated | ubiquitin-like, containing PHD and RING finger domains, 1 |

Figure 7 (cont...)

| Probe set id | Gene Symbol | Fold change | FDR (q value) | Up-Regulation | DNA replication | Mitosis | CIN | Ma | ADHC | Metastasis |
|---|---|---|---|---|---|---|---|---|---|---|
| 222608_s_at | ANLN | 4.01 | <0.01 | Over-exp | | Y | | Y | | |
| 202095_s_at | BIRC5 | 2.95 | <0.01 | Over-exp | | Y | | Y | | |
| 209642_at | BUB1 | 2.71 | <0.01 | Over-exp | | Y | | Y | Cell cycle check point | |
| 203755_at | BUB1B | 3.05 | <0.01 | Over-exp | | Y | | | | |
| 214710_s_at | CCNB1 | 4.03 | <0.01 | Over-exp | | Y | CIN70 | | Cell cycle check point | |
| 202705_at | CCNB2 | 2.35 | <0.01 | Over-exp | | Y | CIN25 | | Cell cycle check point | |
| 205034_at | CCNE2 | 3.99 | <0.01 | Over-exp | Y | | | Y | | Y |
| 203213_at | CDC2 | 5.50 | <0.01 | Over-exp | | Y | CIN25 | | Cell cycle check point | |
| 202870_s_at | CDC20 | 3.34 | <0.01 | Over-exp | | Y | CIN70 | | Cell cycle check point | |
| 223307_at | CDCA3 | 2.24 | <0.01 | Over-exp | | Y | CIN70 | | | |
| 209714_s_at | CDKN3 | 2.97 | <0.01 | Over-exp | | | | Y | | |
| 204962_s_at | CENPA | 2.71 | <0.01 | Over-exp | | | | Y | Cell cycle check point | Y |
| 207828_s_at | CENPF | 2.60 | <0.01 | Over-exp | | | | | Cell cycle check point | |
| 204170_s_at | CKS2 | 6.32 | <0.01 | Over-exp | | | CIN70 | Y | | |
| 218585_s_at | DTL | 4.78 | <0.01 | Over-exp | | | | | | Y |
| 219787_s_at | ECT2 | 3.89 | <0.01 | Over-exp | | Y | CIN70 | | | |
| 203358_s_at | EZH2 | 2.69 | <0.01 | Over-exp | Y | | CIN70 | | | |
| 202580_x_at | FOXM1 | 2.37 | <0.01 | Over-exp | | Y | CIN25 | | | |
| 200853_at | H2AFZ | 2.23 | <0.01 | Over-exp | | | CIN25 | | | |
| 217755_at | HN1 | 3.40 | <0.01 | Over-exp | | | | Y | | |
| 218755_at | KIF20A | 2.93 | <0.01 | Over-exp | | | CIN25 | | Cell cycle check point | |
| 204709_s_at | KIF23 | 2.14 | <0.01 | Over-exp | | Y | | | | |
| 1554768_a_at | MAD2L1 | 2.29 | <0.01 | Over-exp | | Y | CIN25 | | Cell cycle check point | |
| 210058_at | MAPK13 | 2.01 | <0.01 | Over-exp | | Y | | | | |
| 202107_s_at | MCM2 | 2.08 | <0.01 | Over-exp | Y | | CIN25 | | | |
| 204825_at | MELK | 3.76 | <0.01 | Over-exp | | Y | CIN25 | | | Y |
| 204162_at | NDC80 | 2.41 | <0.01 | Over-exp | | | | | | Y |
| 204641_at | NEK2 | 5.55 | <0.01 | Over-exp | | | CIN70 | | Cell cycle check point | |
| 201577_at | NME1 | 2.15 | <0.01 | Over-exp | | | | Y | | |
| 218039_at | NUSAP1 | 6.41 | <0.01 | Over-exp | | Y | | | | Y |
| 203228_at | PAFAH1B3 | 2.68 | <0.01 | Over-exp | | | | Y | | |
| 201202_at | PCNA | 2.45 | <0.01 | Over-exp | Y | | CIN25 | | | |
| 218009_s_at | PRC1 | 3.72 | <0.01 | Over-exp | | | CIN25 | Y | Cell cycle check point | Y |
| 222077_s_at | RACGAP1 | 3.36 | <0.01 | Over-exp | | | | Y | | |
| 204146_at | RAD51AP1 | 2.79 | <0.01 | Over-exp | Y | | CIN25 | | | |
| 201890_at | RRM2 | 8.07 | <0.01 | Over-exp | Y | | CIN70 | Y | Nucleic Acid Biosynthesis | |
| 209218_at | SQLE | 3.25 | <0.01 | Over-exp | | | | Y | | |
| 202338_at | TK1 | 2.86 | <0.01 | Over-exp | Y | | | Y | Nucleic Acid Biosynthesis | |
| 201291_s_at | TOP2A | 7.56 | <0.01 | Over-exp | | Y | CIN25 | Y | | |
| 210052_s_at | TPX2 | 3.73 | <0.01 | Over-exp | | Y | CIN25 | | | |
| 204822_at | TTK | 3.27 | <0.01 | Over-exp | | Y | CIN25 | | | |
| 1554696_s_at | TYMS | 2.05 | <0.01 | Over-exp | Y | | | | Nucleic Acid Biosynthesis | |
| 202954_at | UBE2C | 3.26 | <0.01 | Over-exp | | | CIN25 | | | |

Figure 8.

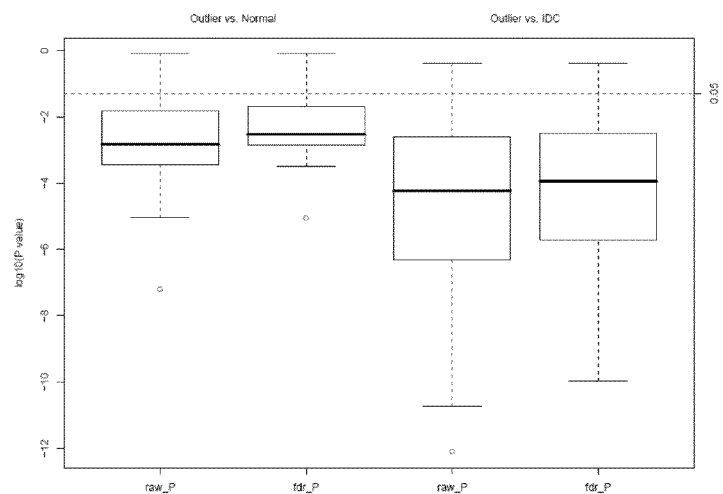

Figure 9.

| Map | Cell process | p-Value | Genes | |
|---|---|---|---|---|
| * The metaphase checkpoint | cell cycle | 3.50E-21 | 14 | 36 |
| * Role APC in cell cycle regulation | cell cycle | 1.93E-13 | 11 | 53 |
| * Spindle assembly and chromosome separation | cell cycle | 5.01E-11 | 11 | 86 |
| * Chromosome condensation in prometaphase | cell cycle | 1.11E-10 | 8 | 33 |
| * Role of Nek in cell cycle regulation | cell cycle, protein kinase cascade | 2.23E-07 | 7 | 56 |
| * Nucleocytoplasmic transport of CDK/Cyclins | cell cycle | 2.18E-05 | 4 | 22 |
| * Initiation of mitosis | cell cycle | 3.23E-05 | 5 | 48 |
| * Sister chromatid cohesion | cell cycle | 1.44E-04 | 4 | 35 |
| * Transition and termination of DNA replication | cell cycle | 1.61E-04 | 4 | 36 |
| * Cell cycle (generic schema) | cell cycle | 1.01E-03 | 3 | 26 |
| * ATM/ATR regulation of G2/M checkpoint | cell cycle | 1.40E-03 | 3 | 29 |

Figure 10.

| |
|---|
| DNA replication: Genes Induce at G1-S and S-phase |
| CCNE2 |
| CDCA5 |
| DONSON |
| EZH2 |
| MCM2 |
| MCM4 |
| MLF1IP |
| PCNA |
| RAD51AP1 |
| RRM2 |
| SMC2L1 |
| SMC4L1 |
| TK1 |
| TYMS |
| |
| Mitosis: Genes Induced in G2 and G2-M |
| ANLN |
| BIRC5 |
| BUB1 |
| BUB1B |
| CCNB1 |
| CCNB2 |
| CDC2 |
| CDC20 |
| CDCA3 |
| CKAP2 |
| DKFZp762E1312 |
| DLG7 |
| ECT2 |
| FOXM1 |
| KIF11 |
| KIF23 |
| LOC153222 |
| MAD2L1 |
| MAPK13 |
| MELK |
| NUSAP1 |
| PBK |
| TOP2A |
| TPX2 |
| TTK |

Figure 11.

(a)
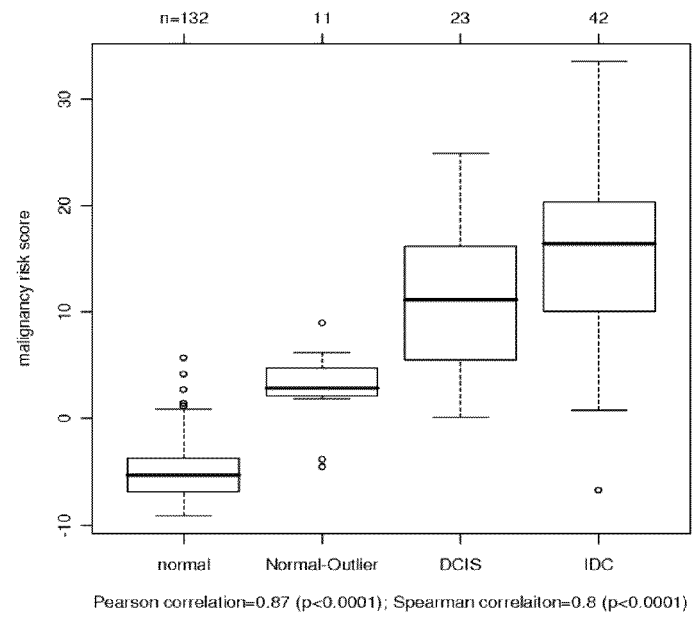
(b)
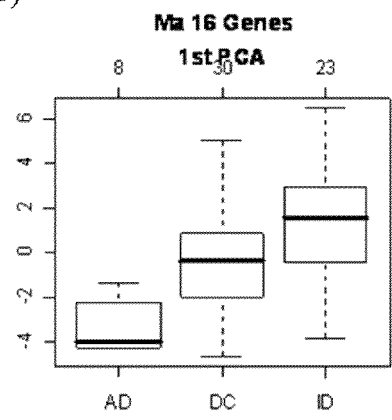
(c)
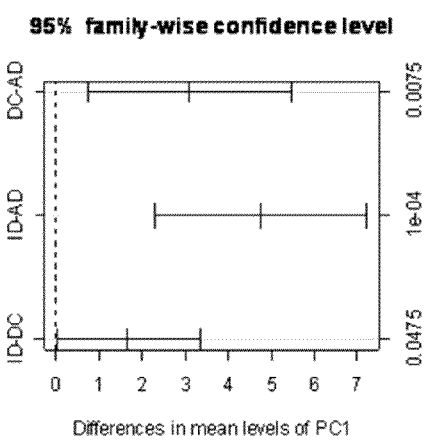
Figure 13.

(a)
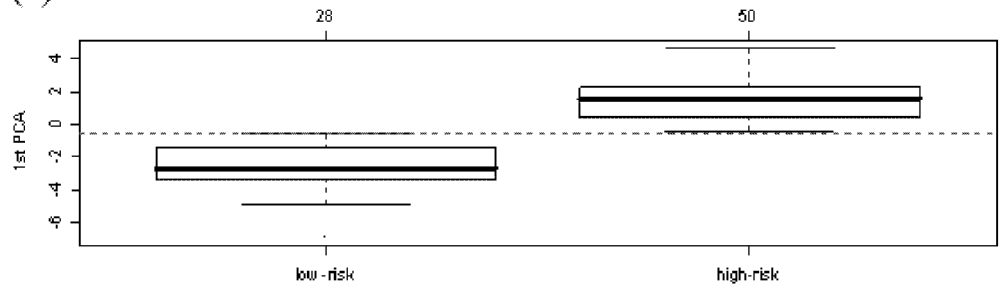
(b)
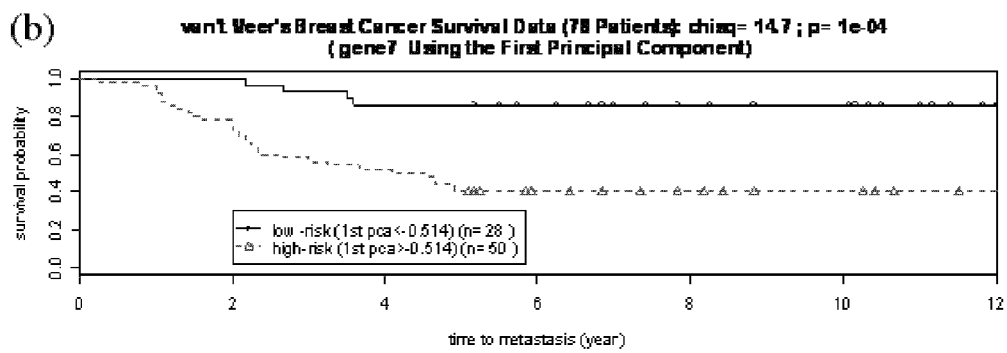
(c)
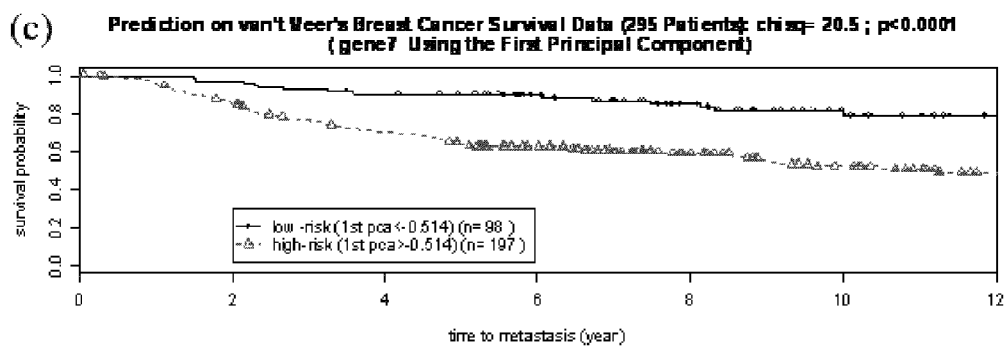
Figure 21.

N=histological normal, but sampled as tumor
T=histological tumor, but sampled as normal
O: IDC-like normal

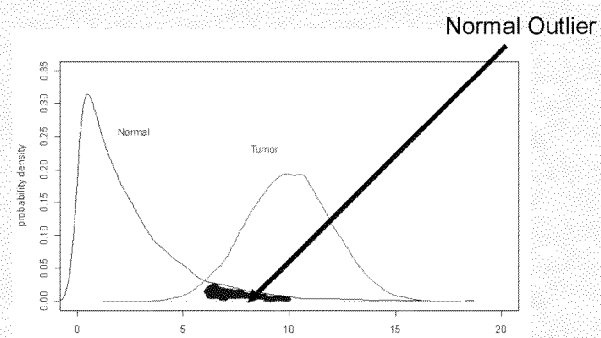
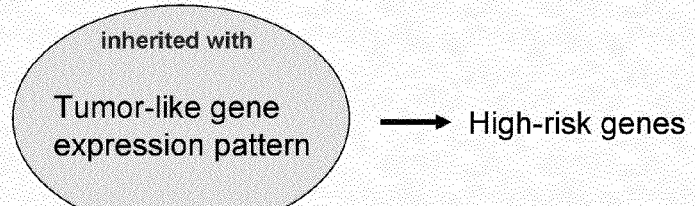
Figure 24.

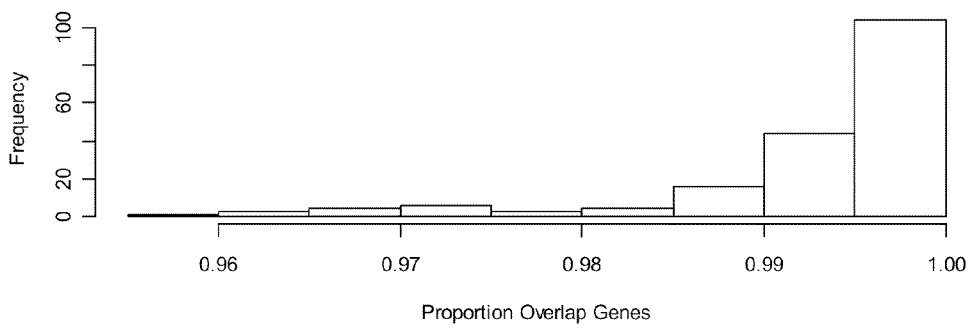
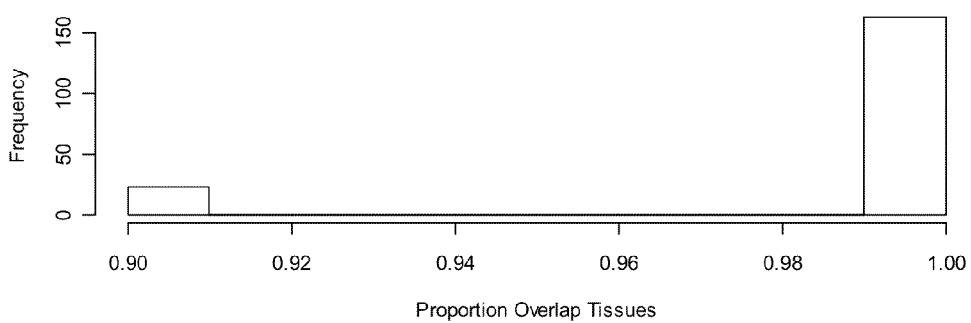
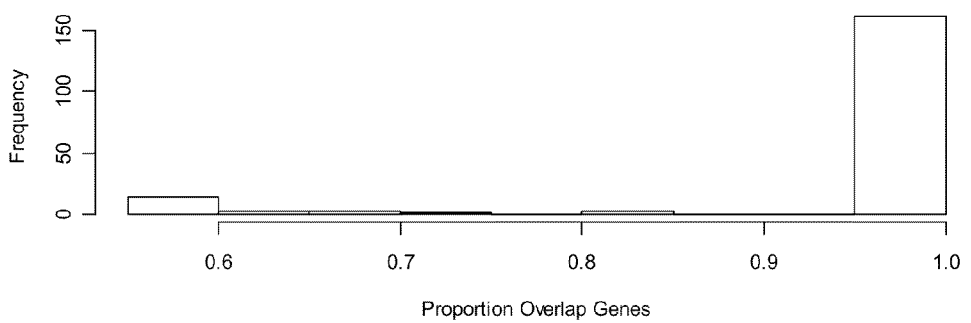
Figure 25A.

| Probe Set ID | Gene Title | Gene symbol | Correlation with the malignancy-risk core | |
|---|---|---|---|---|
| | | | Spearman correlation | Pearson correlation |
| 234354_x_at | V-erb-b2 erythroblastic leukemia viral oncogene homolog 2, neuro/glioblastoma derived oncogene homolog (avian) | ERBB2 (HER2) | 0.37 | 0.53 |
| 216836_s_at | v-erb-b2 erythroblastic leukemia viral oncogene homolog 2, neuro/glioblastoma derived oncogene homolog (avian) | ERBB2 (HER2) | 0.43 | 0.43 |
| 210930_s_at | v-erb-b2 erythroblastic leukemia viral oncogene homolog 2, neuro/glioblastoma derived oncogene homolog (avian) | ERBB2 (HER2) | 0.46 | 0.63 |
| 234275_at | Estrogen receptor 1 | ESR1 (ER) | 0.08 | 0.13 |
| 217190_x_at | estrogen receptor 1 | ESR1 (ER) | 0.06 | 0.14 |
| 217163_at | Estrogen receptor 1 | ESR1 (ER) | 0.03 | 0.06 |
| 215552_s_at | estrogen receptor 1 | ESR1 (ER) | 0.13 | 0.29 |
| 215551_at | estrogen receptor 1 | ESR1 (ER) | 0.11 | 0.22 |
| 211627_x_at | estrogen receptor 1 /// estrogen receptor 1 | ESR1 (ER) | -0.14 | -0.07 |
| 211235_s_at | estrogen receptor 1 | ESR1 (ER) | 0.21 | 0.29 |
| 211234_x_at | estrogen receptor 1 | ESR1 (ER) | 0.13 | 0.25 |
| 211233_x_at | estrogen receptor 1 | ESR1 (ER) | 0.17 | 0.29 |
| 205225_at | estrogen receptor 1 | ESR1 (ER) | 0.04 | -0.17 |
| 211120_x_at | estrogen receptor 2 (ER beta) | ESR2 (ER) | -0.11 | -0.03 |
| 211119_at | estrogen receptor 2 (ER beta) | ESR2 (ER) | 0.04 | 0.01 |
| 211118_x_at | estrogen receptor 2 (ER beta) | ESR2 (ER) | 0.10 | 0.18 |
| 211117_x_at | estrogen receptor 2 (ER beta) | ESR2 (ER) | 0.08 | 0.13 |
| 210780_at | estrogen receptor 2 (ER beta) | ESR2 (ER) | -0.09 | -0.06 |
| 208305_at | progesterone receptor | PGR (PR) | 0.17 | 0.18 |
| 240776_at | Progesterone receptor | PGR (PR) | 0.25 | 0.21 |

Figure 26B.

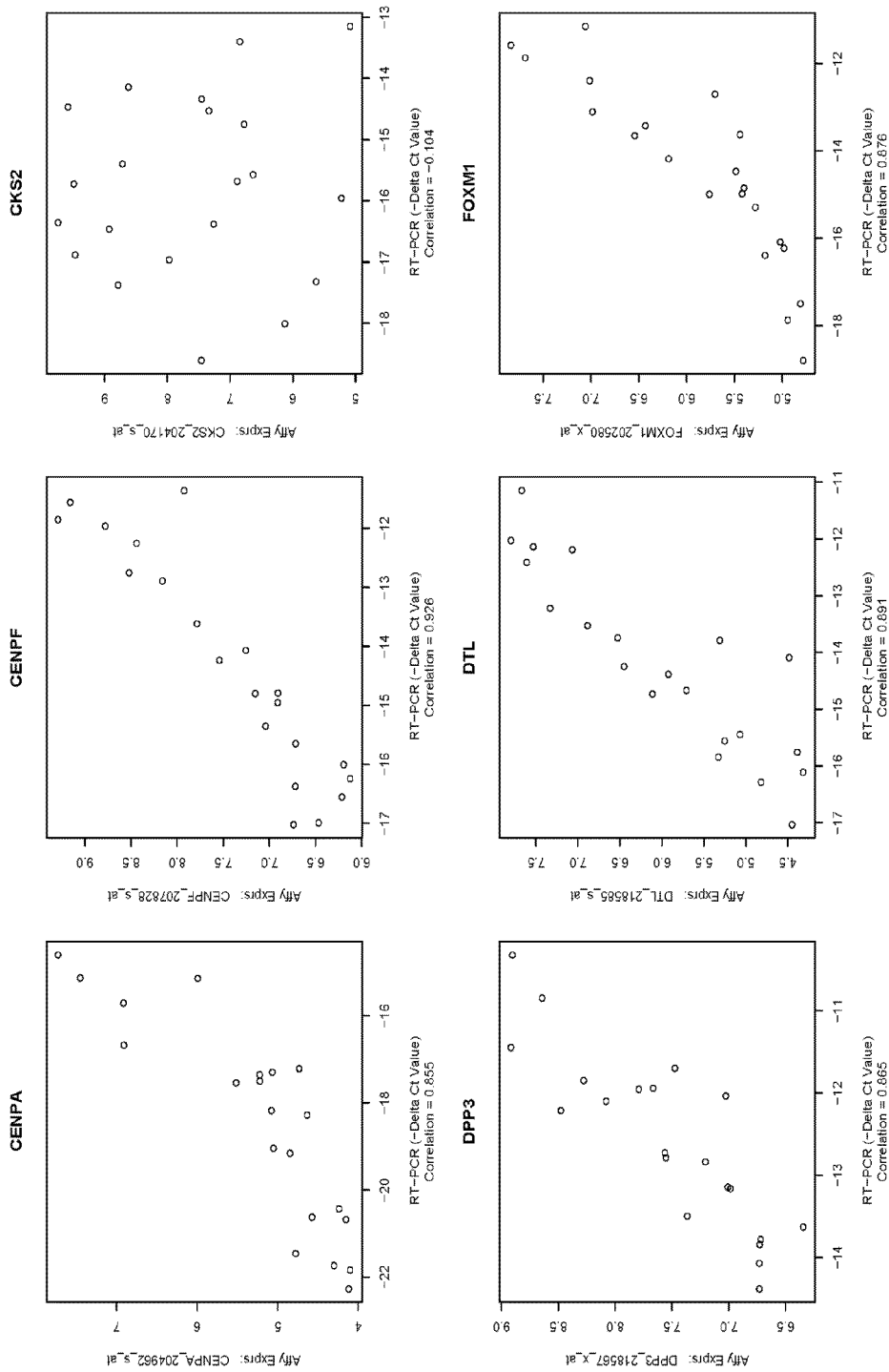
Figure 28 (cont...)

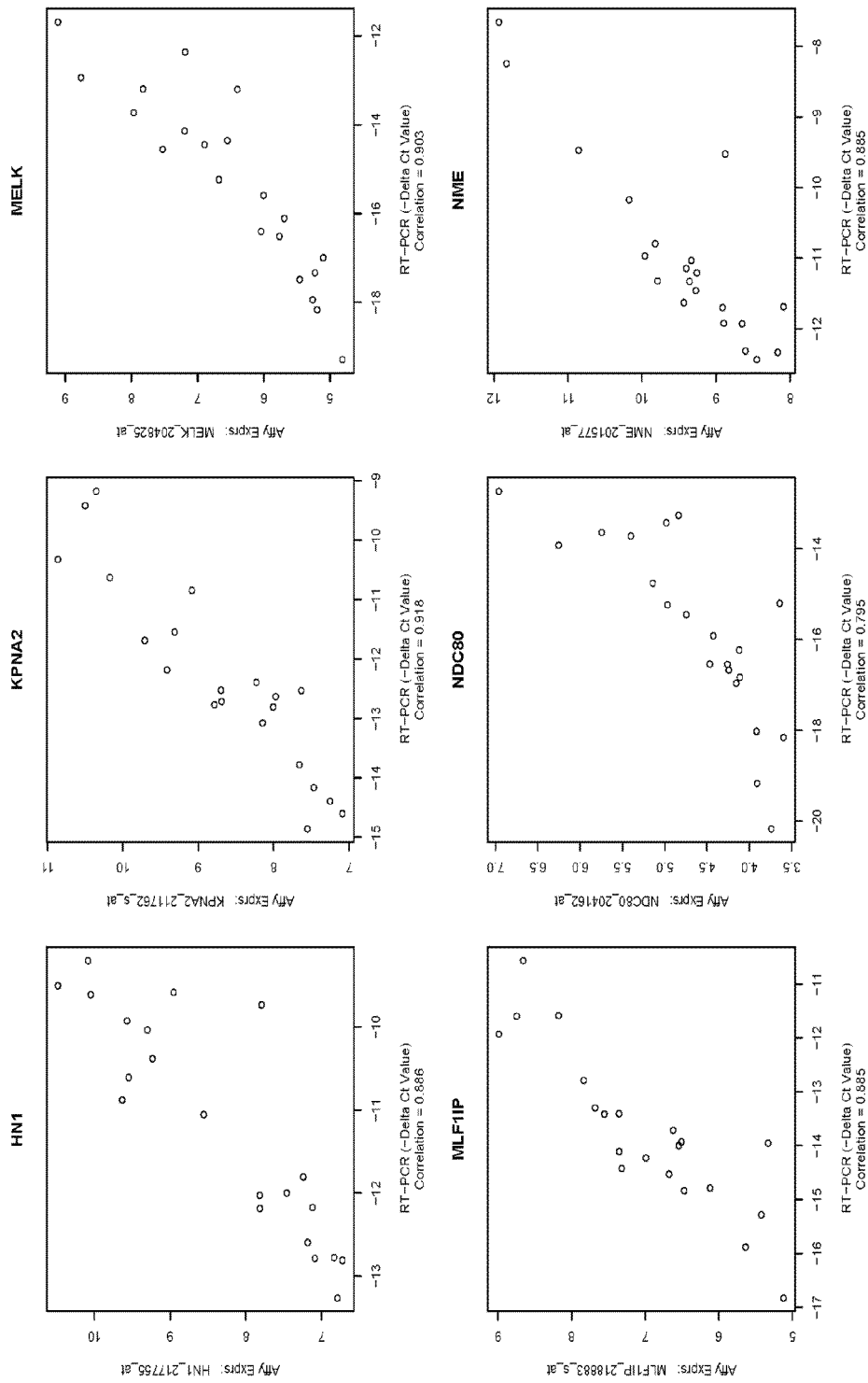
Figure 28 (cont...)

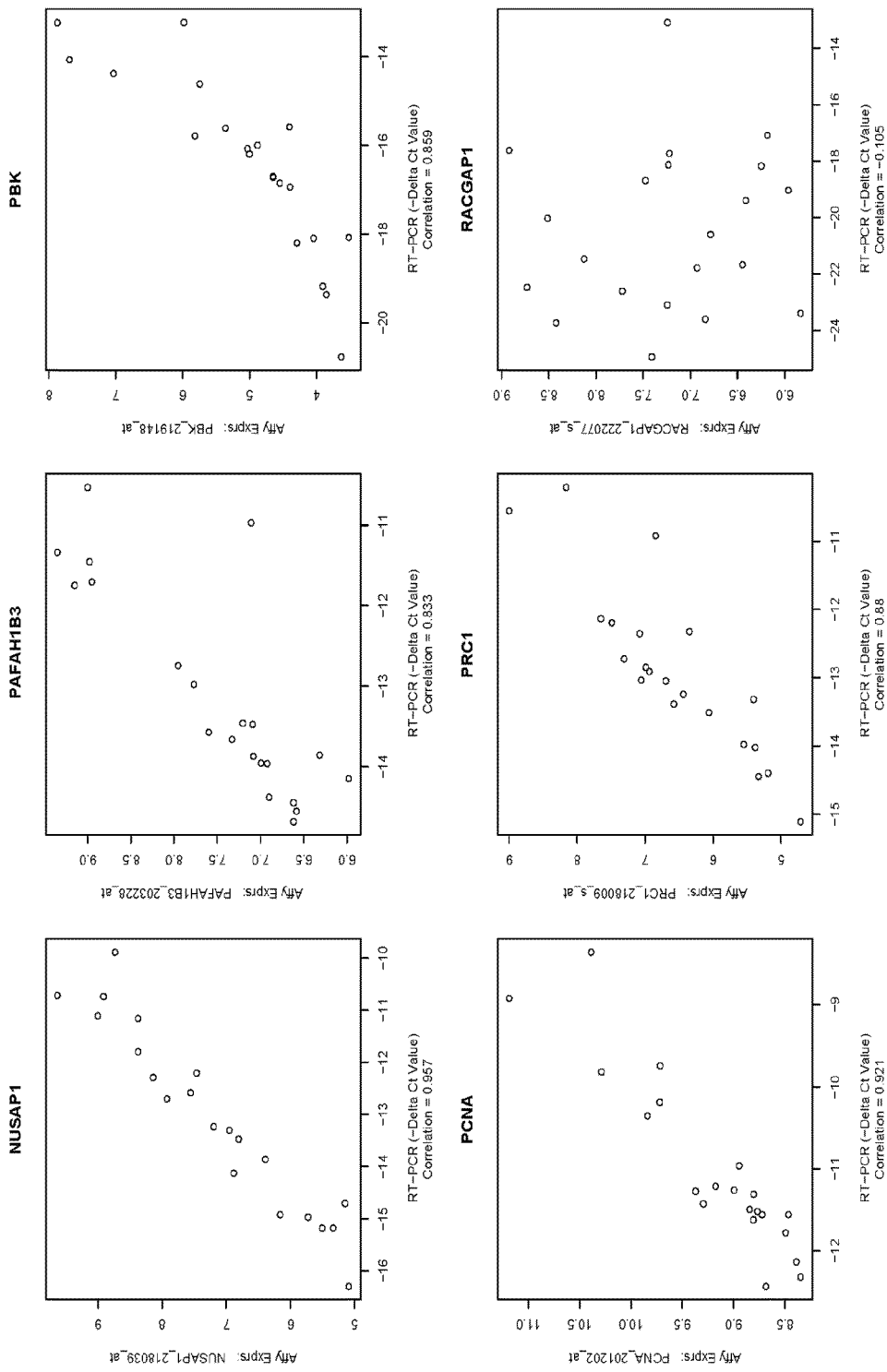
Figure 28 (cont...)

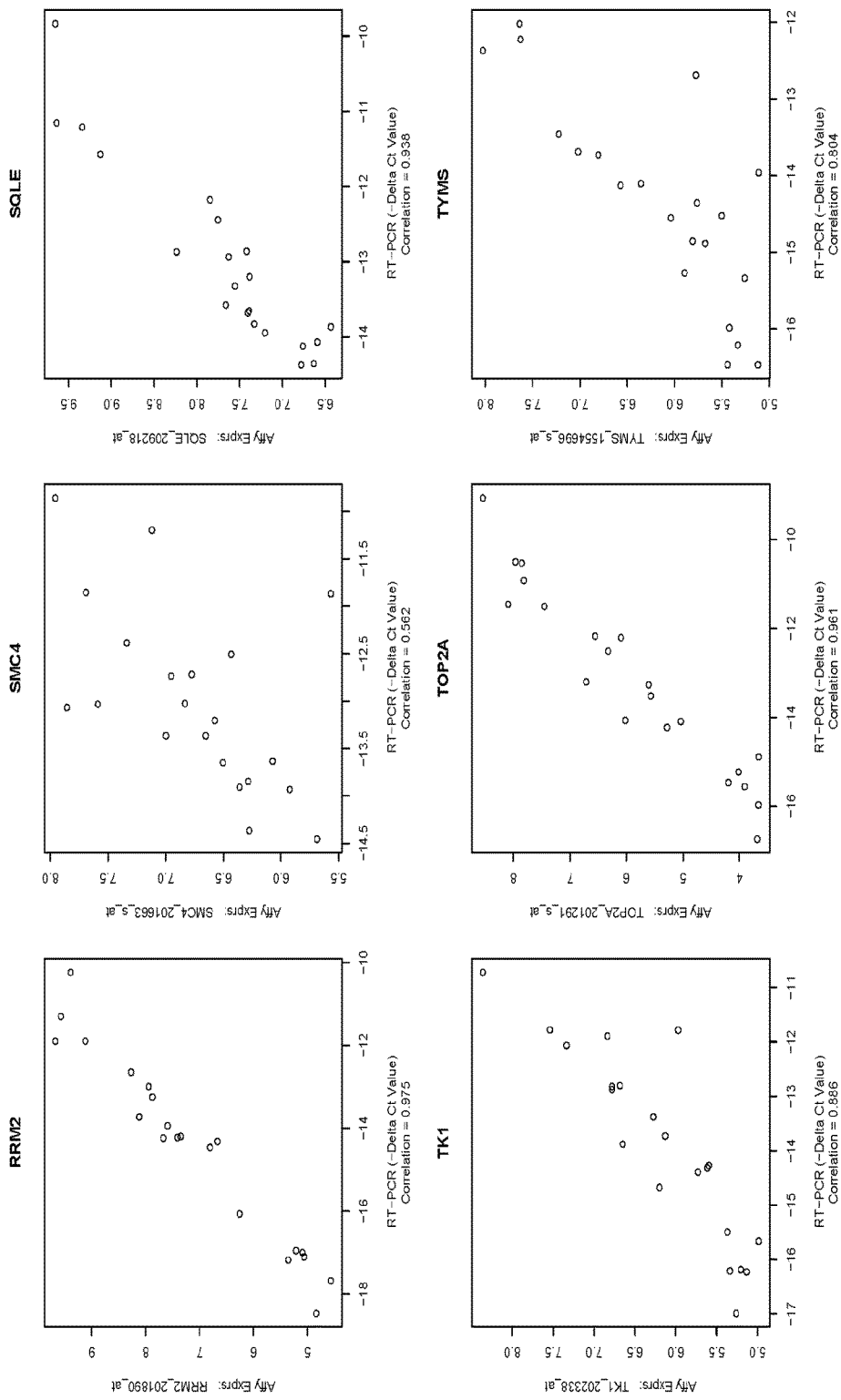
Figure 28 (cont...)

| Gene Name | Pearson correlation | p value |
|---|---|---|
| ANLN | 0.28 | 0.0261 |
| BIRC5 | 0.38 | 0.0028 |
| BUB1 | 0.31 | 0.0145 |
| CCNE2 | 0.34 | 0.0082 |
| CDKN3 | 0.42 | 0.0008 |
| CENPA | 0.37 | 0.0032 |
| CKS2 | 0.32 | 0.0127 |
| HN1 | 0.35 | 0.0063 |
| NME1 | 0.32 | 0.0127 |
| PAFAH1B3 | 0.43 | 0.0005 |
| PRC1 | 0.43 | 0.0006 |
| RACGAP1 | 0.38 | 0.0022 |
| RRM2 | 0.39 | 0.0019 |
| SQLE | 0.27 | 0.0339 |
| TK1 | 0.33 | 0.0099 |
| TOP2A | 0.48 | 0.0001 |

Figure 31A.

| Affy.probe.set.id | Gene.Symbol | p value | regulation |
|---|---|---|---|
| 212914_at | CBX7 | 0.0020 | DOWN |
| 210559_s_at | CDC2 | 0.0179 | UP |
| 209714_s_at | CDKN3 | 0.0256 | UP |
| 218542_at | CEP55 | 0.0423 | UP |
| 218252_at | CKAP2 | 0.0396 | UP |
| 202613_at | CTPS | 0.0039 | UP |
| 203764_at | DLG7 | 0.0318 | UP |
| 213911_s_at | H2AFZ | 0.0204 | UP |
| 211762_s_at | KPNA2 | 0.0147 | UP |
| 204825_at | MELK | 0.0207 | UP |
| 218883_s_at | MLF1IP | 0.0196 | UP |
| 219978_s_at | NUSAP1 | 0.0418 | UP |
| 209773_s_at | RRM2 | 0.0167 | UP |
| 204240_s_at | SMC2 | 0.0301 | UP |
| 210052_s_at | TPX2 | 0.0417 | UP |
| 218349_s_at | ZWILCH | 0.0271 | UP |

| ID | Gene Symbol | Train Set (p value) | Test Set (p value) | Gene Title |
|---|---|---|---|---|
| NM_001809 | CENPA | 0.00042 | 4.30E-06 | centromere protein A, 17kDa |
| NM_003981 | PRC1 | 0.0012 | 1.50E-07 | protein regulator of cytokinesis 1 |
| NM_004702 | CCNE2 | 0.0046 | 1.20E-05 | cyclin E2 |
| NM_006101 | KNTC2 | 0.00016 | 0.007 | kinetochore associated 2 |
| NM_014791 | MELK | 0.0032 | 0.00076 | maternal embryonic leucine zipper kinase |
| NM_016359 | NUSAP1 | 0.00017 | 1.60E-05 | nucleolar and spindle associated protein 1 |
| NM_016448 | DTL | 0.00011 | 1.40E-05 | denticleless homolog (Drosophila) |

Figure 33A

| Probe set id | Gene Symbol | P value for training set | P value for test set |
|---|---|---|---|
| NM_018685 | ANLN | 0.0260 | 0.0065 |
| NM_003158 | AURKA | 0.0100 | <0.0001 |
| NM_003600 | AURKA | 0.0056 | <0.0001 |
| NM_001168 | BIRC5 | 0.0005 | <0.0001 |
| NM_004336 | BUB1 | 0.0025 | 0.0016 |
| NM_001211 | BUB1B | 0.0022 | 0.0003 |
| NM_001007 | BUB3 | 0.0026 | 0.0002 |
| NM_004701 | CCNB2 | 0.0007 | <0.0001 |
| NM_004702 | CCNE2 | 0.0046 | <0.0001 |
| NM_001786 | CDC2 | 0.0064 | 0.0100 |
| NM_005192 | CDKN3 | 0.0010 | 0.0011 |
| NM_001809 | CENPA | 0.0004 | <0.0001 |
| NM_005196 | CENPF | 0.0017 | 0.0240 |
| NM_018131 | CEP55 | 0.0006 | 0.0006 |
| NM_001905 | CTPS | 0.0019 | 0.0006 |
| NM_017779 | DEPDC1 | 0.0055 | 0.0002 |
| NM_018410 | DKFZp762E1312 | 0.0008 | <0.0001 |
| NM_014750 | DLG7 | 0.0008 | 0.0003 |
| NM_016448 | DTL | 0.0001 | <0.0001 |
| NM_004456 | EZH2 | 0.0016 | 0.0003 |
| NM_002106 | H2AFZ | 0.0024 | 0.0005 |
| NM_005342 | HMGB3 | 0.0090 | 0.0006 |
| NM_016185 | HN1 | 0.0060 | 0.0006 |
| NM_014736 | KIAA0101 | 0.0077 | 0.0059 |
| NM_005733 | KIF20A | 0.0011 | <0.0001 |
| NM_004856 | KIF23 | 0.0061 | 0.0027 |
| NM_012310 | KIF4A | 0.0019 | 0.0009 |
| NM_006101 | KNTC2 | 0.0002 | 0.0070 |
| NM_002266 | KPNA2 /// LOC728860 | 0.0055 | 0.0002 |
| NM_006014 | LAGE3 | 0.0230 | 0.0021 |
| NM_001003 | LEPR /// RBMS3 | 0.0160 | 0.0290 |
| NM_002358 | MAD2L1 | 0.0014 | 0.0008 |
| NM_014791 | MELK | 0.0032 | 0.0008 |

Figure 33B

| NM_002497 | NEK2 | 0.0250 | 0.0012 |
| NM_016359 | NUSAP1 | 0.0002 | <0.0001 |
| NM_018454 | NUSAP1 | 0.0025 | 0.0002 |
| NM_007019 | PAK3 /// UBE2C | 0.0090 | <0.0001 |
| NM_002592 | PCNA | 0.0140 | 0.0006 |
| NM_003981 | PRC1 | 0.0012 | <0.0001 |
| NM_013277 | RACGAP1 | 0.0170 | <0.0001 |
| NM_001034 | RRM2 | 0.0052 | <0.0001 |
| NM_003258 | TK1 | 0.0035 | <0.0001 |
| NM_003318 | TTK | 0.0076 | 0.0270 |
| NM_001071 | TYMS | 0.0110 | <0.0001 |
| NM_014501 | UBE2S /// LOC731049 | 0.0100 | 0.0003 |
| NM_014176 | UBE2T | 0.0490 | 0.0001 |
| NM_013282 | UHRF1 | 0.0002 | 0.0086 |
| NM_007057 | ZWINT | 0.0018 | <0.0001 |

Figure 33B (cont...)

| Gene Symbol | P value | | Gene Symbol | P value |
|---|---|---|---|---|
| ANLN | 0.003133 | | H2AFZ | 7.04E-05 |
| ARF1 | 6.83E-06 | | HMMR | 0.019638 |
| ARF4 | 0.000139 | | HN1 | 6.85E-05 |
| BIRC5 | 0.000126 | | KIAA0101 | 0.000282 |
| BUB1 | 0.02205 | | KIF4A | 0.035201 |
| BUB1B | 0.002202 | | LEPR | 0.040935 |
| BUB3 | 0.000234 | | MAPK13 | 0.001544 |
| CCNB1 | 0.000352 | | MCM2 | 1.98E-05 |
| CCNB2 | 2.11E-05 | | MCM4 | 0.003243 |
| CCNE2 | 0.009371 | | MRPL42 | 0.00052 |
| CDC2 | 0.005387 | | NCBP1 | 1.17E-06 |
| CDKN1C | 3.89E-06 | | NME1 | 7.07E-05 |
| CDKN3 | 0.000609 | | PAFAH1B3 | 0.00012 |
| CENPA | 1.26E-05 | | PPIF | 0.00096 |
| CENPF | 0.00616 | | RACGAP1 | 0.000117 |
| CFL2 | 0.008065 | | SDPR | 9.51E-06 |
| CKAP2 | 0.000931 | | SPP1 | 0.004216 |
| CKS2 | 0.000378 | | SQLE | 0.035426 |
| CTPS | 0.000472 | | TIMELESS | 0.000148 |
| DONSON | 0.048888 | | TK1 | 0.005265 |
| DPP3 | 3.19E-05 | | TOP2A | 0.000376 |
| ECM2 | 0.016785 | | TTK | 0.015438 |
| FOXM1 | 0.001796 | | TYMS | 0.000764 |
| GPC3 | 0.007866 | | UTRN | 8.35E-07 |
| H2AFX | 6.55E-05 | | ZWINT | 3.76E-06 |

Figure 34B

| Gene Name | Probe Set ID | p |
|---|---|---|
| SMC4 | 201663_s_at | 0.029 |
| CCNE2 | 205034_at | 1.30E-05 |
| KPNA2 /// KPNA2 | 211762_s_at | 0.039 |
| MLF1IP | 218883_s_at | 0.00042 |

Figure 35A

| Gene Name | Probe Set ID | p |
|---|---|---|
|  | 218726_at | 0.0079 |
| ASPM | 219918_s_at | 0.00022 |
| AURKA | 208079_s_at | 7.10E-06 |
| BIRC5 | 202095_s_at | 0.0031 |
| BUB1 | 209642_at | 0.00055 |
| BUB1B | 203755_at | 0.00062 |
| CBX7 | 212914_at | 0.029 |
| CCNB1 | 214710_s_at | 0.002 |
| CCNB2 | 202705_at | 0.00031 |
| CCNE2 | 205034_at | 1.30E-05 |
| CDC2 | 203213_at | 0.0011 |
| CDC20 | 202870_s_at | 0.0057 |
| CDKN3 | 209714_s_at | 0.017 |
| CENPA | 204962_s_at | 0.0029 |
| CENPF | 207828_s_at | 0.0088 |
| CEP55 | 218542_at | 0.00031 |
| CKAP2 | 218252_at | 7.20E-06 |
| CKS2 | 204170_s_at | 0.0068 |
| DLG7 | 203764_at | 0.00014 |
| DONSON | 221677_s_at | 0.0022 |
| DPP3 | 218567_x_at | 0.036 |
| DTL | 218585_s_at | 0.00025 |
| ECT2 | 219787_s_at | 0.019 |
| EZH2 | 203358_s_at | 0.00091 |
| F3 | 204363_at | 0.0053 |
| FOXM1 | 202580_x_at | 0.014 |
| GINS1 | 206102_at | 2.90E-05 |
| H2AFZ | 213911_s_at | 0.037 |
| HMMR | 207165_at | 2.10E-05 |
| KIAA0101 | 202503_s_at | 0.0023 |
| KIAA1794 | 213007_at | 0.0041 |
| KIF11 | 204444_at | 0.00018 |
| KIF20A | 218755_at | 0.016 |
| KIF23 | 204709_s_at | 0.0087 |
| KIF4A | 218355_at | 0.014 |
| KPNA2 /// KPNA2 | 211762_s_at | 0.039 |
| LAGE3 | 219061_s_at | 0.021 |
| MCM2 | 202107_s_at | 0.029 |
| MCM4 | 222036_s_at | 0.045 |
| MELK | 204825_at | 0.00091 |
| MLF1IP | 218883_s_at | 0.00042 |
| NCAPG | 218663_at | 0.00095 |
| NEK2 | 204641_at | 3.70E-06 |

Figure 35B

| | | |
|---|---|---|
| NME1 | 201577_at | 0.044 |
| NUSAP1 | 218039_at | 0.00049 |
| PAFAH1B3 | 203228_at | 0.019 |
| PBK | 219148_at | 0.0032 |
| PCNA | 201202_at | 0.00057 |
| PRC1 | 218009_s_at | 0.00059 |
| RACGAP1 | 222077_s_at | 1.40E-06 |
| RAD51AP1 | 204146_at | 0.0012 |
| RRM2 | 201890_at | 2.00E-04 |
| RRM2 | 209773_s_at | 0.0014 |
| SMC4 | 201663_s_at | 0.029 |
| SPP1 | 209875_s_at | 0.027 |
| SQLE | 209218_at | 0.032 |
| TIMELESS | 203046_s_at | 0.015 |
| TK1 | 202338_at | 0.032 |
| TOP2A | 201291_s_at | 0.024 |
| TOP2A | 201292_at | 0.0025 |
| TTK | 204822_at | 0.00024 |
| UBE2C /// PAK3 | 202954_at | 0.0012 |
| UBE2S /// | 202779_s_at | 0.015 |
| ZWINT | 204026_s_at | 0.0036 |

Figure 35B (cont...)

| u95.id | symbol | p.value | H | L | fold | Gene.Name |
|---|---|---|---|---|---|---|
| 41081_at | BUB1 | 0.048 | 4.063 | 3.934 | 1.093 | BUB1 budding uninhibited by benzimidazoles 1 homolog (yeast) |
| 35699_at | BUB1B | 0.009 | 5.354 | 4.890 | 1.380 | BUB1 budding uninhibited by benzimidazoles 1 homolog beta (yeast) |
| 39109_at | C20orf1 | 0.008 | 7.518 | 6.995 | 1.438 | chromosome 20 open reading frame 1 |
| 36894_at | CBX7 | 0.017 | 7.509 | 7.943 | 1.351 | chromobox homolog 7 |
| 1945_at | CCNB1 | 0.011 | 5.468 | 5.057 | 1.330 | cyclin B1 |
| 32263_at | CCNB2 | 0.007 | 5.409 | 5.053 | 1.280 | cyclin B2 |
| 1803_at | CDC2 | 0.018 | 6.072 | 5.841 | 1.173 | cell division cycle 2, G1 to S and G2 to M |
| 33324_s_at | CDC2 | 0.024 | 4.501 | 4.349 | 1.112 | cell division cycle 2, G1 to S and G2 to M |
| 40915_r_at | CDC2 | 0.007 | 3.557 | 3.349 | 1.155 | cell division cycle 2, G1 to S and G2 to M |
| 1787_at | CDKN1C | 0.032 | 5.098 | 5.455 | 1.281 | cyclin-dependent kinase inhibitor 1C (p57, Kip2) |
| 1599_at | CDKN3 | 0.036 | 5.353 | 5.049 | 1.235 | cyclin-dependent kinase inhibitor 3 (CDK2-associated dual specificity phosphatase) |
| 527_at | CENPA | 0.006 | 5.433 | 5.247 | 1.138 | centromere protein A, 17kDa |
| 37302_at | CENPF | 0.009 | 5.912 | 5.451 | 1.376 | centromere protein F, 350/400ka (mitosin) |
| 40891_f_at | DXS9879E | 0.004 | 9.402 | 8.949 | 1.368 | DNA segment on chromosome X (unique) 9879 expressed sequence |
| 40619_at | E2-EPF | 0.032 | 7.638 | 7.050 | 1.502 | ubiquitin carrier protein |
| 894_g_at | E2-EPF | 0.017 | 9.039 | 8.519 | 1.435 | ubiquitin carrier protein |
| 37305_at | EZH2 | 0.036 | 6.615 | 6.355 | 1.198 | enhancer of zeste homolog 2 (Drosophila) |
| 38116_at | KIAA0101 | 0.017 | 7.626 | 7.088 | 1.452 | KIAA0101 gene product |
| 40726_at | KIF11 | 0.024 | 5.481 | 5.094 | 1.308 | kinesin family member 11 |
| 37171_at | KIF23 | 0.009 | 3.904 | 3.688 | 1.162 | kinesin family member 23 |
| 40407_at | KPNA2 | 0.042 | 6.311 | 5.860 | 1.366 | karyopherin alpha 2 (RAG cohort 1, importin alpha 1) |
| 1721_g_at | MAD2L1 | 0.022 | 4.266 | 3.996 | 1.205 | MAD2 mitotic arrest deficient-like 1 (yeast) |
| 366_s_at | NEK2 | 0.032 | 4.185 | 4.024 | 1.118 | NIMA (never in mitosis gene a)-related kinase 2 |
| 1521_at | NME1 | 0.005 | 8.609 | 7.978 | 1.548 | non-metastatic cells 1, protein (NM23A) expressed in |
| 1985_s_at | NME1 | 0.026 | 8.435 | 7.909 | 1.440 | non-metastatic cells 1, protein (NM23A) expressed in |
| 39073_at | NME1 | 0.010 | 7.623 | 7.084 | 1.453 | non-metastatic cells 1, protein (NM23A) expressed in |

Figure 36A

| 34878_at | SMC4L1 | 0.024 | 4.139 | 3.822 | 1.246 | SMC4 structural maintenance of chromosomes 4-like 1 (yeast) |
| 35839_at | SQLE | 0.001 | 6.562 | 5.782 | 1.717 | squalene epoxidase |
| 34852_g_at | STK6 | 0.003 | 6.021 | 5.658 | 1.286 | serine/threonine kinase 6 |
| 1592_at | TOP2A | 0.003 | 6.541 | 6.031 | 1.424 | topoisomerase (DNA) II alpha 170kDa |
| 40145_at | TOP2A | 0.016 | 5.771 | 5.312 | 1.375 | topoisomerase (DNA) II alpha 170kDa |
| 904_s_at | TOP2A | 0.006 | 4.831 | 4.414 | 1.335 | topoisomerase (DNA) II alpha 170kDa |
| 1651_at | UBE2C | 0.002 | 8.571 | 7.904 | 1.588 | ubiquitin-conjugating enzyme E2C |
| 35995_at | ZWINT | 0.028 | 7.429 | 6.772 | 1.578 | ZW10 interactor |

Figure 36A (cont...)

MALIGNANCY-RISK SIGNATURE FROM HISTOLOGICALLY NORMAL BREAST TISSUE

CROSS-REFERENCE TO RELATED APPLICATIONS

This application claims the priority benefit of the U.S. Provisional Application Ser. No. 61/020,575, filed Jan. 11, 2008; which is hereby incorporated by reference in its entirety.

STATEMENT OF GOVERNMENT INTEREST

This invention was made with Government support under Grant Nos. CA076292, CA098522 and CA112215 awarded by the National Institutes of Health. The Government has certain rights in the invention.

FIELD OF INVENTION

This invention relates to cancer screening and therapy. Specifically, the invention entails screening pre-pathological breast tissue for potential oncogenesis.

BACKGROUND OF THE INVENTION

Throughout this specification, reference numbering is sometimes used to refer to the full citation for the references, which can be found in the "Reference Bibliography" after the Examples section. The disclosure of all patents, patent applications, and publications cited herein are hereby incorporated by reference in their entirety for all purposes.

In 2004, 186,772 women and 1,815 men were diagnosed with breast cancer, making it the second most common cancer in women. Conventional treatment includes surgery, chemotherapy, hormone therapy, and radiation. Breast conserving approaches have been increasingly used to treat invasive breast cancer. Historical data, however, have reported a 40% local recurrence rate after lumpectomy without radiotherapy[1]. Furthermore, the rate of local recurrence after mastectomy has been reported at 10-30%[2]. Local recurrence rate following lumpectomy without radiotherapy for ductal carcinoma in situ is as high as 63%, with invasive cancer occurring in over 36% of cases[3,4], and a median recurrence between 2 and 6 years, depending on the initial stage of the resected tumor. Radiotherapy significantly reduces rate of local recurrence to 10% or less, but does not completely eliminate the risk of cancer[5]. Collectively, these data demonstrate the potential apparent normal breast possesses to harbor pre-malignant changes or very early malignancy at molecular level, and emphasize the insensitivity of the current strategies to detect disease at an early molecular stage, even in patients known to be at high-risk. The potential benefit of a molecular signature as an indication of risk for subsequent development of breast cancer would, therefore, be very useful in screening applications.

Currently, it is estimated that false negatives and new cancers previously screened as negative may amount to 2-4% of the new cancer cases following breast biopsy[6]. Determination of molecular markers of malignancy in histologically normal breast may improve the potential for breast biopsy to identify at-risk patients, refine the current practice of intra-operative assessment of margins of the resected breast tissues based on histology alone, and may prove useful in guiding treatment choices after lumpectomy. For example, it is clear that not all patients require or benefit from post-lumpectomy radiotherapy, which often leads to considerable cosmetic defects in the residual breast.

Accordingly, there is a need for the ability for to predict which individuals, who have histologically normal breast tissue, will likely develop breast cancer, or breast cancer recurrence, or metastasis of breast cancer. The ability for physicians and/or others of skill in the art allows for personalized treatment of patients and avoids unnecessary treatments that are not beneficial to the patient's health.

The invention provides for, inter alia, malignancy-risk gene signatures that predict the risk of developing breast cancer, the recurrence of breast cancer, and/or the metastasis of breast cancer; methods of using such signatures, and kits containing arrays of malignancy-risk gene signatures. Thus, one objective of the invention was to establish high cancer-risk gene signatures in histologically normal breast tissues obtained from patients with invasive breast cancer. Other objectives are described in greater detail infra.

As detailed further in the Examples, outlier gene signatures were derived to assess cancer risk from the 143 histologically normal breast tissues derived from patients who underwent mastectomy for breast carcinoma. Up to four normal breast samples, adjacent to an invasive ductal carcinoma, were obtained from each patient. Validation results indicated that the outlier gene signature had multiple predictive properties, including potential to predict cancer risk, disease progression, and metastasis. Since the outlier genes were highly associated with cell proliferation, it is conceivable that these proliferation genes may have a role in the earliest stages of breast cancer development and subsequent progression.

These signatures have numerous clinical applications including, but not limited to, assessing risk of breast cancer development following routine breast biopsy, assessing the need for adjuvant radiotherapy after lumpectomy, and determining the need for completion mastectomy following lumpectomy for the breast cancer patient and other treatment plans that are personalized for the patient and thus, fulfill several needs in this field.

BRIEF SUMMARY OF THE INVENTION

The invention described herein provides for malignancy-risk gene signature and methods for determining or predicting the likelihood that an individual who has histologically normal breast tissue will develop breast cancer, have recurrence of breast cancer, and/or for predicting spread of breast cancer by using malignancy-risk gene signatures.

Accordingly, in one aspect, the invention provides for methods for predicting the likelihood for the development of breast cancer in an individual comprising: (a) analyzing a breast tissue sample from the individual wherein the sample comprises substantially histologically normal cells from the individual to obtain a first gene expression profile; (b) comparing the first gene expression profile to a malignancy-risk gene signature as depicted in Table 6; and (c) predicting the likelihood that the individual will develop cancer if the individual expresses at least 10 of the malignancy-risk genes. In one embodiment, the individual is suspected of having breast cancer or who has had breast cancer or who is at risk for breast cancer. In another embodiment, the individual has had or currently has atypical hyperplasia. In another embodiment, the individual has had or currently has fibroadenoma. In another embodiment, the breast cancer is selected from the group consisting of: invasive ductal carcinoma (IDC), ductal carcinoma in situ (DCIS), lobular carcinoma in situ (LCIS), and invasive lobular carcinoma (ILC). In another embodiment, the individual had had a surgical procedure to remove breast cancer, breast tumor, or breast lesion. In one embodiment, the surgical procedure is a lumpectomy or a mastectomy. In another embodiment, the individual has initiated chemotherapy treatment either before, or after the surgical procedure. In another embodiment, the breast tissue sample is obtained ipsilaterally with the cancer, tumor, or lesion.

In another aspect, the invention provides for methods for predicting the likelihood for the spread of breast cancer in an individual who has had or currently has breast cancer comprising: (a) obtaining a breast tissue sample from the individual comprising substantially histologically normal cells from the individual; (b) analyzing the sample to obtain a first gene expression profile; (c) comparing the first gene expression profile to a malignancy-risk gene signature listed in Table 6; and (d) predicting the likelihood that the individual will develop spread of breast cancer if the individual expresses at least 10 of the malignancy-risk genes. In one embodiment, the breast cancer is selected from the group consisting of: invasive ductal carcinoma (IDC), ductal carcinoma in situ (DCIS), lobular carcinoma in situ (LCIS), and invasive lobular carcinoma (ILC). In another embodiment, the spread of cancer is metastasis. In another embodiment, the individual had had a surgical procedure to remove breast cancer. In another embodiment, the surgical procedure is a lumpectomy or a mastectomy. In another embodiment, the individual has initiated chemotherapy or radiation treatment before or after the surgical procedure.

In any of the aspects or embodiments, the malignancy-risk signature is at least 10 genes selected from Table 3. In any of the aspects or embodiments, the malignancy-risk signature is selected from the group consisting of the following genes from Table 6: APOBEC3B, C6orf115, CASC5, CORO2A, FAM83D, HIST1H2BF, MOBK1B, WDSOF1, IQGAP3, AMOTL2, CCDC50, CHRDL1, GPRASP1, MAGI2, RBMS3, SYNPO2, Affymetrix probe set id 213158_at, Affymetrix probe set id 226250_at, Affymetrix probe set id 226252_at, Affymetrix probe set id 227082_at, Affymetrix probe set id 227121_at, Affymetrix probe set id 227646_at, Affymetrix probe set id 227719_at, Affymetrix probe set id 235556_at, Affymetrix probe set id 235570_at, and Affymetrix probe set id 243584_at. In any of the aspects or embodiments, the malignancy-risk genes are selected from the genes in Table 7. In any of the aspects or embodiments, the malignancy-risk gene signature is selected from the genes in Table 8. In any of the aspects or embodiments, the malignancy-risk gene signature does not include at least one of the genes in FIG. 31A. In any of the aspects or embodiments, the malignancy-risk gene signature does not include at least one of the genes in FIG. 32B. In any of the aspects or embodiments, the predicting of the likelihood that the individual will develop breast cancer or spread of breast cancer is expression of at least 117 of the malignancy-risk genes. In any of the aspects or embodiments, the malignancy-risk gene signature does not include at least one of the genes in FIG. 33A. In any of the aspects or embodiments, the malignancy-risk gene signature is selected from the genes in FIG. 33B. In any of the aspects or embodiments, the malignancy-risk gene signature is selected from the genes in FIG. 34B. In any of the aspects or embodiments, the malignancy-risk gene signature does not include at least one of the genes in FIG. 35A. In any of the aspects or embodiments, the malignancy-risk gene signature is selected from the genes in FIG. 35B. In any of the aspects or embodiments, the malignancy-risk gene signature is selected from the genes in FIG. 36A.

In another aspect, the invention provides for malignancy-risk gene signatures for use in predicting or diagnosing cancer wherein the gene signature comprises at least 10 genes of Table 6. In one embodiment, the gene signature comprises at least 10 genes of Table 3. In another embodiment, the gene signature does not include at least 1 gene selected from the genes listed in FIGS. 31A, 32B, 33A, and 35A. In another embodiment, wherein the gene signature comprises at least about 30 genes selected from the group consisting of the genes in Table 3, Table 7, Table 8, FIG. 33B, FIG. 34B, FIG. 35B, and FIG. 36A. In another embodiment, the gene signature comprises at least 10 genes selected from the group consisting of: APOBEC3B, C6orf115, CASC5, CORO2A, FAM83D, HIST1H2BF, MOBK1B, WDSOF1, IQGAP3, AMOTL2, CCDC50, CHRDL1, GPRASP1, MAGI2, RBMS3, SYNPO2, Affymetrix probe set id 213158_at, Affymetrix probe set id 226250_at, Affymetrix probe set id 226252_at, Affymetrix probe set id 227082_at, Affymetrix probe set id 227121_at, Affymetrix probe set id 227646_at, Affymetrix probe set id 227719_at, Affymetrix probe set id 235556_at, Affymetrix probe set id 235570_at, and Affymetrix probe set id 243584_at.

In another aspect, the invention provides for arrays comprising polynucleotides hybridizing to at least about 30 malignancy-risk signature genes immobilized on a solid surface, wherein said gene signature genes are listed in Table 6.

In another aspect, the invention provides for arrays comprising polynucleotides hybridizing to at least about 30 malignancy-risk signature genes immobilized on a solid surface, wherein said gene signature genes are listed in Table 3, Table 7, Table 8, FIG. 33B, FIG. 34B, FIG. 35B, and FIG. 36A.

In another aspect, the invention provides for kits comprising the array comprising malignancy-risk gene signatures of any one of the above and a set of instructions for determining an individual's likelihood of developing breast cancer.

In another aspect, the invention provides for kits comprising the array comprising malignancy-risk gene signatures of any one of the above and a set of instructions for determining an individual's likelihood of having breast cancer spread to other locations in the individual's body.

In another aspect, the invention provides for computer readable media comprising a malignancy-risk signature which comprises at least about 30 genes from Table 6.

In another aspect, the invention provides for computer readable media comprising a malignancy-risk signature which comprises at least about 30 genes from Table 3, Table 7, Table 8, FIG. 33B, FIG. 34B, FIG. 35B, and FIG. 36A.

BRIEF DESCRIPTION OF THE DRAWINGS

FIG. 1 is a table of the pathway analysis of IDC gene signature with two predominant cellular processes: cell adhesion and cell cycle.

FIG. 4 is a table of the histological description of the 11 outlier breast tissues

FIG. 7 is a table of the outlier gene list. "Y" symbol was used to index the association of each outlier gene with DNA replication, mitosis, CIN index, disease progression (Ma), cancer risk (ADHC), and metastasis. For CIN, we listed the association with CIN 25 gene (CIN25) and CIN 70 gene (CIN70) signature (Note CIN25 is a subset set of CIN70). For disease progression, we listed 16 overlapped outlier genes with an increasing pattern from ADH to IDC in Ma dataset. For cancer risk, we listed outlier genes associated with two highly significant up-regulated pathways in Poola's ADH study: Cell Cycle Check Points and Nucleic Acid Biosynthesis. For metastasis, we listed 7 outlier genes associated with the 70 gene signature in Vant der veer' study.

FIG. 8 is a table showing the subset of outlier genes associated with DNA replication, mitosis, CIN index, disease progression, and metastasis. Y" symbol was used to index the association of each outlier gene with DNA replication, mito- sis, CIN index, disease progression (Ma), cancer risk (ADHC), and metastasis. For CIN, we listed the association with CIN 25 gene (CIN25) and CIN 70 gene (CIN70) signature (Note CIN25 is a subset set of CIN70). For disease progression, we listed 16 overlapped outlier genes with an increasing pattern from ADH to IDC in Ma dataset. For cancer risk, we listed outlier genes associated with two highly significant up-regulated pathways in Poola's ADH study: Cell Cycle Check Points and Nucleic Acid Biosynthesis. For metastasis, we listed 7 outlier genes associated with the 70 gene signature in Vant der veer' study.

FIG. 9 is a graph comparing the outlier gene expression between the outlier normal tissue versus normal breast and IDC tissues based on two-sample t-test. Distribution of p value was displayed in two ways: unadjusted p value (labeled as raw_P) from the two-sample t-test and the adjusted p value based on Benjamini's false discovery rate approach (labeled as fdr_P). To see how gene expression of outlier breast tissue (OBT) is different from histologically normal breast (HNB) and IDC, two-sample t-test was used to test expression change between (a) HNB versus OBTs and (b) IDC versus OBTs for the outlier genes. Results showed that 82% of the outlier genes varied significantly between HNB and OBT with an adjusted p<0.05, whereas 94% of the outlier genes varied significantly between IDC and OBT. These results suggest that expression of the outlier genes was distinct from both normal and IDC tissues.

FIG. 10 is a table of the pathway analysis of outlier gene signature with one predominant cellular processes: cell cycle FIG. 11 is a table of the outlier genes associated with DNA replication and mitosis

FIG. 13 is a graph of the external validation for disease progression. (a) DCIS samples from Moffitt breast cancer study: The DCIS samples were used to evaluate the disease progression feature for the outlier gene signature. The built-up PCA model from our outlier gene signature was used to calculate the first PCA score for the DCIS tissues. Result showed a progression trend from normal, outlier, DCSI, to IDC with a correlation >0.8 and a p value <0.001 (Pearson correlation (0.87) or Spearman Correlation (0.8) was calculated by scoring the disease status as 0 to 3 for normal to IDC). (b) Ma's study: Principal component analysis was performed using the first principal component for the 16 overlapped outlier genes which show an increasing pattern of gene expression. The first panel displayed distribution of the first PC score (y axis) among the three groups: ADH, DCIS (DC), and IDC (ID). The second panel was 95% confidence interval of pair-wise comparison for the first PC score among the three groups with adjusted p value in the right-hand side's y axis.

FIG. 21 shows that external validation to assessing prognostic feature in Vant der veer breast metastasis dataset. (a) Displays the distribution of the first PCA score of both risk groups based on the overlapped 7 genes. The cutoff of the first PCA score was determined by recursive partitioning and regression trees. (b) The survival curves of the two risk groups for the dataset with 78 metastasis patients. Survival analysis with logrank test showed a significant difference of the two survival curves. (c) Survival curves for the dataset with 295 metastasis patients. Logrank test also showed a significant separation between the two risk groups.

FIG. 24 shows the heuristic algorithm of the Outlier Tissue Approach.

FIG. 25A depicts the distribution of the proportion of selected IDC genes by LOOCV overlapping with the ones by the whole dataset (first panel), the distribution of the proportion of selected outlier tissues by LOOCV overlapping with the original ones by the whole dataset second panel) and the distribution of the proportion of selected malignancy-risk (labeled as outlier) genes by LOOCV overlapped with the original ones by the whole dataset (third panel).

FIG. 26B depicts the correlation of each ER, PR, and Herb2 gene with malignancy-risk score (Pearson and Spearman correlation).

FIG. 31 shows the external evaluation for cancer progression in Ma et al's study. FIG. 31A is a list of malignancy-risk genes with p value <0.05.

FIG. 32 shows the external evaluation for cancer risk in Poola et al's ADH study.

FIG. 34 shows the external evaluation for cancer progression in the Chanrion study. FIG. 34B lists malignancy-risk genes with p value <0.05.

FIG. 35 shows the external evaluation to assess prognostic feature in the Wang study dataset. FIG. 35A shows the Univariate Cox proportional hazards model for the four genes in common with malignancy-risk signature. FIG. 35B shows the Univariate Cox proportional hazards model for the 102 malignancy-risk genes with p value <0.05.

FIG. 36 shows the external evaluation for breast lymph node development in Huang's breast study. FIG. 36 A lists malignancy-risk genes with p value <0.05.

DETAILED DESCRIPTION OF THE PREFERRED EMBODIMENT

Figure 2:
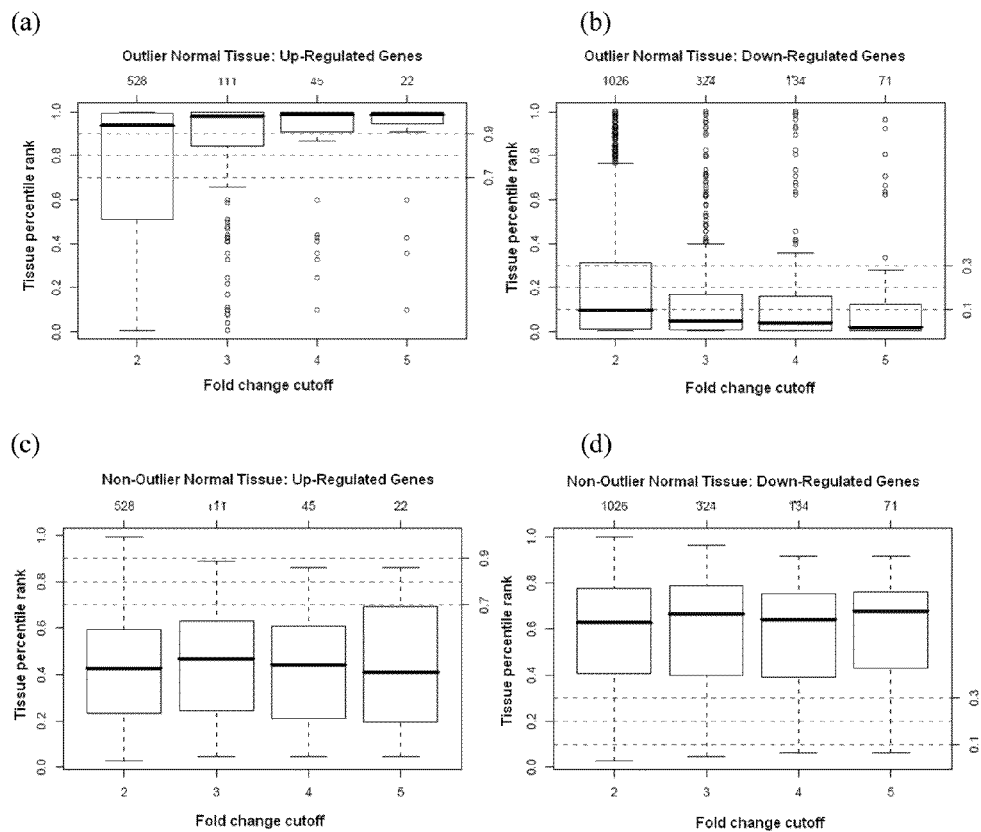
FIG. 2 depicts graphs showing the percentile rank distribution of outlier normal breast tissue versus non-outlier normal breast tissue (as a counter example). Two panels were generated for each tissue. One plot was for up-regulated IDC genes at various fold-change cutoffs and the other one was for down-regulated genes. At each plot, the Y axis represented the tissue percentile rank and the X axis indicated the fold-change cutoff. Number of IDC up-regulated genes ((a) and (c)) or down-regulated genes ((b) and (d)) with a fold-change higher than a cutoff was displayed on the top of the plot (e.g., there were 528 up-regulated IDC genes with a fold greater than 2). Each boxplot displayed distribution of a tissue percentile rank at a specific fold cutoff. For each gene from the 528 genes (fold>2), outlier tissue was ranked among all the histologically normal breast (HNB) tissues to obtain the percentile rank resulting in 528 percentile ranks (corresponding to the 528 genes) to indicate the position of this outlier tissue compared to the rest HNB tissues. (a) Boxplot showed the median of percentile rank for the outlier tissue was beyond 90%. Plots (a) and (b) displayed distribution of percentile rank for the outlier tissue. (b) median of percentile rank was below 20% for the down-regulated genes. The results showed this outlier tissue had higher expression (up or down) than the other normal tissues. (c) Non-outlier tissue gave a different pattern, with a median of percentile rank was around 40%. (d) Median of percentile rank was around 60%.

The inventors have discovered malignancy-risk gene signature that can assess an individual's risk of developing breast cancer. The invention described herein provides methods for determining or predicting the likelihood that an individual who has histologically normal breast tissue will develop breast cancer, have recurrence of breast cancer, and/or for predicting spread of breast cancer by using malignancy-risk gene signatures. The invention also describes malignancy-risk gene signatures that can be used for such determination and arrays/microarrays that comprise these malignancy-risk gene signatures. The invention further provides for kits comprising such arrays/microarrays and computer readable media with such malignancy-risk gene signatures for use in determining if an individual will experience the development of breast cancer, recurrence of breast cancer and/or spread of breast cancer.

DEFINITIONS

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

"Malignancy-risk," "high risk gene signature" and "outlier gene signature" are used interchangeably herein and are used herein to describe gene signatures that can predict if an individual with histologically normal breast tissue is at risk to develop breast cancer, to have recurrence of breast cancer, and/or to have metastasis (i.e., spread) of breast cancer.

As used herein, an individual "at risk" of developing breast cancer may or may not have detectable disease or symptoms of disease, and may or may not have displayed detectable disease or symptoms of disease prior to the treatment methods described herein. "At risk" denotes that a subject has one or more risk factors, which are measurable parameters that correlate with development of breast cancer, as described herein and known in the art. A subject having one or more of these risk factors has a higher probability of developing breast cancer than a subject without one or more of these risk factor(s). For example, in some embodiments, a subject "at risk" of developing breast cancer has a genetic signature comprising one or more of the genes set forth in Table 6. In another embodiment, a subject "at risk" of developing breast cancer has a genetic signature comprising one or more of the genes set forth in Table 3, 7, 8, FIGS. 33B, 34B, 35B and 36A.

"Breast cancer" as used herein refers to malignant, often uncontrolled, growth of cells in the breast. Although breast cancer occurs primarily in females, breast cancer can occur in men. As such, it is to be understood that the invention applies to both females and males.

"Outlier breast tissue" refer to breast tissue that is histologically normal but has a molecular signature that is abnormal and could has the capacity to develop into cancer. Non-limiting methods for determining if a tissue is an outlier tissue is described herein.

An "individual," "subject," or "patient" is a vertebrate. In certain embodiments, the vertebrate is a mammal. Mammals include, but are not limited to, primates (including human and non-human primates) and rodents (e.g., mice and rats). In certain embodiments, a mammal is a human (both female and male).

A "patient" refers to an "individual" who is under the care of a treating physician. In one embodiment, the patient is a female. In another embodiment, the patient is a female who had not been diagnosed with breast cancer. In yet other embodiments, the patient is a female who has been diagnosed with breast cancer but has had surgery to remove the breast cancer tissue.

A "patient subpopulation," and grammatical variations thereof, as used herein, refers to a patient subset characterized as having one or more distinctive measurable and/or identifiable characteristics that distinguishes the patient subset from others in the broader disease category to which it belongs. Such characteristics include disease subcategories (e.g., invasive carcinoma vs. in situ carcinoma), treatment history, etc. In one embodiment, a patient subpopulation is characterized by genetic signatures, including malignancy-risk gene signatures.

The term "sample", as used herein, refers to a composition that is obtained or derived from an individual that contains a cellular and/or other molecular entity that is to be characterized and/or identified, for example based on physical, biochemical, chemical and/or physiological characteristics. In one embodiment, the sample is taken from a breast that is ipsilateral to the breast cancer.

By "tissue or cell sample" is meant a collection of similar cells obtained from a tissue of a subject or patient. The source of the tissue or cell sample may be solid tissue as from a fresh, frozen and/or preserved tissue sample. In one embodiment, the tissue or cell sample may be taken from a breast lumpectomy or mastectomy. The tissue sample may also be primary or cultured cells or cell lines taken from and/or derived from an individual. The tissue sample may contain compounds which are not naturally intermixed with the tissue in nature such as preservatives, anticoagulants, buffers, fixatives, nutrients, antibiotics, or the like.

As used herein, "tissue sample" or "sample" comprising substantially normal histological cells have at least about 50% of the cells in the sample which have normal histological appearance (as determined by one of skill in the art, e.g., a pathologist). In some embodiments, at least about 55% of the cells in the sample which have normal histological appearance. In yet other embodiments, at least about 60%, at least about 65%, at least about 70%, at least about 75%, at least about 80%, at least about 85%, at least about 90%, at least about 95%, at least about 96%, at least about 97%, at least about 98%, at least about 99%, at least about 99.5% of the cells in the sample which have normal histological appearance.

"Pre-pathological" tissue refers to tissue which has a normal histological appearance.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis according to the present invention. It is understood that the present invention comprises a method whereby the same section of tissue sample can be analyzed at both morphological and molecular levels, or can be analyzed with respect to both protein and nucleic acid expression. The examples provided herein where nucleic acid expression is used for predictive purposes are non-limiting examples. It is to be understood that protein expression could also be used for predictive purposes.

As used herein, "array" and "microarray" are interchangeable and refer to an arrangement of a collection of nucleotide sequences in a centralized location. Arrays can be on a solid substrate, such as a glass slide, or on a semi-solid substrate, such as nitrocellulose membrane. The nucleotide sequences can be DNA, RNA, or any permutations thereof. The nucleotide sequences can also be partial sequences from a gene, primers, whole gene sequences, non-coding sequences, coding sequences, published sequences, known sequences, or novel sequences.

The term "polynucleotide" or "nucleic acid," as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, a-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR 2 ("amidate"), P(O)R, P(O)OR', CO or CH 2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, refers to short, single stranded polynucleotides that are at least about seven nucleotides in length and less than about 250 nucleotides in length. Oligonucleotides may be synthetic. The terms "oligonucleotide" and "polynucleotide" are not mutually exclusive. The description above for polynucleotides is equally and fully applicable to oligonucleotides.

The term "primer" refers to a single stranded polynucleotide that is capable of hybridizing to a nucleic acid and allowing the polymerization of a complementary nucleic acid, generally by providing a free 3'-OH group.

"Predicting" and "prediction" as used herein does not mean that the event will happen with 100% certainty. Instead it is intended to mean the event will more likely than not happen. Acts taken to "predict" or "make a prediction" can include the determination of the likelihood that an event will be more likely than not to happen. Assessment of multiple factors described herein can be used to make such determination or prediction.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of gene expression analysis or protocol, one may use the results of the gene expression analysis or protocol to determine whether a specific therapeutic regimen should be performed.

The term "diagnosis" is used herein to refer to the identification or classification of a molecular or pathological state, disease or condition. For example, "diagnosis" may refer to identification of a particular type of breast cancer, e.g., invasive ductal carcinoma (IDC). "Diagnosis" may also refer to the classification of a particular sub-type of breast cancer, e.g., by tissue involvement (e.g., lobular or ductal), by molecular features (e.g., a patient with histologically normal breast tissue).

The term "aiding diagnosis" is used herein to refer to methods that assist in making a clinical determination regarding the presence, degree or other nature, of a particular type of symptom or condition of breast cancer. For example, a method of aiding diagnosis of breast cancer can comprise measuring the amount or detecting the presence or absence of one or more malignancy-risk genes in a biological sample from an individual. In another example, a method of aiding diagnosis of breast cancer can comprise measuring the amount or detecting the presence of one or more malignancy-risk genes in a biological sample from an individual.

The term "prognosis" is used herein to refer to the prediction of the likelihood of the development of breast cancer (including recurrence of breast cancer). The predictive methods of the invention can be used clinically to make treatment decisions by choosing the most appropriate treatment modalities for any particular patient. The predictive methods of the present invention are valuable tools in predicting if and/or aiding in the diagnosis as to whether a patient is likely to develop breast cancer, have recurrence of breast cancer, and/or metastasis of the cancer. Diagnosis of breast cancer may be made according to any protocol that one of skill of art would use, for example, those set by the College of American Pathology.

As used herein, "treatment" refers to clinical intervention in an attempt to alter the natural course of the individual or cell being treated, and can be performed before or during the course of clinical pathology. Desirable effects of treatment include preventing the occurrence or recurrence of a disease or a condition or symptom thereof, alleviating a condition or symptom of the disease, diminishing any direct or indirect pathological consequences of the disease, decreasing the rate of disease progression, ameliorating or palliating the disease state, and achieving remission or improved prognosis. In some embodiments, methods and compositions of the invention are useful in attempts to delay development of a disease or disorder.

A "medicament" is an active drug to treat a disease, disorder, and/or condition. In one embodiment, the disease, disorder, and/or condition is breast cancer or its symptoms or side effects associated with treatment of breast cancer.

Reference to "about" a value or parameter herein includes (and describes) embodiments that are directed to that value or parameter per se. For example, description referring to "about X" includes description of "X."

It is understood that aspect and embodiments of the invention described herein include "consisting" and/or "consisting essentially of" aspects and embodiments.

General Techniques

Unless defined otherwise, technical and scientific terms used herein have the same meaning as commonly understood by one of ordinary skill in the art to which this invention belongs.

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, periodic updates); "PCR: The Polymerase Chain Reaction", (Mullis et al., eds., 1994); Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), and "The Breast" by Copeland Bland.

Primers, oligonucleotides and polynucleotides employed in the present invention can be generated using standard techniques known in the art.

Malignancy-Risk Signature

The invention provides for methods and malignancy-risk gene signatures for predicting the likelihood that an individual with histologically normal breast tissue will develop breast cancer. The invention also provides for methods and malignancy-risk gene signatures for predicting the likelihood that an individual with histologically normal breast tissue will develop a recurrence of breast cancer. The invention further provides for methods and malignancy-risk gene signatures for predicting the likelihood for the spread of breast cancer (e.g., metastasis) in an individual.

Accordingly, the invention provides for methods of using the malignancy-risk gene signatures disclosed here to assess cancer risk, cancer relapse, cancer progression and prognosis. The use of such signatures has significant benefits for the diagnosis and the aiding of diagnosis of an individual who is at risk for developing breast cancer, developing a recurrence of breast cancer and/or metastasis of breast cancer. The knowledge that an individual will likely develop breast cancer enables physicians to take actions which are personalized to treat the patient. In some cases, this involves more careful monitoring and/or testing of the individual. In other cases, it may involve a more aggressive plan of using chemotherapeutic agents or radiation therapy.

The methods and malignancy-risk gene signatures of this invention may be used for any individual in need of such assessment. In other embodiments, the individual is anyone who is at risk of having breast cancer (whether for the first time or recurring breast cancer). In one embodiment, the individual is a patient who has had breast cancer and had some type of treatment to remove or reduce the breast cancer. The treatment can be surgical procedure (e.g., resection, lumpectomy, mastectomy, lymph node dissection) alone or with some type of cancer therapy (e.g., chemotherapy, radiation therapy, hormone therapy, and/or targeted therapy like Herceptin®). The individual may have had just cancer therapy alone. In one embodiment, the individual appears to have had all the breast cancer removed and the tissue adjacent to the cancer (i.e., ipsilateral to the cancer) is histologically normal.

In another embodiment, methods and malignancy-risk gene signatures of this invention may be used for an individual who has not been diagnosed with breast cancer but has a family history of breast cancer. The individual is a vertebrate. In certain embodiments, the vertebrate is a mammal. Mammals include, but are not limited to, primates (including human and non-human primates) and rodents (e.g., mice and rats). In certain embodiments, a mammal is a human. In one embodiment, the individual is female. In another embodiment, the individual is a male. In some cases, the individual is a "patient" who is under the care of a treating physician.

In some cases, a patient subpopulation is first determined before determining the likelihood of those patients developing cancer. In one aspect, the patient subpopulation is comprises of females who have histologically normal tissue in one or both breasts. In some cases, the patient subpopulation is further subdivided by their medical history, such as what type of breast cancer they had (e.g., lobular vs. ductal, invasive carcinoma vs. in situ carcinoma), or the severity of the cancer. In other cases, the patients are further subdivided by their treatment history, etc. In one embodiment, a patient subpopulation is characterized by genetic signatures, including malignancy-risk gene signatures. The patient subpopulation can express at least about 10 malignancy-risk genes from the malignancy-risk gene signatures disclosed herein (e.g., from Table 6). In one embodiment, the patient subpopulation expresses at least about 15 malignancy-risk genes, at least about 20 malignancy-risk genes, at least about 25 malignancy-risk genes, at least about 30 malignancy-risk genes, at least about 35 malignancy-risk genes, at least about 40 malignancy-risk genes, at least about 45 malignancy-risk genes, at least about 50 malignancy-risk genes, at least about 55 malignancy-risk genes, at least about 60 malignancy-risk genes, at least about 70 malignancy-risk genes, at least about 75 malignancy-risk genes, at least about 80 malignancy-risk genes, at least about 85 malignancy-risk genes, at least about 90 malignancy-risk genes, at least about 95 malignancy-risk genes, at least about 100 malignancy-risk genes, at least about 105 malignancy-risk genes, at least about 110 malignancy-risk genes, at least about 115 malignancy-risk genes, at least about 120 malignancy-risk genes, at least about 125 malignancy-risk genes, at least about 130 malignancy-risk genes, at least about 135 malignancy-risk genes, or at least about 140 malignancy-risk genes.

Identification of Malignancy-Risk Signature

Figure 23:
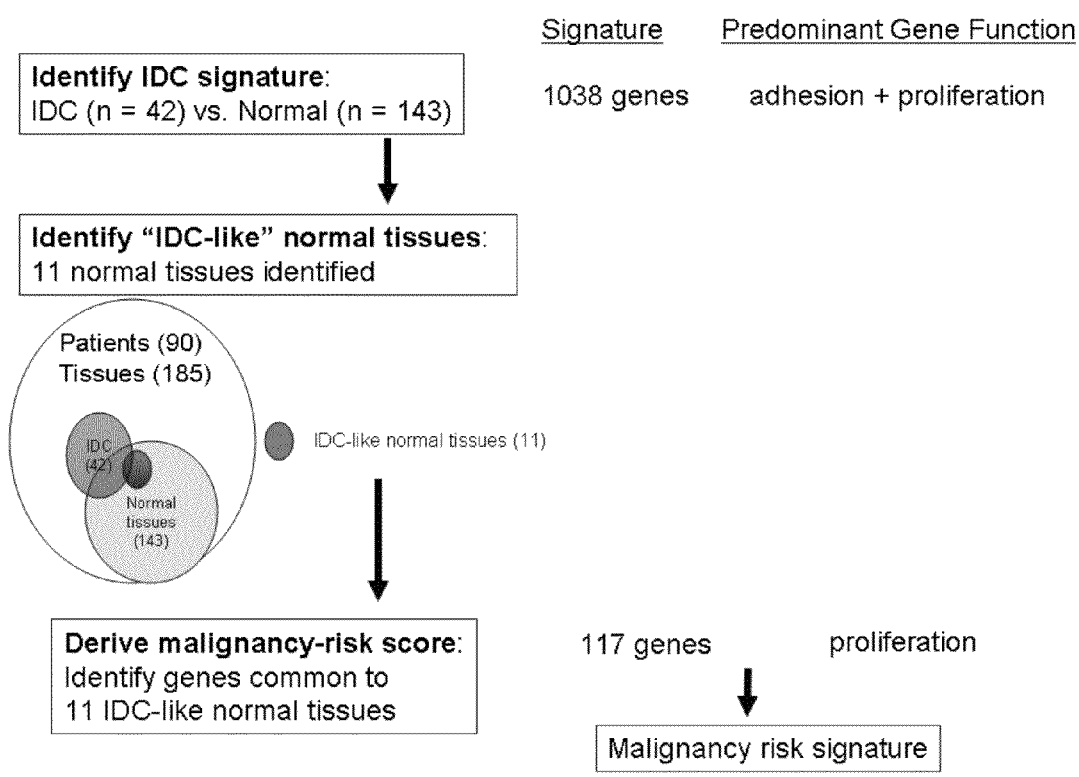
FIG. 23 is a flow chart to developing the malignancy-risk gene signature.

Identification of malignancy-risk gene signatures is detailed in the Examples section. See, for example, FIG. 23 for a flow chart. Such malignancy-risk gene signatures can be obtained by determining an IDC (invasive ductal carcinoma) signature by comparing the gene expression profiles from IDC patients to that of normal histological tissue adjacent to breast cancer in patients who have had cancer and had some type of procedure (e.g., surgical or cancer therapy) to remove the breast cancer. Statistical analysis as described in the Examples can then be performed to identify "IDC-like genes" (see, e.g., Example 13) from which malignancy-risk scores can be calculated (see, e.g., Example 13) and a malignancy-risk gene signature is then obtained. The 140 malignancy-risk genes are disclosed in Table 6.

Malignancy-risk genes can be cell proliferation genes, however, not all cell proliferation genes are malignancy-risk genes. Others are involved in cell adhesion, cell mitosis, DNA replication. The Figures and Tables further describe the malignancy-risk genes and their pathway roles.

Accordingly, in one embodiment, the invention encompasses methods of using the malignancy-risk genes of Table 6 to predict an individual's likelihood of developing breast cancer, having recurrent breast cancer or to have metastasis of breast cancer. In other embodiments, the invention encompasses the use of such this malignancy-risk gene signature to assess an individual's risk of developing or having recurring breast cancer and/or metastasis. In some embodiments, at least about 10 genes from the 140 malignancy-risk genes in Table 6 are used for this determination. In other embodiments, at least about 15 malignancy-risk genes are used. In yet other embodiments, at least about 20 malignancy-risk genes, at least about 25 malignancy-risk genes, at least about 30 malignancy-risk genes, at least about 35 malignancy-risk genes, at least about 40 malignancy-risk genes, at least about 45 malignancy-risk genes, at least about 50 malignancy-risk genes, at least about 55 malignancy-risk genes, at least about 60 malignancy-risk genes, at least about 70 malignancy-risk genes, at least about 75 malignancy-risk genes, at least about 80 malignancy-risk genes, at least about 85 malignancy-risk genes, at least about 90 malignancy-risk genes, at least about 95 malignancy-risk genes, at least about 100 malignancy-risk genes, at least about 105 malignancy-risk genes, at least about 110 malignancy-risk genes, at least about 115 malignancy-risk genes, at least about 120 malignancy-risk genes, at least about 125 malignancy-risk genes, at least about 130 malignancy-risk genes, or at least about 135 malignancy-risk genes are used to make these determinations of risk of developing breast cancer, having recurrent breast cancer or to have metastasis of breast cancer.

The invention also provides for methods for using the malignancy-risk genes of Table 3 to predict an individual's likelihood of developing breast cancer, having recurrent breast cancer or to have metastasis of breast cancer. In other embodiments, the invention encompasses the use of such this malignancy-risk gene signature to assess an individual's risk of developing or having recurring breast cancer and/or metastasis. In some embodiments, at least about 5 genes from the malignancy-risk genes in Table 3 are used for this determination. In other embodiments, at least about 6, 7, 8, 9, or 10 malignancy-risk genes are used. In yet other embodiments, at least about 11, 12, 13, 14, 15, 16, 17, 18, 19, or 20 malignancy-risk genes are used. In yet other embodiments, at least about 21, 22, 23, 24, 25, 26, 27, 28, 29, or 30 malignancy-risk genes are used.

In another embodiment, the invention encompasses the malignancy-risk gene signature of Table 3 wherein the gene signature does not include at least about 1 gene selected from the genes listed in FIGS. 31A, 32B, 33A, and 35A. In other embodiments, the invention encompasses the malignancy-risk gene signature of Table 3 wherein the gene signature does not include at least about 2, 3, 4, 5, 6, 7, 8, 9, or 10 genes selected from the genes listed in FIGS. 31A, 32B, 33A, and 35A. In other embodiments, the invention encompasses the malignancy-risk gene signature of Table 3 wherein the gene signature does not include at least about 15, 20, 30 or more genes selected from the genes listed in FIGS. 31A, 32B, 33A, and 35A.

In another aspect of the invention, the invention provides for a malignancy-risk gene signature which comprises at least about 10 genes selected from the group consisting of the genes in Table 3, Table 7, Table 8, FIG. 34B, FIG. 35B, and FIG. 36A. In another embodiment of the invention, the invention provides for a malignancy-risk gene signature which comprises at least about 20, 25, 30, 35, 40, 50 or more genes selected from the group consisting of the genes in Table 3, Table 7, Table 8, FIG. 33B, FIG. 34B, FIG. 35B, and FIG. 36A.

In other embodiments, each of the following genes: topoisomerase-2, Bub-1 and MDM-2, can be used as a predictor of developing breast cancer, having recurrent breast cancer or to have metastasis of breast cancer.

In another embodiment, the malignancy-risk signature is at least one or more genes selected from the group consisting of the following genes from Table 6: APOBEC3B, C6orf115, CASC5, CORO2A, FAM83D, HIST1H2BF, MOBK1B, WDSOF1, IQGAP3, AMOTL2, CCDC50, CHRDL1, GPRASP1, MAGI2, RBMS3, SYNPO2, Affymetrix probe set id 213158_at, Affymetrix probe set id 226250_at, Affymetrix probe set id 226252_at, Affymetrix probe set id 227082_at, Affymetrix probe set id 227121_at, Affymetrix probe set id 227646_at, Affymetrix probe set id 227719_at, Affymetrix probe set id 235556_at, Affymetrix probe set id 235570_at, and Affymetrix probe set id 243584_at.

In another embodiment, the malignancy-risk signature is at least about 2, 3, 4, 5, 6, 7, 8, 9, 10, 11, 12, 13, 14 or 15 more genes selected from the group consisting of the following genes from Table 6: APOBEC3B, C6orf115, CASC5, CORO2A, FAM83D, HIST1H2BF, MOBK1B, WDSOF1, IQGAP3, AMOTL2, CCDC50, CHRDL1, GPRASP1, MAGI2, RBMS3, SYNPO2, Affymetrix probe set id 213158_at, Affymetrix probe set id 226250_at, Affymetrix probe set id 226252_at, Affymetrix probe set id 227082_at, Affymetrix probe set id 227121_at, Affymetrix probe set id 227646_at, Affymetrix probe set id 227719_at, Affymetrix probe set id 235556_at, Affymetrix probe set id 235570_at, and Affymetrix probe set id 243584_at.

The malignancy-risk gene signature can also be at least one or more of the malignancy-risk genes listed in Table 7. In another embodiment, the malignancy-risk signature is at least about 2, 3, 4, 5, 6, 7, 8, 9, 10, 11, 12, 13, 14 or 15 more genes selected from the genes of Table 7. In another embodiment, the malignancy-risk signature is at least about 20, 25, 30 or 35 or more genes selected from the genes of Table 7.

The malignancy-risk gene signature can also be at least one or more of the malignancy-risk genes listed in Table 8. In another embodiment, the malignancy-risk signature is at least about 2, 3, 4, 5, 6, 7, 8, 9, 10, 11, 12, 13, 14 or 15 more genes selected from the genes of Table 8. In another embodiment, the malignancy-risk signature is at least about 16, 17, 18, 19, 20, 21, 22, 23, 24 or more genes selected from the genes of Table 8.

In one aspect, the malignancy-risk gene signature does not include at least one of the genes in FIG. 31A. In other embodiments, the malignancy-risk gene signature does not include at least about 2, 3, 4, 5, 6, 7, 8, 9, 10, 11, 12, 13, 14 or 15 or more of the genes in FIG. 31A.

Figures 32A, 32B:
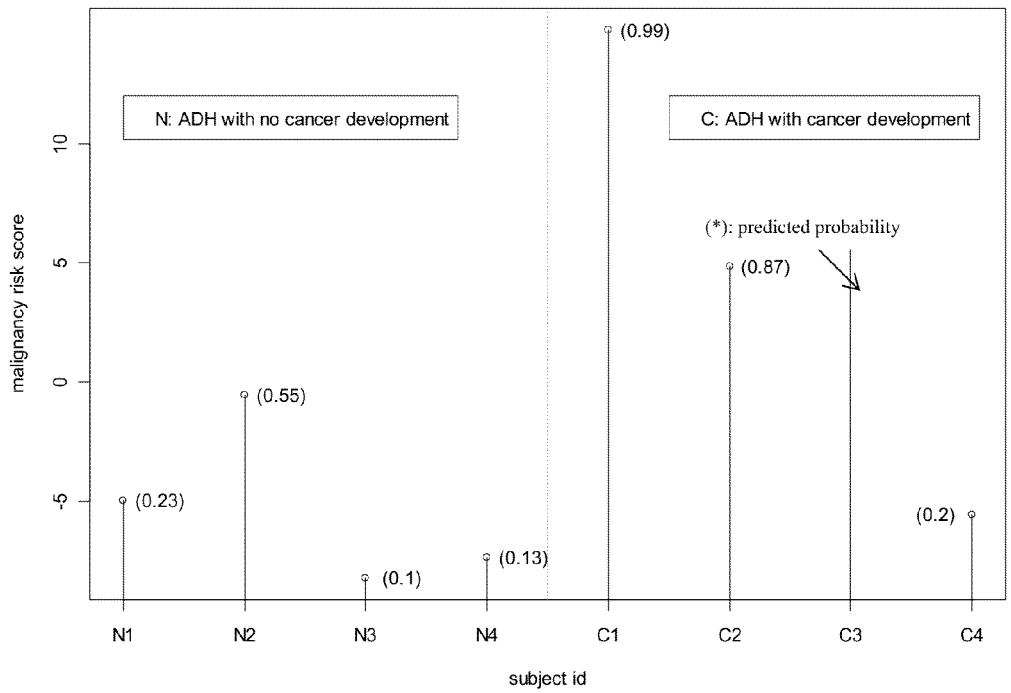
FIG. 32A is a graph of the assessment of cancer risk in ADH patients using the malignancy-risk gene signature.
FIG. 32B is a list of malignancy-risk genes with p value <0.05.

In one aspect, the malignancy-risk gene signature does not include at least about one of the genes in FIG. 32B. In other embodiments, the malignancy-risk gene signature does not include at least about 2, 3, 4, 5, 6, 7, 8, 9, 10, 11, 12, 13, 14 or 15 or more of the genes in FIG. 32B.

In one aspect, the malignancy-risk gene signature does not include at least about one of the genes in FIG. 33A. In other embodiments, the malignancy-risk gene signature does not include at least about 2, 3, 4, 5, 6 or more of the genes in FIG. 33A.

In another aspect, the malignancy-risk gene signature can also be at least about one or more of the genes in FIG. 33B. In another embodiment, the malignancy-risk signature is at least about 2, 3, 4, 5, 6, 7, 8, 9, 10, 11, 12, 13, 14 or 15 more genes selected from the genes of FIG. 33B. In another embodiment, the malignancy-risk signature is at least about 16, 17, 18, 19, 20, 21, 22, 23, 24, 25, 30, 35, 40, 45 or more genes selected from the genes of FIG. 33B.

In another aspect, the malignancy-risk gene signature can also be at least about one or more of the genes in FIG. 34B. In another embodiment, the malignancy-risk signature is at least about 2, 3, 4, 5, 6, 7, 8, 9, 10, 11, 12, 13, 14 or 15 more genes selected from the genes of FIG. 34B. In another embodiment, the malignancy-risk signature is at least about 16, 17, 18, 19, 20, 21, 22, 23, 24, 25, 30, 35, 40, 45, 47 or more genes selected from the genes of FIG. 34B.

In one aspect, the malignancy-risk gene signature does not include at least about one of the genes in FIG. 35A. In other embodiments, the malignancy-risk gene signature does not include at least about 2, 3, or 4 of the genes in FIG. 35A.

In another aspect, the malignancy-risk gene signature can also be at least about one or more of the genes in FIG. 35B. In another embodiment, the malignancy-risk signature is at least about 2, 3, 4, 5, 6, 7, 8, 9, 10, 11, 12, 13, 14 or 15 more genes selected from the genes of FIG. 35B. In another embodiment, the malignancy-risk signature is at least about 16, 17, 18, 19, 20, 21, 22, 23, 24, 25, 30, 35, 40, 45, 50, 55, 60, 62 or more genes selected from the genes of FIG. 35B.

In another aspect, the malignancy-risk gene signature can also be at least about one or more of the genes in FIG. 36A. In another embodiment, the malignancy-risk signature is at least about 2, 3, 4, 5, 6, 7, 8, 9, 10, 11, 12, 13, 14 or 15 more genes selected from the genes of FIG. 36A. In another embodiment, the malignancy-risk signature is at least about 16, 17, 18, 19, 20, 21, 22, 23, 24, 25, 30, 32 or more genes selected from the genes of FIG. 36A.

The invention also comprises methods of identifying additional malignancy-risk genes and those additional malignancy-risk genes for inclusion in the malignancy-risk gene signature by using the methology described herein.

Arrays and Gene Chips and Kits Comprising Thereof

Arrays and microarrays which contain the malignancy-risk gene signatures as described herein for assessing the likelihood of developing cancer, cancer relapse, cancer progression, prognosis, and/or metastasis are also encompassed within the scope of this invention. Methods of making arrays are well-known in the art and as such, do not need to be described in detail here.

Such arrays can contain the profiles of at least about 5, 10, 15, 20, 25, 30, 35, 40, 45, 50, 55, 60, 65, 70, 75, 80, 85, 90, 95, 100, 105, 110, 115, 120, 125, 130, 135, or 140 genes as disclosed in the Figures and Tables. Accordingly, arrays for assessing the likelihood of developing cancer, cancer relapse, cancer progression, and/or metastasis can be customized for prognosis, diagnosis, aiding in the diagnosis or treatment of breast cancer. The array can be packaged as part of kit comprising the customized array itself and a set of instructions for how to use the array to determine an individual's likelihood of developing cancer, cancer relapse, cancer progression, and metastasis.

Also provided are reagents and kits thereof for practicing one or more of the above described methods. The subject reagents and kits thereof may vary greatly. Reagents of interest include reagents specifically designed for use in production of the above described malignancy-risk gene signatures.

One type of such reagent is an array probe of nucleic acids, such as a DNA chip, in which the malignancy-risk gene signatures are represented. A variety of different array formats are known in the art, with a wide variety of different probe structures, substrate compositions and attachment technologies. Representative array structures of interest include those described in U.S. Pat. Nos. 5,143,854; 5,288, 644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. It is to be understood that the invention also encompasses detection of protein expression of the malignancy-risk genes as described herein. Detection of protein expression is known to one of skill in the art and may be done using any number of commercially available products.

The DNA chip is convenient to compare the expression levels of a number of genes at the same time. DNA chip-based expression profiling can be carried out, for example, by the method as disclosed in "Microarray Biochip Technology" (Mark Schena, Eaton Publishing, 2000). A DNA chip comprises immobilized high-density probes to detect a number of genes. Thus, the expression levels of many genes can be estimated at the same time by a single-round analysis. Namely, the expression profile of a specimen can be determined with a DNA chip. A DNA chip may comprise probes, which have been spotted thereon, to detect the expression level of the malignancy-risk gene signatures of the present invention.

A probe may be designed for each malignancy-risk gene selected, and spotted on a DNA chip. Such a probe may be, for example, an oligonucleotide comprising 5-50 nucleotide residues. A method for synthesizing such oligonucleotides on a DNA chip is known to those skilled in the art. Longer DNAs can be synthesized by PCR or chemically. A method for spotting long DNA, which is synthesized by PCR or the like, onto a glass slide is also known to those skilled in the art. A DNA chip that is obtained by the method as described above can be used to determine the likelihood that an individual will develop breast disease, develop breast cancer, have recurrence of breast cancer, and/or have metastasis of breast cancer according to the present invention.

DNA microarray and methods of analyzing data from microarrays are well-described in the art, including in *DNA Microarrays: A Molecular Cloning Manual*, Ed. by Bowtel and Sambrook (Cold Spring Harbor Laboratory Press, 2002);

*Microarrays for an Integrative Genomics* by Kohana (MIT Press, 2002); *A Biologist's Guide to Analysis of DNA Microarray Data*, by Knudsen (Wiley, John & Sons, Incorporated, 2002); *DNA Microarrays: A Practical Approach*, Vol. 205 by Schema (Oxford University Press, 1999); and *Methods of Microarray Data Analysis II*, ed. by Lin et al. (Kluwer Academic Publishers, 2002).

One aspect of the invention provides a gene chip having a plurality of different oligonucleotides attached to a first surface of the solid support and having specificity for a plurality of genes, wherein at least about 50% of the genes are common to those of the malignancy-risk genes in Table 6. In one embodiment, at least about 70%, 80%, 90% or 95% of the genes in the gene chip are common to those of the malignancy-risk genes in Table 6.

In another aspect of the invention, the invention provides a gene chip having a plurality of different oligonucleotides attached to a first surface of the solid support and having specificity for a plurality of genes, wherein at least about 50% of the genes are common to those of the malignancy-risk genes in Table 3. In one embodiment, at least about 70%, 80%, 90% or 95% of the genes in the gene chip are common to those of the malignancy-risk genes in Table 3.

In another aspect of the invention, the invention provides a gene chip having a plurality of different oligonucleotides attached to a first surface of the solid support and having specificity for a plurality of genes, wherein at least about 50% of the genes are common to those of the malignancy-risk genes in Table 7. In one embodiment, at least about 70%, 80%, 90% or 95% of the genes in the gene chip are common to those of the malignancy-risk genes in Table 7.

In another aspect of the invention, the invention provides a gene chip having a plurality of different oligonucleotides attached to a first surface of the solid support and having specificity for a plurality of genes, wherein at least about 50% of the genes are common to those of the malignancy-risk genes in Table 8. In one embodiment, at least about 70%, 80%, 90% or 95% of the genes in the gene chip are common to those of the malignancy-risk genes in Table 8.

In another aspect of the invention, the invention provides a gene chip having a plurality of different oligonucleotides attached to a first surface of the solid support and having specificity for a plurality of genes, wherein at least about 50% of the genes are common to those of the malignancy-risk genes in FIG. 33B, 34B, 35B, or 36A. In one embodiment, at least about 70%, 80%, 90% or 95% of the genes in the gene chip are common to those of the malignancy-risk genes in FIG. 33B, 34B, 35B, or 36A.

In another aspect of the invention, the invention provides a gene chip having a plurality of different oligonucleotides attached to a first surface of the solid support and having specificity for a plurality of genes, wherein at least about 50% of the genes are common to those of the malignancy-risk genes in Table 6 but does not include at least about one of the genes in FIG. 31A. In one embodiment, at least about 70%, 80%, 90% or 95% of the genes in the gene chip are common to those of the malignancy-risk genes in Table 6 but does not include at least about one of the genes in FIG. 31A. In other embodiments, the gene chip includes at least about 70%, 80%, 90% or 95% of the genes in the gene chip are common to those of the malignancy-risk genes in Table 6 but does not include at least about 2, 3, 4, 5, 6, 7, 8, 9, 10, 11, 12, 13, 14 or 15 or more of the genes in FIG. 31A.

In another aspect, the invention provides a gene chip having a plurality of different oligonucleotides attached to a first surface of the solid support and having specificity for a plurality of genes, wherein at least about 50% of the genes are common to those of the malignancy-risk genes in Table 6 but does not include at least about one of the genes in FIG. 32B. In other embodiments, the malignancy-risk gene signature does not include at least about 2, 3, 4, 5, 6, 7, 8, 9, 10, 11, 12, 13, 14 or 15 or more of the genes in FIG. 32B.

In another aspect, the invention provides a gene chip having a plurality of different oligonucleotides attached to a first surface of the solid support and having specificity for a plurality of genes, wherein at least about 50% of the genes are common to those of the malignancy-risk genes in Table 6 but does not include at least about one of the genes in FIG. 33A. In other embodiments, the malignancy-risk gene signature does not include at least about 2, 3, 4, 5, 6 or more of the genes in FIG. 33A.

In one aspect, the gene chip comprises at least about 10 genes from the 140 malignancy-risk genes in Table 6. In other embodiments, the gene chip comprises at least about 15, 20, 25, 30, 35, 40, 45, 50, 55, 60, 70, 75, 80, 85, 90, 95, 100, 105, 110, 115, 120, 125, 130, 135 or more malignancy-risk genes are used to make these determinations of risk of developing breast cancer, having recurrent breast cancer or to have metastasis of breast cancer.

In another aspect, the gene chip comprises at least about 10 genes selected from the list consisting of: APOBEC3B, C6orf115, CASC5, CORO2A, FAM83D, HIST1H2BF, MOBK1B, WDSOF1, IQGAP3, AMOTL2, CCDC50, CHRDL1, GPRASP1, MAGI2, RBMS3, SYNPO2, Affymetrix probe set id 213158_at, Affymetrix probe set id 226250_at, Affymetrix probe set id 226252_at, Affymetrix probe set id 227082_at, Affymetrix probe set id 227121_at, Affymetrix probe set id 227646_at, Affymetrix probe set id 227719_at, Affymetrix probe set id 235556_at, Affymetrix probe set id 235570_at, and Affymetrix probe set id 243584_at. In other embodiments, the gene chip comprises at least about 15, 20, 25, or more selected from the list consisting of: APOBEC3B, C6orf115, CASC5, CORO2A, FAM83D, HIST1H2BF, MOBK1B, WDSOF1, IQGAP3, AMOTL2, CCDC50, CHRDL1, GPRASP1, MAGI2, RBMS3, SYNPO2, Affymetrix probe set id 213158_at, Affymetrix probe set id 226250_at, Affymetrix probe set id 226252_at, Affymetrix probe set id 227082_at, Affymetrix probe set id 227121_at, Affymetrix probe set id 227646_at, Affymetrix probe set id 227719_at, Affymetrix probe set id 235556_at, Affymetrix probe set id 235570_at, and Affymetrix probe set id 243584_at. In another embodiment, the gene chip comprises all of the following genes: the list consisting of: APOBEC3B, C6orf115, CASC5, CORO2A, FAM83D, HIST1H2BF, MOBK1B, WDSOF1, IQGAP3, AMOTL2, CCDC50, CHRDL1, GPRASP1, MAGI2, RBMS3, SYNPO2, Affymetrix probe set id 213158_at, Affymetrix probe set id 226250_at, Affymetrix probe set id 226252_at, Affymetrix probe set id 227082_at, Affymetrix probe set id 227121_at, Affymetrix probe set id 227646_at, Affymetrix probe set id 227719_at, Affymetrix probe set id 235556_at, Affymetrix probe set id 235570_at, and Affymetrix probe set id 243584_at.

One aspect of the invention provides a kit comprising: (a) any of the gene chips described herein; and (b) one of the computer-readable mediums described herein.

In some embodiments, the arrays include probes for at least about 2, 3, 4, 5, 6, 7, 8, 9, 10, 15, 20, 25, 30, 40, 50, 60, 70, 80, 90, 100, 110, 120, 130, or 140 of the genes listed in Table 3, Table 6, Table 7, Table 8, FIG. 33B, FIG. 34B, FIG. 35B, and/or FIG. 36A. Where the subject arrays include probes for additional genes not listed in the tables, in certain embodiments the number % of additional genes that are represented does not exceed about 50%, 40%, 30%, 20%, 15%, 10%, 8%, 6%, 5%, 4%, 3%, 2% or 1%.

The kits of the subject invention may include the above described arrays. The kits may further include one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

In addition to the above components, the kits will further include instructions for practicing the methods and arrays described herein. These instructions may be present in the kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Computer Readable Media Comprising Gene Expression Profiles

The invention also contemplates computer readable media that comprises malignancy-risk gene signatures. Such media can contain all of part of the malignancy-risk gene signatures of the genes listed in Table 3, Table 6, Table 7, Table 8, FIG. 33B, FIG. 34B, FIG. 35B, and/or FIG. 36A. The media can be a list of the genes or contain the raw data for running a user's own statistical calculation, such as the methods disclosed herein.

Program Products/Systems

Another aspect of the invention provides a program product (i.e., software product) for use in a computer device that executes program instructions recorded in a computer-readable medium to perform one or more steps of the methods described herein, such for assessing the likelihood that an individual will develop breast cancer, have recurrence of breast cancer, and/or metastasis.

On aspect of the invention provides a computer readable medium having computer readable program codes embodied therein, the computer readable medium program codes performing one or more of the following functions: defining the value of one or more risk values from the expression levels genes; calculating the risk of developing breast cancer, calculating the risk of developing breast cancer recurrence, and calculating the risk of developing metastasis.

Another related aspect of the invention provides kits comprising the program product or the computer readable medium, optionally with a computer system. On aspect of the invention provides a system, the system comprising: a computer; a computer readable medium, operatively coupled to the computer, the computer readable medium program codes performing one or more of the following functions: defining the value of one or more risk value from the expression levels genes; calculating the risk of developing breast cancer, calculating the risk of developing breast cancer recurrence, and calculating the risk of developing metastasis.

In one embodiment, the program product comprises: a recordable medium; and a plurality of computer-readable instructions executable by the computer device to analyze data from the array hybridization steps, to transmit array hybridization from one location to another, or to evaluate genome-wide location data between two or more genomes. Computer readable media include, but are not limited to, CD-ROM disks (CD-R, CD-RW), DVD-RAM disks, DVD-RW disks, floppy disks and magnetic tape.

A related aspect of the invention provides kits comprising the program products described herein. The kits may also optionally contain paper and/or computer-readable format instructions and/or information, such as, but not limited to, information on DNA microarrays, on tutorials, on experimental procedures, on reagents, on related products, on available experimental data, on using kits, on chemotherapeutic agents including there toxicity, and on other information. The kits optionally also contain in paper and/or computer-readable format information on minimum hardware requirements and instructions for running and/or installing the software. The kits optionally also include, in a paper and/or computer readable format, information on the manufacturers, warranty information, availability of additional software, technical services information, and purchasing information. The kits optionally include a video or other viewable medium or a link to a viewable format on the internet or a network that depicts the use of the use of the software, and/or use of the kits.

The analysis of data, as well as the transmission of data steps, can be implemented by the use of one or more computer systems. Computer systems are readily available. The processing that provides the displaying and analysis of image data for example, can be performed on multiple computers or can be performed by a single, integrated computer or any variation thereof. For example, each computer operates under control of a central processor unit (CPU), such as a "Pentium" microprocessor and associated integrated circuit chips, available from Intel Corporation of Santa Clara, Calif., USA. A computer user can input commands and data from a keyboard and display mouse and can view inputs and computer output at a display. The display is typically a video monitor or flat panel display device. The computer also includes a direct access storage device (DASD), such as a fixed hard disk drive. The memory typically includes volatile semiconductor random access memory (RAM).

Each computer typically includes a program product reader that accepts a program product storage device from which the program product reader can read data (and to which it can optionally write data). The program product reader can include, for example, a disk drive, and the program product storage device can include a removable storage medium such as, for example, a magnetic floppy disk, an optical CD-ROM disc, a CD-R disc, a CD-RW disc and a DVD data disc. If desired, computers can be connected so they can communicate with each other, and with other connected computers, over a network. Each computer can communicate with the other connected computers over the network through a network interface that permits communication over a connection between the network and the computer.

The computer operates under control of programming steps that are temporarily stored in the memory in accordance with conventional computer construction. When the programming steps are executed by the CPU, the pertinent system components perform their respective functions. Thus, the programming steps implement the functionality of the system as described above. The programming steps can be received from the DASD, through the program product reader or through the network connection. The storage drive can receive a program product, read programming steps recorded thereon, and transfer the programming steps into the memory for execution by the CPU. As noted above, the program product storage device can include any one of multiple removable media having recorded computer-readable instructions, including magnetic floppy disks and CD-ROM storage discs. Other suitable program product storage devices can include magnetic tape and semiconductor memory chips. In this way, the processing steps necessary for operation can be embodied on a program product.

Alternatively, the program steps can be received into the operating memory over the network. In the network method, the computer receives data including program steps into the memory through the network interface after network communication has been established over the network connection by well known methods understood by those skilled in the art. The computer that implements the client side processing, and the computer that implements the server side processing or any other computer device of the system, can include any conventional computer suitable for implementing the functionality described herein.

It will be apparent to those of ordinary skill in the art that methods involved in the present invention may be embodied in a computer program product that includes a computer usable and/or readable medium. For example, such a computer usable medium may consist of a read only memory device, such as a CD ROM disk or conventional ROM devices, or a random access memory, such as a hard drive device or a computer diskette, having a computer readable program code stored thereon.

The following examples are provided to illustrate aspects of the invention but are not intended to limit the invention in any manner.

EXAMPLES

Example 1

Materials and Methods

Tissue Collection

Tissues were collected in accordance with the protocols approved by the Institutional Review Board of the University of South Florida, and stored in the tissue bank of Moffitt Cancer Center. Breast tissues from patients that underwent mastectomy at various stages of breast carcinoma were collected and frozen in liquid nitrogen. The tissues were embedded in Tissue-Tek® O.C.T., 5-μm sections cut and mounted on Mercedes Platinum StarFrost™ Adhesive slides. The slides were stained using a standard H&E protocol, and tissue boundaries marked. Using the marked slide as a "map", tissues were microdissected. Adipose tissues were trimmed away; the tumor and "normal" tissues were separated and stored in liquid nitrogen.

Histology

Histological examination of all tissue sections and microdissection of samples were conducted by pathologist to ensure consistency in the clinical diagnoses. From a large invasive breast cancer database, a set of 42 histologically invasive ductal carcinomas (IDC) were identified with various histologic grades (the modified Bloom and Richardson grading[17]). In addition to 42 IDCs, 143 'histologically normal breast' tissues were selected which were free of any other breast lesions.

RNA Extraction

Total RNA was extracted from breast tissues using the Trizol method. Briefly, tissues were ground in liquid nitrogen, resuspended in 5 ml of lysis buffer and incubated for 3 min. at room temperature and centrifuged at 11,500 g for 15 minutes at 4°. The aqueous phase was removed and put into another tube with 2.5 ml of isopropanol, mixed well and set at −20° C. for 20 minutes. DNA was pelleted by centrifuging at 11,500 g for 10 minutes at 4° C. The pellet was washed with 75% ethanol and resuspended in 100 μl of deionized water. The amount of RNA was quantitated by measuring $A_{260}$.

Statistical Methods

Statistical analysis was done by performing a comparison of normal breast and IDC tissues to develop IDC gene signature. Outlier tissues (potential high risk normal breast tissue) were then identified from the normal breast tissue using the IDC gene signature and used to develop outlier gene signature from the outlier tissues. A pathway analysis was performed for IDC and outlier gene signatures to demonstrate the uniqueness of the outlier gene signature. Finally, the outlier gene signature was validated regarding the features of cancer risk prediction, disease progression, and prognosis, in a series of external gene expression datasets for breast cancer.

Briefly, in the first step, Statistical Analysis of Microarray (SAM') was used to develop IDC gene signature which discriminates between the normal and IDC tissues. In the second step, this IDC gene signature was used as reference and applied the outlier tissue approach (OTA) to identify histologically normal breast tissues that had acquired the molecular fingerprint of IDC, and these tissues are referred to as outlier normal tissues to reflect their potential risk for tumor development. The OTA ranks all the normal tissues for each gene. If a normal tissue has its percentile rank over 80% for a majority of up-regulated genes (and/or below 20% for most down-regulated genes), it was considered an outlier normal tissue. An outlier normal tissue tends to show higher level of expression of these genes (up- or down-regulated) and greater likelihood of cancer development. In the third step, once outlier normal tissues were identified, a percentile rank approach was used to find a common set of genes, "outlier genes". Specifically, genes with expression percentile rank of greater than 80% (or less than 20%) in most outlier normal tissues were selected as outlier genes. Pathway analysis was done using MetaCore™ by GeneGo in the step 4. The validation step (step 5) was implemented by first identifying overlapped outlier genes, and then performing principal component analysis (PCA) for prediction.

Example 2

IDC Gene Signature

An IDC gene signature (1,554 probe sets: 1038 unique genes) was first developed from a set of 42 IDC and 143 normal breast tissues. This analysis was done using Statistical Analysis of Microarray[7] and based on a cutoff of false discovery rate (FDR) <0.01 and a fold change >2. Pathway analysis revealed two predominant cellular processes: cell cycle and cell adhesion, as seen in FIG. 1. There were 10 cell adhesion pathways and 7 cell cycle pathways with a significant p-value <0.01. A majority of the genes were down-regulated in the cell adhesion, but up-regulated in the cell cycle.

Example 3

Figure 3:
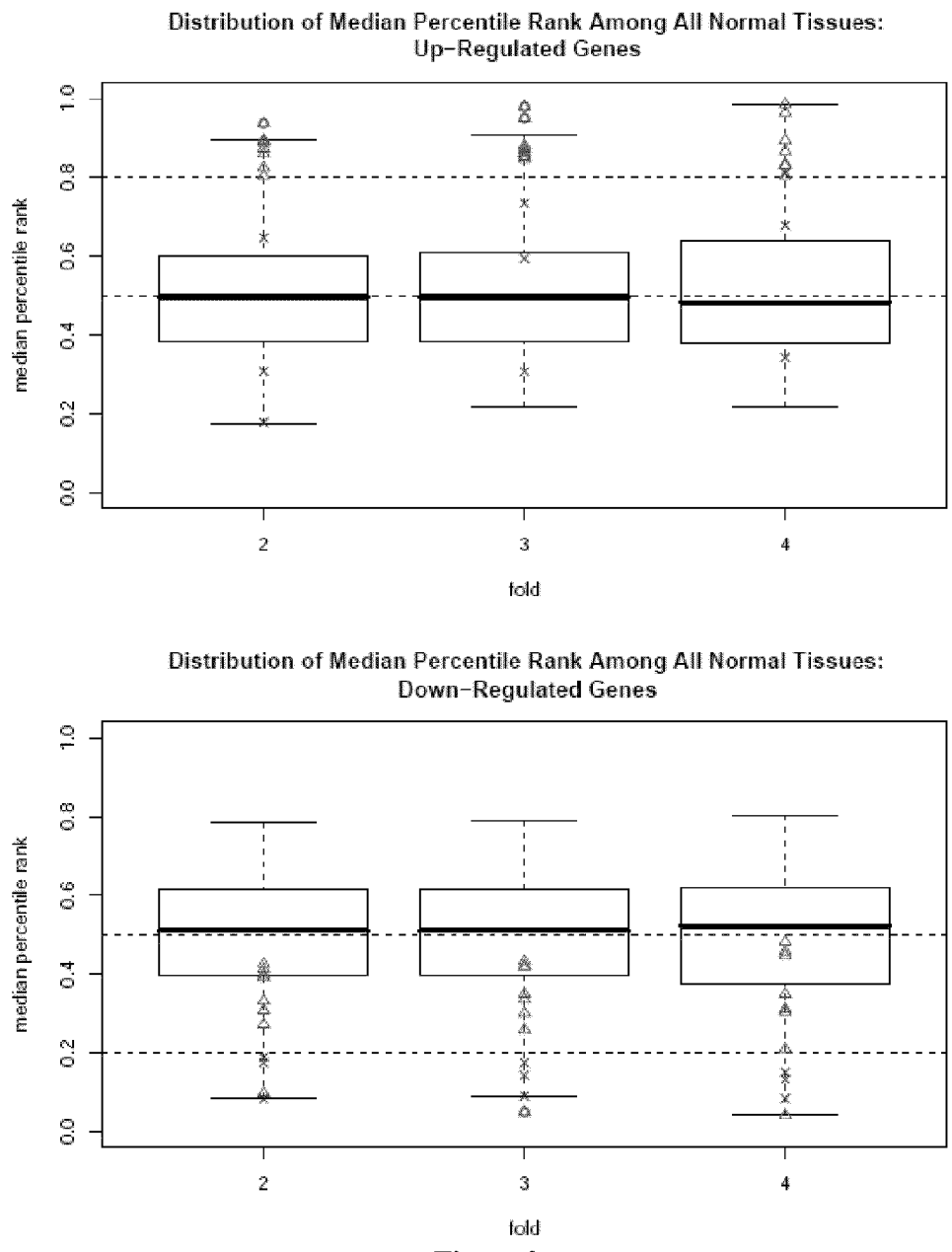
FIG. 3 is a graph showing the distribution of median percentile rank among all normal breast tissues. To see how the 11 outlier tissues differ from the rest of the normal tissues (n=132), we examined the distribution of the median percentile rank of the up-regulated and the down-regulated genes among all normal tissues (including the outlier tissues) using the fold change cutoffs of 2, 3, and 4. Results in the figure showed that the majority of tissues distributed between 40% and 60% and centered around 50% in terms of the median percentile rank either for the up-regulated or the down-regulated genes. Eight out of 11 outlier tissues had a very high median percentile rank (>80%) for the up-regulated genes. The other three outlier tissues gave a very low median percentile rank (<20%) for the down-regulated genes.

Outlier Breast Tissues 11 outlier breast tissues were identified using the outlier tissue approach (see, for example, Methods section infra) to re-evaluate the 143 normal breast tissues whose gene expression profiles more closely approximated that of the IDC samples rather than the rest of the 132 normal breast tissues. Eight of these 11 outlier tissues had a median percentile rank greater than 80% among all the 143 normal tissues (i.e., the top 20%) at the 2, 3, and 4 fold-change cutoffs, shown in FIG. 2. The other 3 outlier tissues had a median percentile rank less than 20% (i.e., the bottom 20%) for the under-expressed probe sets. Distinction of the outlier tissues from the normal breast tissues was further demonstrated in FIG. 3.

Example 4

Histologic Findings in Outlier Breast Tissues

FIG. 4 summarizes histological findings of the 11 outlier breast tissues used in this study. Most of these specimens consisted of unremarkable benign breast tissues. Some of the specimens had a minor component showing other benign changes, but all of these specimens were free from preneoplastic changes. See FIG. 5. These 11 outlier tissues were derived from 10 individual subjects with two outlier tissues being derived from the same patient. The histology of adjacent breast tissues to these 11 outlier tissues was also examined (data not shown). Outlier gene expression level of these adjacent normal tissues scored between the non-adjacent normal breast tissues and the outlier tissues. See the outlier genes section and FIG. 6.

Example 5

Outlier Gene

An outlier gene signature was developed by forming a "common set" of genes whose expression varied (up or down) at high levels in the 11 outlier tissues. The outlier genes consisted of 109 up-regulated probe sets (96 unique genes) and 31 down-regulated probe sets (21 unique genes). Of the entire list, presented in FIG. 7 and Table 6, a subset of outlier genes was selected, seen in FIG. 8 and Table 7. Expression of the outlier genes discriminated the normal, outlier, and IDC tissues from each other. See FIG. 9.

Example 6

Pathway Analysis of Outlier Genes

Pathway analysis showed that the outlier gene set was remarkably over-represented by cell cycle genes. There were 11 cell cycle related pathways represented in the outlier signature (p value <0.01), depicted in FIG. 10. This result was distinct from the IDC gene signature which had the cell adhesion as the primary components and cell cycle as a secondary component. Since the outlier gene signature was derived from the IDC gene signature, the difference in functional classes of genes would not have been expected in the absence of a selection bias. The majority of the outlier genes were classified to be primarily associated with DNA replication and mitosis, two hallmark events associated with proliferation. See FIG. 11. This observation may indicate the importance of these features in early stages of tumorigenesis. Importantly, this class of mitotic genes is well known to exhibit periodic expression at the transcriptional level in cultured cells, and previous studies have reported that genes related to S-phase and mitosis are also found highly expressed in tumors in cases where there is a relatively high fraction of cycling cells[8].

Example 7

Re-Examination of Outlier Tissues and the Adjacent Tissues

Figure 6:
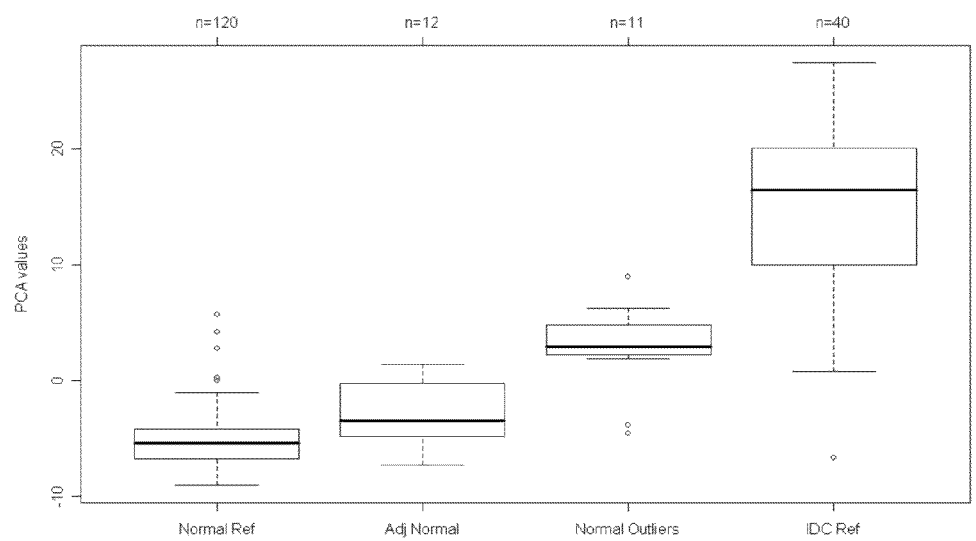
FIG. 6 is a graph evaluating outlier tissues and their adjacent tissues. The built-up PCA model based on the outlier gene signature was used to calculate the first PCA score for each tissue. This figure displayed distribution of the first PCA score at each group (normal reference (normal tissues from subjects who had no outlier tissue), adjacent normal tissues to outlier tissue (Adj-normal), normal outlier tissues, and IDC). The plot showed both an increasing trend from the normal reference tissues to the adjacent normal tissues (p=0.011) and from the adjacent normal tissues to the outlier normal tissues (p=0.0015).

Principal component analysis (PCA) was applied for the outlier gene signature using all IDC and normal breast tissues (excluding the outlier and the adjacent breast tissues) to calculate the first PCA score for IDC, normal, outlier, the adjacent normal tissues. FIG. 6 showed that, the median of the first PCA score was highest in the outlier tissues followed by the adjacent normal tissues (p value=0.0015 based on t-test for the outlier versus the adjacent normal tissues). The normal breast tissue had the lowest score (p value=0.011 for the comparison of the adjacent normal tissues to the normal breast tissues).

Examples 8-12 below describe the external validation of the inventors' malignancy-risk signature. The value of the outlier gene signature was assessed on five external, independent data sets. These external datasets permitted the evaluation of a number of properties of the outlier signature including differentiation of normal versus IDC tissues, disease progression, cancer risk, and metastasis.

Example 8

Turashvili's Study of Normal and IDC Comparison[9]

Figure 12:
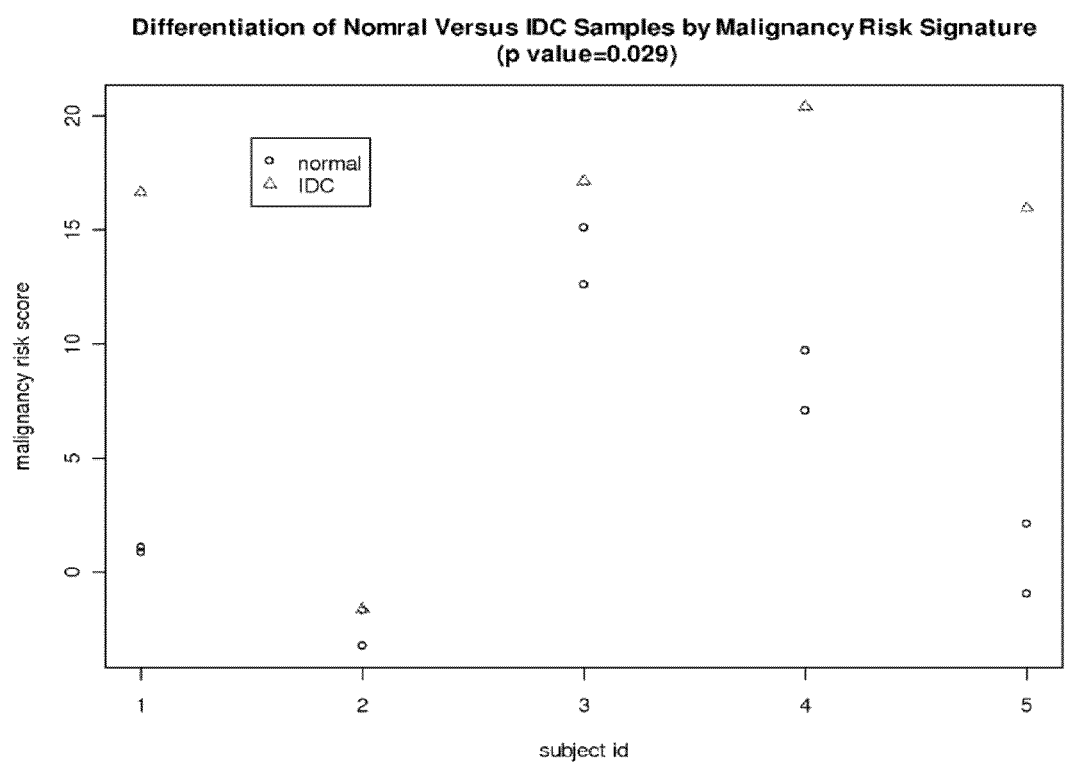
FIG. 12 is a graph of the external validation for classification of normal and IDC tissues in Turashvili's study. Samples were analyzed using Affymetrix U133 Plus 2.0 chip. Data was processed based on RMA method. Since our study used the same platform, for validation purpose, we used the built-up PCA model from our Affymetrix data to predict the first PCA score for the 5 IDCs and the associated 10 normal breast tissues. Results in the figure showed a higher PCA score in IDC than in normal tissue within the same patient with a p value=0.029 based on the random effect model to control for subject variation.
Figure 14:
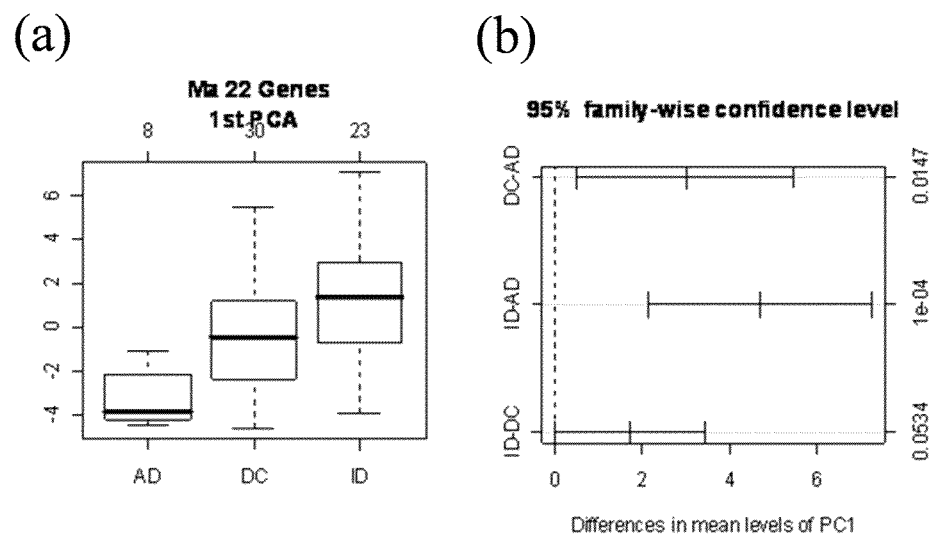
FIG. 14 is a graph of the external validation for disease progression in Ma's study. Principal component analysis was performed for the 22 matched genes (21 unique genes with RRM2 gene duplicated) using the first principal component. (a) Displayed distribution of the first PC score (y axis) among the three groups: ADH, DCIS (DC), and IDC (ID). (b) 95% confidence interval of pair-wise comparison for the first PC score among the three groups with adjusted p value in the right-hand side's y axis. Results for the 22 genes showed an increasing pattern from ADH to IDC in the first principal component score.

This study examined 10 patients (5 IDCs and 5 ILCs) and collected one tumor tissue (IDC or ILC) with two normal tissues (ductal or lobular cells) from each subject. The PCA model was applied to obtain the first PCA score for the 5 IDCs and the associated 10 normal breast tissues. Results showed the first PCA score was higher in IDC than in normal tissue within the same patient (p value=0.029 based on the random effect model to control for subject variation). See FIG. 12 and Table 8. This result indicated the outlier gene signature was able to differentiate IDC from normal tissue.

Example 9

Moffitt DCIS Samples

A set of 23 DCIS samples were collected to evaluate the disease progression feature of the outlier gene signature. Based on the PCA model derived from the previous 132 normal breast and 42 IDC tissues (excluding the 11 outlier tissues), the first PCA score were calculated for the DCIS tissues. Results showed a clear progression pattern from normal breast, outlier, DCIS, to IDC, shown in FIG. 13(a). Ranking the disease status from 0 to 3 for normal breast to IDC, the calculated Pearson or Spearman correlation was 0.87 and 0.8, respectively, with a significant p value <0.001.

Figure 30:
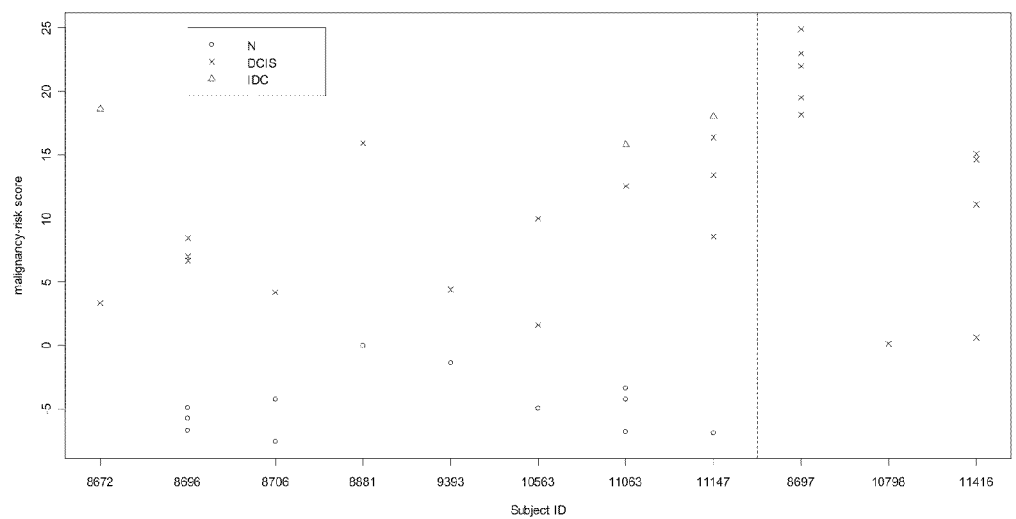
FIG. 30 is a graph for the validation of Moffitt ductal carcinoma in situ (DCIS) samples for cancer progression.

Further analysis using logistic regression model (with the normal group as the control group) yielded a significant association (OR=1.73, 2, and 1.76 for IDC-like normal, DCIS, and IDC, respectively, with p value <0.0001). Furthermore, the malignancy-risk score (equivalent of PCA score) of DCIS was lower than IDC, but higher than normal tissue (p=0.0005 based on one sample t-test using the difference of the maximum risk score in the normal tissues and the minimum risk score in the DCIS samples) within each patient (FIG. 30).

Example 10

Ma's Breast Cancer Study[10]

Example 10A

Figure 15:
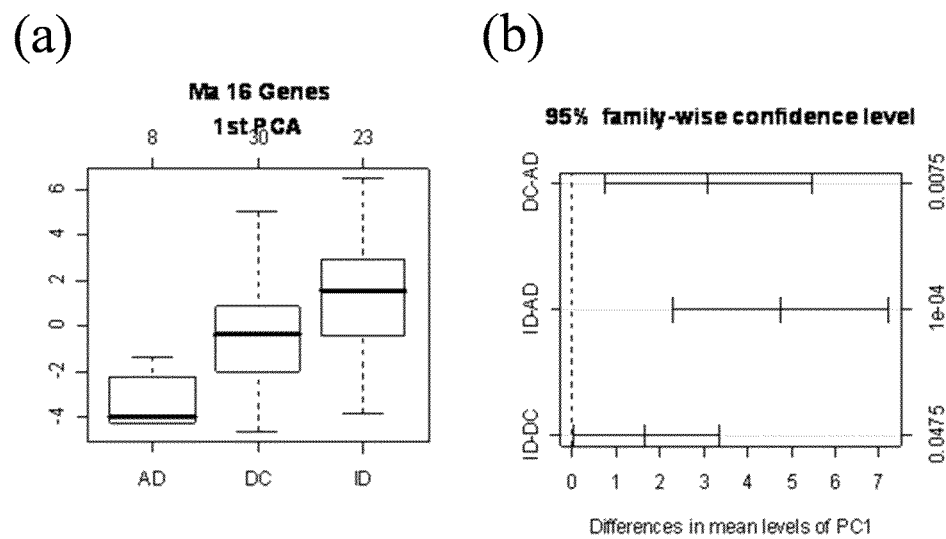
FIG. 15 is a graph of the external validation for disease progression in Ma's study. Principal component analysis was performed use only the 16 genes with increasing pattern of gene expression, using the first principal component. (a) Displayed distribution of the first PC score (y axis) among the three groups: ADH, DCIS (DC), and IDC (ID). (b) 95% confidence interval of pair-wise comparison for the first PC score among the three groups with adjusted p value in the right-hand side's y axis. Result shown for the 16 increasing genes yielded an enhanced increasing pattern in the first principal component score. To see whether the 16 genes dominate PCA analysis results, two sets of genes were compared (16 increasing genes versus 5 non-increasing genes) in PCA analysis. Result shown for the 16 increasing genes yielded an enhanced increasing pattern in the first principal component score.
Figure 16:
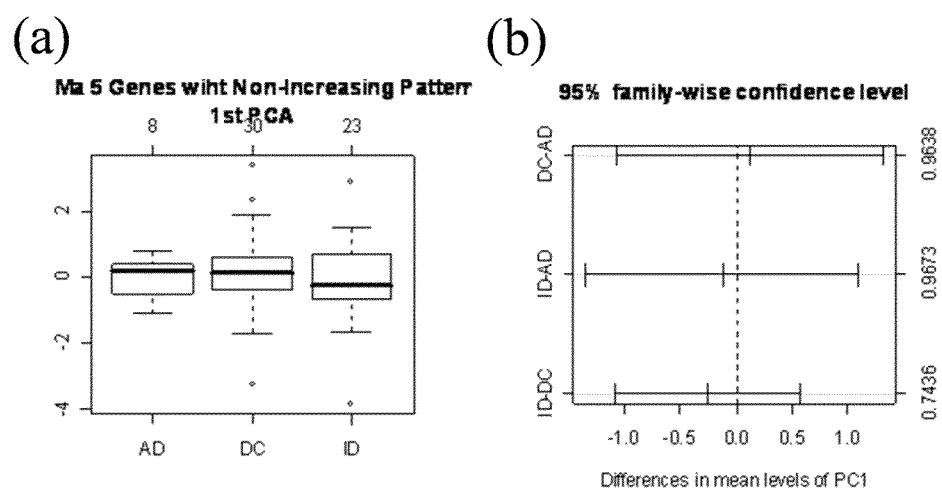
FIG. 16 is a graph of the external validation for disease progression in Ma's study. Principal component analysis was use only the other 5 genes with non-increasing pattern, using the first principal component. (a) Displayed distribution of the first PC score (y axis) among the three groups: ADH, DCIS (DC), and IDC (ID). (b) 95% confidence interval of pair-wise comparison for the first PC score among the three groups with adjusted p value in the right-hand side's y axis. Specifically, the score in ADH group was deviated away from the DCIS and IDC (p value=0.01 and 0.0001). Univariate analysis of these 22 genes also showed a majority of them with a statistically significant fold change (>2). PCA analysis in the 5 non-increasing genes showed that the three groups (ADH, DCIS, and IDC) had a similar distribution of the first principal component score around 0.
Figure 17:
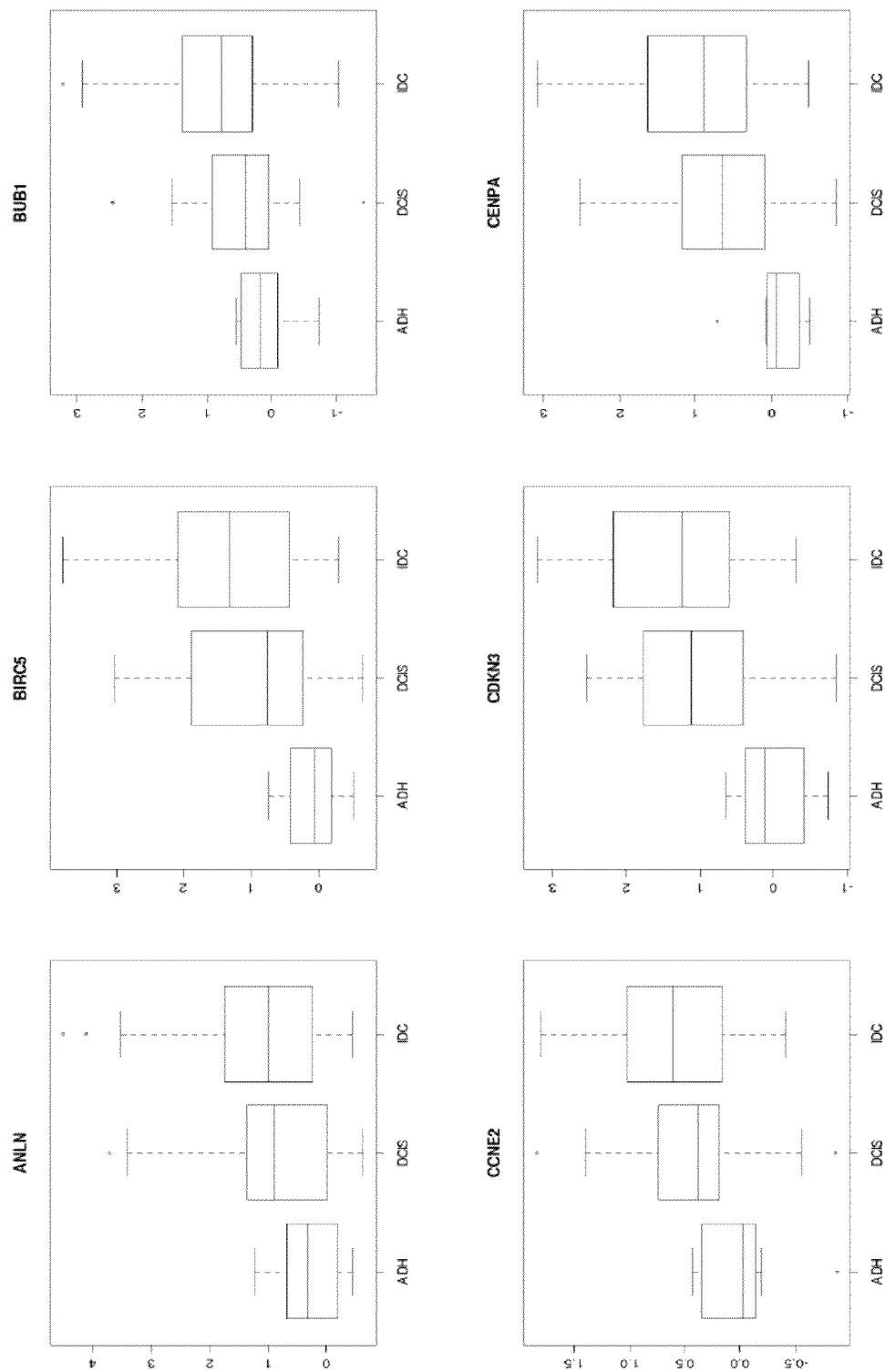
FIG. 17 is a graph of the external validation for disease progression in Ma's study. Principal component analysis was performed for the 22 matched genes (21 unique genes with RRM2 gene duplicated) using the first principal component. The figure displays the outlier genes which show disease progression from ADH to IDC Moreover, 16 genes displayed a similar increasing pattern.
Figure 18:
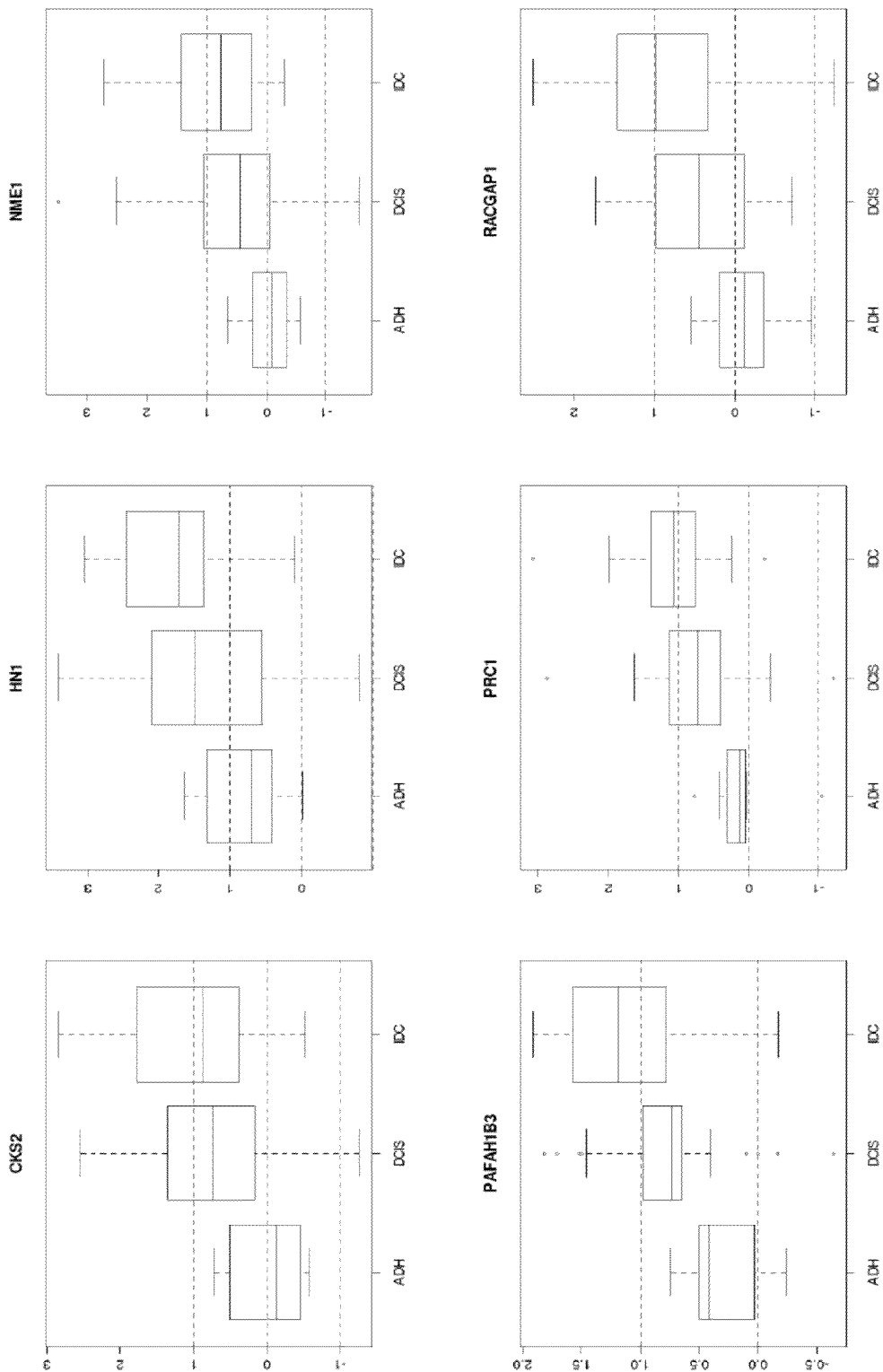
FIG. 18 is a graph of the external validation for disease progression in Ma's study. Principal component analysis was performed for the 22 matched genes (21 unique genes with RRM2 gene duplicated) using the first principal component. The figure displays the outlier genes which show disease progression from ADH to IDC Moreover, 16 genes displayed a similar increasing pattern
Figure 19:
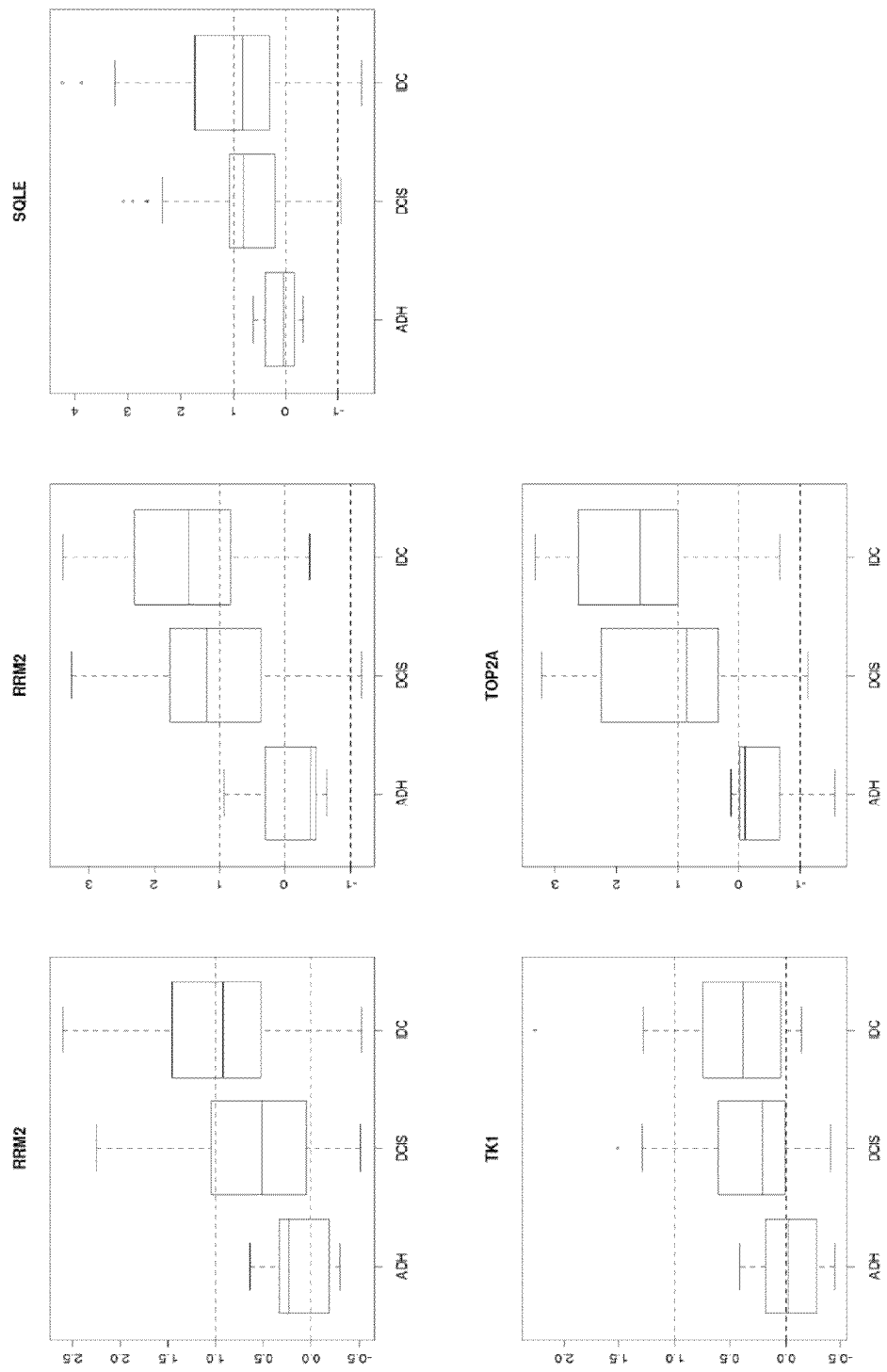
FIG. 19 is a graph of the external validation for disease progression in Ma's study. Principal component analysis was performed for the 22 matched genes (21 unique genes with RRM2 gene duplicated) using the first principal component. The figure displays the outlier genes which show disease progression from ADH to IDC Moreover, 16 genes displayed a similar increasing pattern.

Eight ADH, 30 DCIS, and 23 IDC samples were collected and cDNA microarray used to generate expression data. There were 21 genes overlapping with the outlier gene signature. Univariate analysis of these 21 genes showed a majority of them with a statistically significant fold change (>2), shown in FIG. 14(a) to FIG. 19(f). Moreover, 16 genes showed an increasing pattern from ADH to IDC based on the first PCA score. FIGS. 15(a) and 15(b), adjusted p value <0.05 among the 3 pair-wise comparisons.

Example 10B

Background: To further evaluate the potential of the malignancy-risk signature to predict the risk of cancer progression, the Ma et al. data were analyzed. The study collected 8 atypical ductal hyperplastic (ADH), 30 DCIS, and 23 IDC samples and used cDNA microarray to generate expression data. There were 21 genes in common with the malignancy-risk gene signature. We compared the malignancy-risk score among the three groups: ADH, DCIS, and IDC.

Data Analysis: We used the 21 genes to calculate the malignancy-risk genes (see Statistical Methods, see Example 13). Correlation analysis was used to assess cancer progression and logistics regression model was used to examine the association of the malignancy-risk score with cancer status.

Figure 31B:
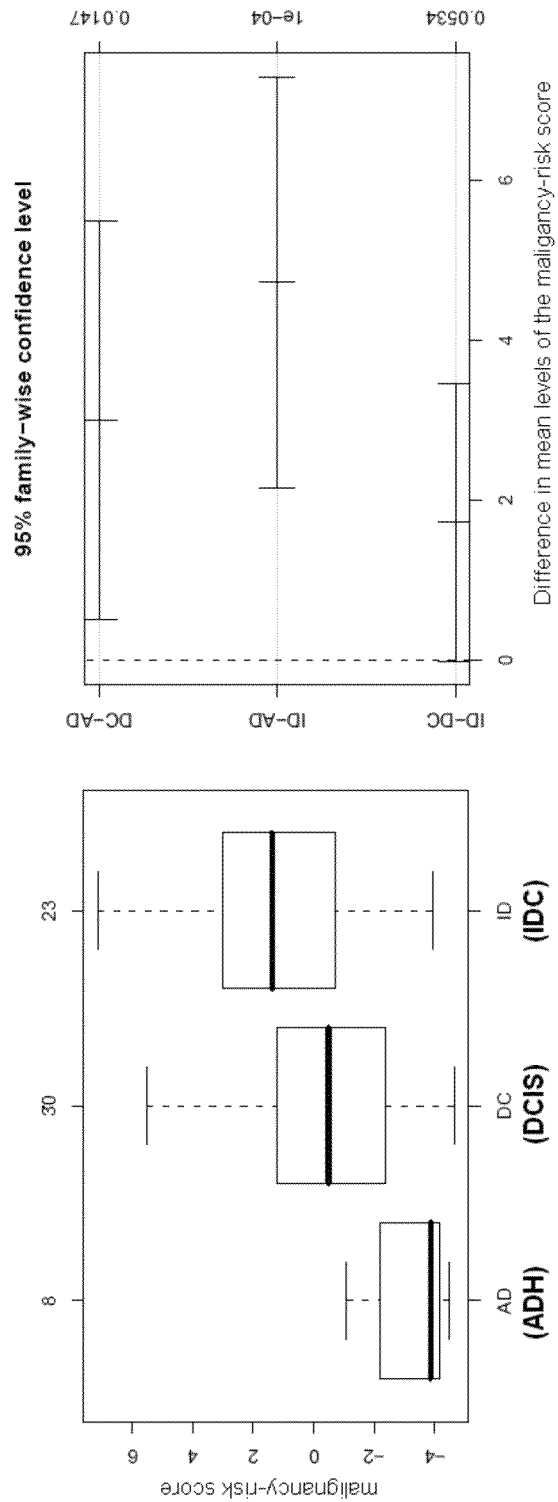
FIG. 31B displays the distribution of the malignancy-risk score among the three groups: ADH (labeled as AD), DCIS (labeled as DC), and IDC (labeled as ID) (first panel) and displays the 95% confidence interval of pair-wise comparison for the risk score among the three groups with adjusted p value in the right-hand side's y axis (second panel).

Results: Correlation analysis showed an increasing pattern of the risk score with cancer progression from ADH to IDC (FIG. 31B: the first panel). Pearson or Spearman correlation coefficient was 0.5, with a significant p value <0.0001 by ranking the cancer status from 1 to 3 for ADH to IDC. Pair-wise comparison showed that the risk score was statistically significant difference between IDC/DCIS and ADH (adjusted p value=0.0001, and 0.0147 for IDC and DCIS, respectively). Univariate correlation analysis also showed 16 genes with a p value <0.05 (FIG. 31A). Further analysis using logistics regression model (with the ADH group as the control group) demonstrated a strong association (OR=2.28 and 3.31 for DCIS and IDC with p value=0.016 and 0.008, respectively).

Example 11

Poola's Atypical Ductal Hyperplastic (ADH) Study[11]

Example 11A

Figure 20:
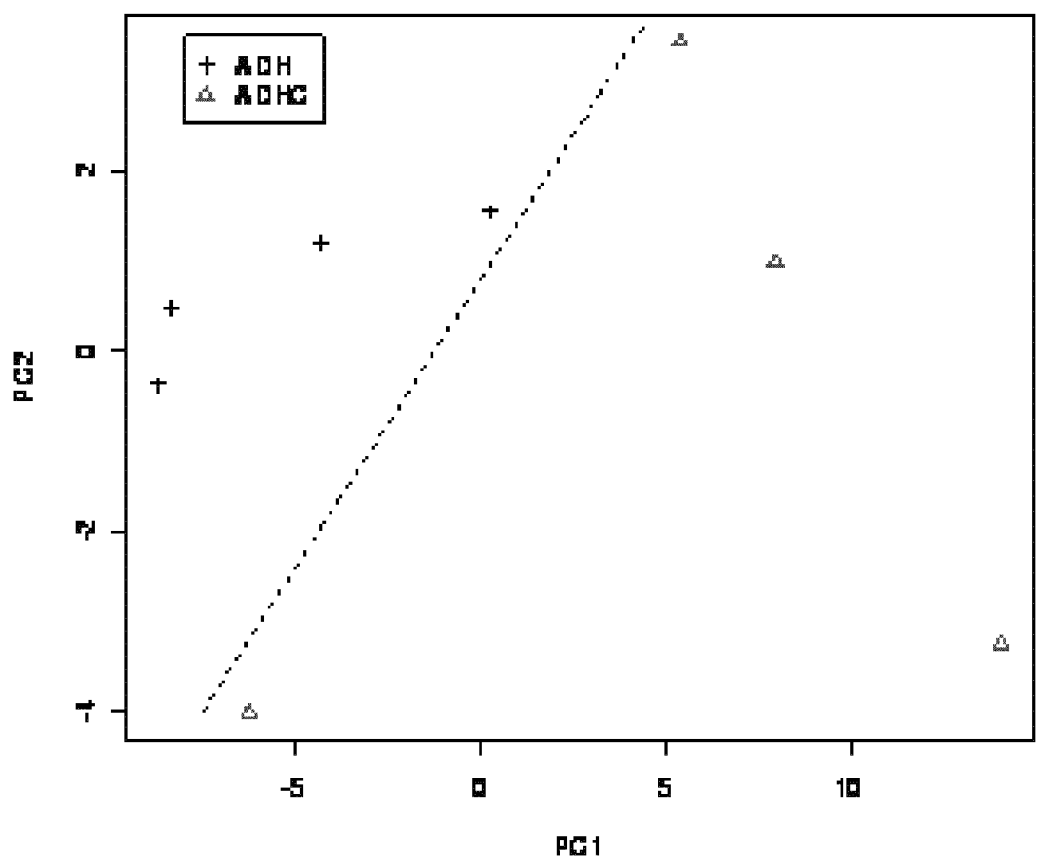
FIG. 20 is a graph of the external validation to assessing cancer risk in Poola's ADH study. PCA was applied to the overlapped 102 probe sets for the 4 ADHs and 4 ADHCs. The first two principal component scores were displayed in the plot with the first PCA (labeled as PC1) in the x axis and the second PCA (PC2) in the y axis. Result showed the first two principal components were able to differentiate ADH tissue between with and without cancer, indicating the ability of the outlier gene signature to assessing cancer risk.

Four ADH tissues were collected from patients without a history of breast cancer, and another 4 ADH tissues from patients where breast cancer developed, labeled as ADHC. There were 102 probe sets that overlapped with the outlier gene signature. PCA was applied to these 102 probe sets for the 4 ADHs and 4 ADHCs. The results showed that the ADHC group had a higher score than the ADH group for the first PCA score, seen in FIG. 20. The majority of ADHC tissues (3 out of 4) yielded a score above 5, in contrast to most ADH tissues, which had negative scores. The ADH group had a narrow range of scores between −1 and 2 in the second PCA, while ADHC yielded a wide range of scores. As a result, the first two PCA scores in the scatter plot were able to distinguish between ADH and ADHC.

Example 11B

Background: This study was selected in order to assess the potential of the malignancy-risk score to predict the risk of future cancer development in the breast associated with ADH. This study collected 4 ADH tissues from patients without a history of breast cancer (we labeled these tissues as ADHN), and another 4 ADH tissues from patients where breast cancer developed (we labeled these tissues as ADHC). There were 102 probe sets in common with the malignancy-risk gene signature. We compared the malignancy-risk score between the two groups (ADHN and ADHC).

Data analysis: We used the 102 probe sets to calculate malignancy-risk score. Logistic regression model was used to assess cancer risk. This was done in two ways. One was to use the median risk score to dichotomize patients into two risk groups (high risk with score >median and low risk with score <median) to calculate odds ratio (OR). The other way was to use the continuous risk score as the independent variable to calculate OR and to estimate the cancer-risk probability. We also performed two-sample t-test for the malignancy-risk score and for each malignancy-risk gene (univariate analysis).

Results: Analysis results from logistic regression model showed that the ADHC group had a higher risk score than the ADHN group (FIG. 32A) although the odds ratio was not statistically significant (OR=1.4 with p=0.123 for the continuous risk score and OR=9.0 with p=0.178 for the median-cutoff risk score) due to a very limited sample size (n=4 per group). Notably, three out the four ADHC patients had a risk score above 5 with a cancer-risk Probability >0.8 (based on the continuous risk score), in contrast to most ADHN patients with negative scores and a low cancer-risk probability. Two-sample t-test for the malignancy-risk score yielded a p value=0.08. For univariate analysis, there were 16 genes with p value <0.05 (FIG. 32B).

Example 12

Van't Veer Breast Metastasis Dataset[12]

Example 12A 78 breast cancer patient samples were collected and the time to metastasis was determined using a 70 gene signature and cDNA array. An independent set of 295 cancer patients were collected as validation for the 70 gene signature. The two datasets were used to examine if the outlier genes can predict metastasis. There were 117 features that overlapped with the outlier gene signature. First PCA scores were calculated based on these 117 features. The patients were grouped into low and high-risk groups by dichotomizing the first PCA score based on kmean[13] and the recursive partitioning and regression tree method[14]. Logrank tests showed a significant separation between the two risk groups ($\chi^2$=15.2 with p<0.0001 for the 78 patient data and $\chi^2$=21.3 with p<0.0001 for the 295 patient data). Seven common genes were then analyzed (overlapping with the 70 genes and the 117 features), seen in FIG. 8. Analysis based on the same statistical method yielded a similar result ($\chi^2$=14.7 with p=0.0001 for the 78 patient data and $\chi^2$=20.5 with p<0.0001 for the 295 patient data), shown in FIGS. 21(a) through 21(c).

Example 12B

Background: This study collected one training set (a total of 78 breast cancer patient samples) and one test set (n=295 patients, including 32 patients from the training set) with the time to metastasis as the clinical outcome to develop a 70 gene signature. In our study, we used the training set (n=78) and the test set which excluded the 32 patients from the training set (n=263) to examine if the malignancy-risk genes could predict metastasis. There were 117 features that were in common with the malignancy-risk gene signature. Among them, there were 7 genes in common (FIG. 33A) between the 70 gene signature and the malignancy-risk gene signature.

Data analysis: We compared performance of survival analysis for the 3 gene signatures (malignancy-risk signature, 70 gene signature, and 7 genes in common) based on the malignancy-risk score.

Malignancy-risk score: We first evaluated the overall performance of the 117 features for the malignancy-risk gene signature. The risk score was calculated by converting expression of the genes into the first principal component score (based on principal component analysis method; see Statistical Methods, see Example 13). We used median of the risk score as cutoff to dichotomize the 78 patients (training set) into two risk groups. The median cutoff of the risk score from the training set was also used to dichotomize the patients into two risk groups for the test set (n=263). Log rank test showed a significant separation between the two risk groups ($\chi 2$=12.2 with p=0.0005 for the training data; and $\chi 2$=22.4 with p<0.0001 for the test data). The risk score was calculated in the same way for the 70 gene signature and 7 common genes, respectively.

Figure 33C:
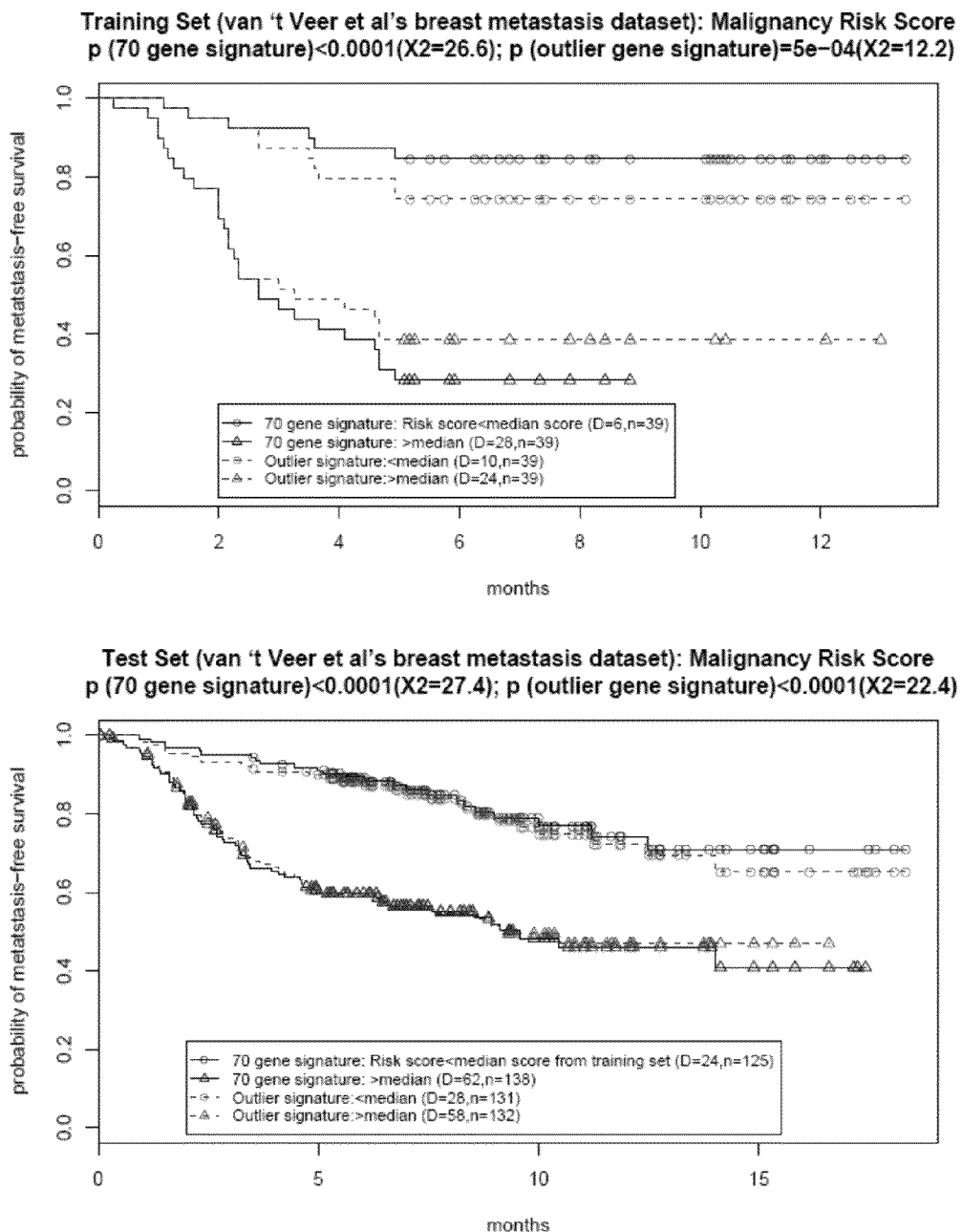
FIGS. 33C and D are graphs of the malignancy-risk score for the training and test sets.
Figure 33D:
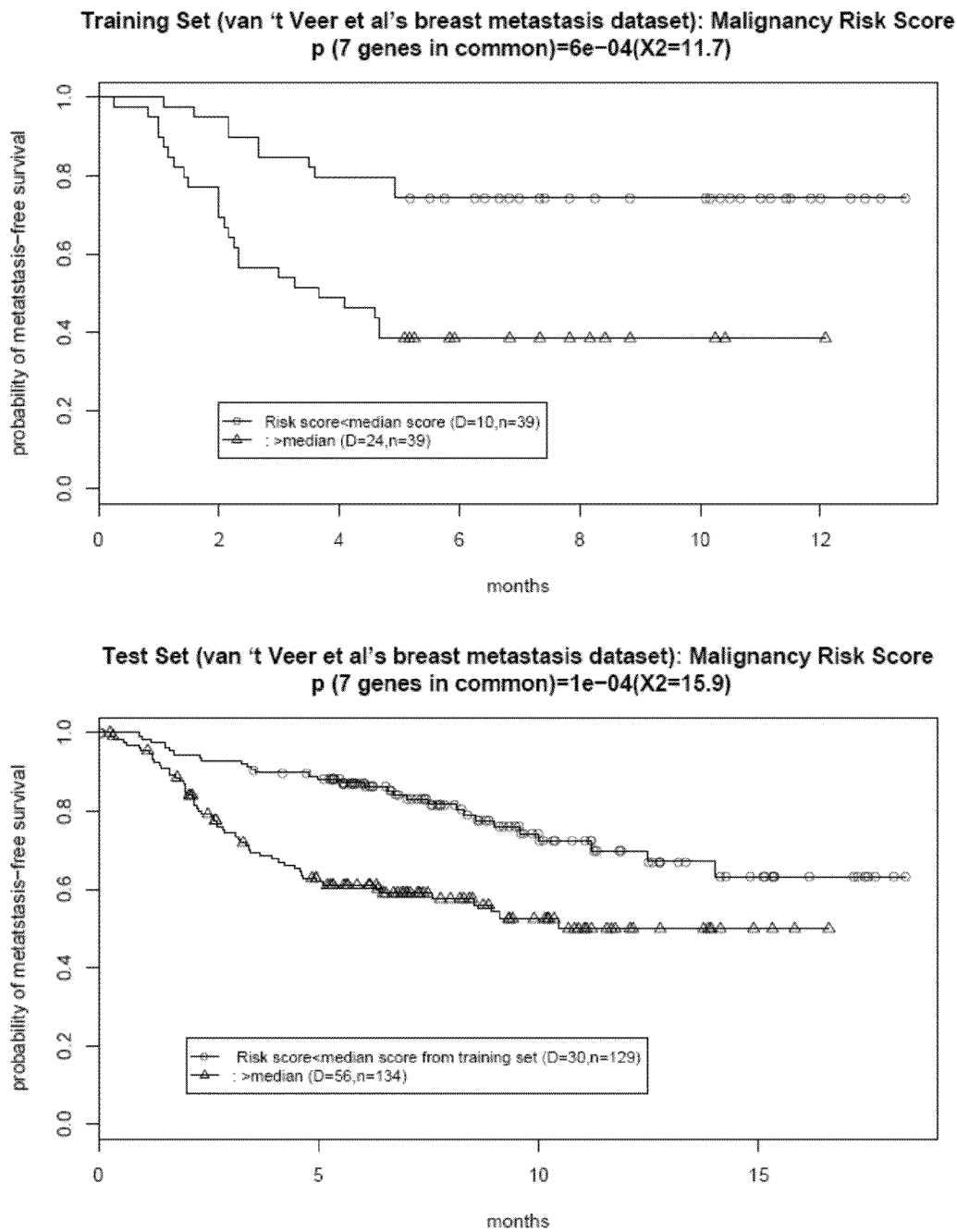
FIG. 33 shows the external evaluation to assess prognostic feature in van't Veer et al's breast metastasis dataset.
FIG. 33A depicts the univariate Cox proportional hazards model for the 7 genes in common with the malignancy-risk signature.
FIG. 33B lists malignancy-risk genes with p value <0.05 in both training and test sets using univariate Cox proportional hazards model.
Figure 34A:
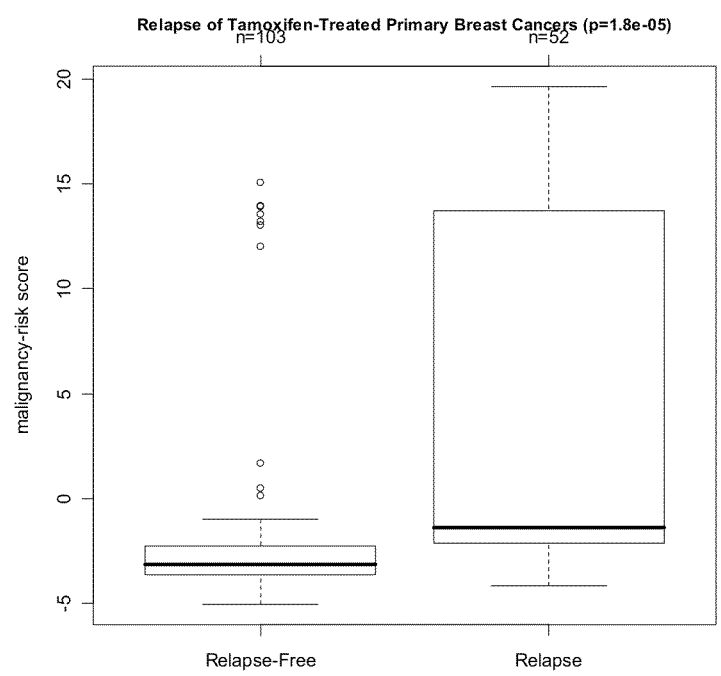
FIG. 34A depicts the distribution of malignancy-risk score among the two groups, relapse and relapse-free.

Results: The three gene signatures performed well to separate survival curves of the two risk groups (FIG. 33C-D) for both datasets (training and test sets). The 70 gene signature performed the best because the signature was derived from the dataset (Figure A). However, the performance for the malignancy-risk signature was comparable to the 70 gene signature, especially in the test set. Even for the 7 genes in common, it also had a comparable performance (FIG. 33D). Univariate Cox proportional hazards model also showed 48 genes with p value <0.05 in both training and test sets (FIG. 33B).

Discussion

Identification of high-risk normal tissue has great potential application in clinical practice, in both evaluating the risk associated with routine breast biopsies as well as the risk of local recurrence following lumpectomy. Detecting high-risk normal tissue, however, remains a challenging task. The invention described herein provides, in one aspect, identifying high-risk normal tissue using gene expression profiles. One underlying rationale, to which the inventors are not bound, for this invention is a histologically normal tissue with "tumor-like" gene expression pattern might harbor substantial risk for future cancer development. Genes associated with these high-risk tissues were referred to as "outlier" genes. Using this rationale, 11 outlier tissues out of 143 normal breast tissues were identified, and the outlier gene signature was developed using the outlier tissue approach. A careful re-examination of all outlier tissues showed the tissues were histologically normal with no observable indications of cancer development. See FIG. 5. However, the expression profile of these outlier tissues suggested similarity to tumor tissue, indicating that these tissues might harbor increased risk for cancer development.

The outlier gene signature was tested in four validations. The first verified that the outlier genes identified in histologically normal breast tissues adjacent to invasive cancers were also highly associated with invasive ductal carcinomas (IDC). The Turashvili et al.[9] dataset was used for evaluation and the outlier gene signature was found able to differentiate the IDC and normal tissues not linked to cancer, confirming the outlier genes as a subset of IDC tumor associated genes.

The second validation tested the risk of disease progression, where cancer risk was considered on a continuous spectrum with normal tissue in the lower end and IDC tissue at the higher end. As ADH and DCIS have been shown as precursors of IDC, it was ascertained whether the outlier gene signature exhibited a progressive trend from normal to IDC with ADH and DCIS as intermediate stages in the cancer risk spectrum. The existence of a strong trend with these features would provide a compelling evidence for the application of this signature on early prevention of cancer development. The outlier genes were tested on two datasets: Moffitt Cancer Center derived DCIS samples and Ma et al data[10]. Results from both datasets showed first PCA scores for the ADH or DCIS tissues were higher than outlier tissues, but lower than IDC, showing a disease progression pattern from outlier, to ADH, to DCIS, to IDC. See FIGS. 13(a) and 13(b). Moreover, 16 genes in the Ma dataset were identified that overlapped with the outlier signature, with an increasing expression pattern from ADH to IDC, seen in FIG. 8 and FIGS. 17(a) to 19(f). The majority of the overlapping genes are known to be involved in the cell cycle. Since these genes were highly associated with cell proliferation and exhibited expression changes that were proportional to disease stage, these genes might be risk genes (precursor genes) useful in predicting cancer development and recurrence.

The third validation was to evaluate the capability of the outlier gene signature in predicting cancer development risk using the Poola's dataset. Analysis showed 3 out of 4 ADHC patients had an unusually high PCA score. This result supports the concept that outlier gene signatures can predict cancer risk. Furthermore, the ADH gene signature and the outlier gene signature shared similar cellular proliferation functions. Specifically, the Poola's study reported 11 major categories of cellular functions, and most genes were up-regulated in ADHC patients. Two of 11 up-regulated functions were cell cycle check points and nucleic acid biosynthesis. The majority of over-expressed genes in both functions were found in the outlier gene signature. See FIG. 8.

The last validation assessment tested prognostic features. While the outlier gene signature may be principally useful to assess cancer risk, this property was assessed in a broader scope. Since patients with high cancer risk are likely to develop metastasis, the outlier genes may play a key role for disease development. Validation results of Vant der Veer et al. breast metastasis dataset further supported this rationale. The overlapping 7 genes between the outlier signature and the Vant der Veer et al. dataset, see FIG. 8, identified patients at risk for metastasis and were mainly involved in proliferation.

While identification of high risk normal tissue is crucial, it is also important to understand the basic mechanism of how the molecular function changes in high risk normal tissue. The outlier gene signature showed significant expression in these 11 outlier tissues which were molecularly-suspect but histologically normal tissues. Adjacent normal tissues to the outlier tissues also showed a relatively higher expression of this gene signature than the rest of normal tissues, seen in FIG. 6. Furthermore, the pathway analysis showed the outlier genes were predominantly comprised of cell cycle activities. Further, the outlier genes were highly associated with two proliferation-related pathways: DNA replication and mitosis (14 and 25 up-regulated outlier genes, respectively) as shown in FIGS. 21(a) through 21(c). While the primary function of the majority of these genes spans a variety of metabolic processes, it is clear that nearly all of the components are associated with cellular proliferation, a process that should be limited in normal tissues.

Moreover, the outlier genes were highly associated with chromosomal instability (CIN)[16], chromosomal damage during cell division and a potential driving force for tumor initiation. There were 15 up-regulated outlier genes in the CIN25 gene signature with an outstanding CIN score, and another 13 up-regulated outlier genes in the CIN70 gene signature. The high correlation with CIN evidences that the outlier gene signature can explain early stages of cancer development and provides a simple mechanistic perspective on distinguishing outlier samples in a population of normal tissues.

Finally, it is clear that up to 40% of patients undergoing lumpectomy are at risk for local recurrence of breast cancer and that this risk might be predictable based on an outlier gene signature. Moreover, it is also clear that radiotherapy mitigates this risk, suggesting that the genes identified in high risk patients could be the target genes for effective radiotherapy. If an over-expression of these genes might result in a new cancer, suppression of these genes via radiotherapy might prevent the development of cancer.

In summary, using over a hundred of histologically normal breast tissues, an outlier gene signature of potential risk has been identified. This signature has a number of potential clinical applications such as judging risk of breast cancer development following routine breast biopsy, judging the need for adjuvant radiotherapy, and determining the need for completion of mastectomy following lumpectomy for the breast cancer patient.

Example 13

Additional Materials and Methods

Tissues and their Associated Clinicopathological Data

Figure 22:
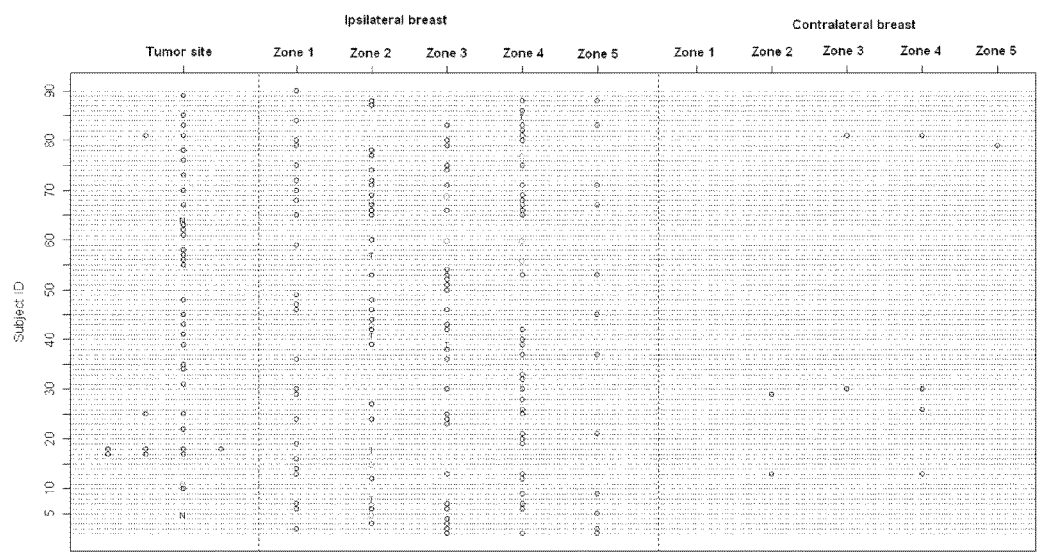
FIG. 22 depicts a graphical representation of tumor and normal tissues per case.

Tissues were collected in accordance with the protocols approved by the Institutional Review Board of the University of South Florida, and stored in the tissue bank of Moffitt Cancer Center. The tissues were embedded in Tissue-Tek® O.C.T., 5-μm sections cut and mounted on Mercedes Platinum StarFrost™ Adhesive slides. The slides were stained using a standard H&E protocol, and tissue boundaries marked. Using the marked slide as a "map", tissues were microdissected. Adipose tissues were trimmed away. Both histologically-normal breast tissues and IDCs were derived from 90 patients that underwent mastectomy for various stages of breast carcinoma and were collected and frozen in liquid nitrogen. Clinico-pathological data from the patients used in the study, including the tumor ER, PR and Her2/Neu status and tumor grade, are shown in Table 1. When possible, each mastectomy specimen was prosected to yield an IDC and up to five sequentially-derived, adjacent normal tissue samples in the ipsilateral breast or from the four quadrants of the contralateral breast. As a result, we collected 42 IDCs and 143 normal breast tissues from the 90 patients for microarray analysis. Due to RNA quality issue in some IDC and normal tissues, we did not have a complete set of IDC and normal tissues for some patients. There were 11 patients (a total of 34 tissues) with at least one normal and one IDC tissue, 19 patients (a total of 28 tissues) with IDC tissue only, and 60 patients (a total of 123 tissues) with normal tissue only. Table 2 lists number of normal and IDC tissues and their geographical locations relative to the incident tumor (see also FIG. 22).

Histology

Based on the histopathologic review by one breast pathologist (AN), all of the 143 histologically normal breast tissues were confirmed to be free of atypical ductal hyperplasia (ADH) and in-situ or invasive breast carcinoma. The 42 IDC tissues were also confirmed by the histopathologic review by the same pathologist, based on the modified Bloom and Richardson grading scheme[17].

RNA Extraction

Total RNA was extracted from the breast tissues using the Trizol method. Briefly, tissues were pulverized in liquid nitrogen, resuspended in 5 ml of lysis buffer, incubated for 3 min. at room temperature, and centrifuged at 11,500 g for 15 minutes at 4°. The aqueous phase was removed and put into another tube with 2.5 ml of isopropanol, mixed well and set at −20° C. for 20 minutes. The amount of RNA was quantitated by measuring A260. Microarray analysis was performed using the Affymetrix U133Plus 2.0 GeneChips (54,675 probe sets). Expression values were calculated using the robust multi-array average (RMA) algorithm[19] (Data is in the GEO repository: www.ncbi.nlm.nih.gov/geo/query/acc.cgi?acc=GSE10780.

RT-PCR Validation

Validation of 30 selected malignancy-risk signature genes (of 117 available) (see Table 3) was done using the TaqMan Low Density Arrays (Applied Biosystems, Foster City, Calif., USA). Due to limitation of sample availability, 5 "IDC-like" normal tissues, 8 IDCs, and 8 normal tissues were used for validation. Single stranded cDNA was synthesized from 1 ug of total RNA using random primers in a 20 uL reaction volume using Applied Biosystem's High Capacity cDNA Reverse Transcription kit. The 20 uL reactions were incubated in a thermal cycler for 10 min at 25° C., 120 min at 37° C., 5 sec at 85° C. and then held at 4° C. Real-time PCR was carried out using sequence specific primers/probes on the Applied Biosystems 7900 HT Real-Time PCR system. cDNA was diluted 2.5-fold; 5.0 uL of diluted cDNA was mixed with 45 uL of nuclease-free water and was added to 50 uL of TaqMan Universal PCR Master Mix (Applied Biosystems). The 100 uL total reaction mixture was loaded in the corresponding ports of a TaqMan Low Density Array (TLDA) card. Each TLDA card consisted of 3 replicates (4 samples per card). Expression value (ΔCt) was calculated by first averaging replicates for each gene and then normalized (subtraction) by an endogenous control gene (18S). Since a lower value of ΔCt indicates a higher expression, a −ΔCt was used to correlate with microarray gene expression.

Signature Generation/Statistical Methods

Statistical analysis included a series of steps to develop and validate the malignancy-risk gene signature (see FIG. 23):

1. Identification of IDC gene signature: In this first step, a set of 1038 genes (1,554 probe sets) was identified that distinguished the IDCs (n=42) from the histologically-normal tissues (n=143). The IDC gene set was identified by treating IDC and normal tissues as two independent groups (although some were derived from the same patients) and using Statistical Analysis of Microarray[20] at 1% false discovery rate (FDR) with a fold change >2 (see FIG. 23). The study aimed to collect multiple normal and IDC tissues from the same subjects, but due the heterogeneous nature of the sample set, some patients had only normal tissues sampled while others samples were limited to IDC tissues only. This nature of unbalanced data made it difficult to adjust for subject variation. Instead, we aggregated data into normal and IDC two groups for comparison. To ensure homogeneity for data aggregation, we checked whether overall gene expression from the normal tissues in patients with normal tissues available only was similar to the normal tissues in patients with both normal and IDC tissues available. We used Kmeans approach to classify all the normal tissues into two groups based on gene expression data. Fisher exact test did not show the two types of normal tissues were statistically different (p=0.53). We found similar results for the IDC tissues (p=0.99). These results suggested homogeneity for the two types of normal tissues (also for the IDC tissues).

2. Identification of "IDC-like" normal tissues: In this step, we used the IDC gene signature to identify 11 histologically normal breast tissues that had acquired the molecular fingerprint of IDC. The method first ranked all the normal tissues for each IDC tumor gene. (e.g., A normal tissue A is ranked as the top 1% (percentile rank=100%) for tumor gene X1, top 10% (percentile rank=90%) for tumor gene X2, top 20% for tumor gene X3, and so on). As a result, for the up-regulated IDC tumor genes (e.g., k1 genes), we will have a set (k1) of the tissue percentile ranks for each tissue. If a normal tissue displayed at least half (>k½) of the percentile ranks over 80% (i.e., the median percentile rank >0.8), we considered it as "IDC-like" normal tissue. Similarly, a normal tissue was also considered as an IDC-like tissue if a normal tissue had the median of the percentile ranks below 20% for down-regulated IDC tumor genes. A graphical presentation of the method is included in the FIG. 24.

A simulation was conducted and showed its effectiveness to identify IDC-like tissues (Table 4). Simulation Scheme: We generate two groups, normal and tumor tissues, with a sample size of 150 (normal) and 50 (tumor). We assume each gene chip contains 50,000 genes and these genes are independent. We consider a series of proportion of significant genes from 1% to 10% for evaluation. Here we label IDC-like normal tissue as 'outlier tissue'.

For non-significant genes, their expressions follow a standard normal distribution (i.e., N(0,1)) for both normal and tumor tissues. For significant genes, half of them have a higher expression in tumor tissue (up-regulation) with a normal distribution of N(1,1); and half of them a lower expression in tumor tissue (down-regulation) with a normal distribution of N(-1,1). On the other hand, the gene expression in normal tissue follows a standard normal distribution except the outlier normal tissues. Here we assume 10% normal tissues to be outlier with a tumor-like gene expression profile. For these outlier tissues, we assume they have the same expression distribution as the tumor ones (i.e., N(1,1) or N(-1,1)).

At each simulation, we use the Statistical Analysis of Microarray (SAM) and the outlier tissue approach (OTA) to analyze the simulated data. The threshold settings for SAM and OTA are the same as the ones used in our breast expression data. That is, we use a cutoff of false discovery rate (FDR) <0.01 and a fold change >2 in SAM to select tumor genes. For OTA, we use the median percentile rank >0.8 in the up-regulated tumor genes or the median percentile rank <0.2 in the down-regulated tumor genes to determine outlier tissue. As a result, we will collect a set of outlier tissues being identified correctly and a set of outlier tissues being misclassified to come up a 2×2 table (see Table 4A).

Evaluation: We perform 100 simulations. Each simulation generates a 2×2 table which allows us to calculate sensitivity and predictive value positive (PV+) for evaluation. We average each measure (i.e., sensitivity and PV+) over 100 simulations to examine performance.

Rationale for the use of sensitivity and PV+: Since outlier tissue is likely rare, the proportion of the outlier tissue is expected to be small. Because of this feature, accuracy rate (the proportion to be classified correctly) tends to be high even sensitivity or PV+ is low. In addition, we would like to have a procedure that yields most outlier tissues selected (i.e., high sensitivity) and has few or none of false outlier tissues selected (i.e., high PV+). For this reason, we consider the use of both sensitivity and PV+ to examine our approach. The curve of sensitivity versus PV+, in fact, is equivalent to the conventional Receiver Operating Characteristic (ROC) curve (i.e., sensitivity versus 1-specificity or true positive versus false positive). However, the conventional ROC curve focuses one aspect of evaluation of a screening test without considering the other curve (e.g., a high sensitivity does not guarantee a high or low PV+). In contrast, we present a unique evaluation of sensitivity versus PV+ to effectively assess the procedure.

Results: Simulation results show a high value of sensitivity and PV+ by the proposed approach in various proportions of significant genes (1%-10%) (see Table 4B). This observation demonstrates effectiveness of the approach in identifying outlier tissue.

3. Derive malignancy-risk gene score: Once the IDC-like normal tissues were identified, we then formed a common set of genes, "malignancy-risk signature genes", whose expression percentile rank was greater than 80% (or less than 20%) in most IDC-like normal tissues. Using the principal components analysis (PCA) method, we derived a "risk score" (malignancy-risk score) to represent an overall gene expression level for the malignancy-risk gene signature. First, we performed principal components analysis to reduce data dimension into a small set of uncorrelated principal components. This set of principal components was generated based on its ability to account for variation. We used the first principal component, as it accounts for the largest variability in the data, as a malignancy-risk score to represent the overall expression level for the signature. That is, malignancy-risk score=$\Sigma w_i x_i$, an weighted average expression among the malignancy-risk genes, where xi represents gene i expression level, wi is the corresponding weight with $\Sigma w_i^2 = 1$, and the wi values maximize the variance of $\Sigma w_i x_i$.

It is likely, when benign appearing breast tissues harbor malignancy-risk genes, the gene data will generate a high signal-to-noise ratio such that the first principal component with the largest variance will correspond to cancer risk-related information.

4. Cross-validation: Leave-one-out cross validation (LOOCV) was performed to evaluate robustness of the IDC and malignancy-risk gene signatures. This was done by excluding one sample at a time and repeating steps 1-3 to see how many were correctly identified (IDC genes, IDC-like normal tissues, and malignancy-risk genes).

5. Pathway analysis: Pathway analysis was done using MetaCore™ by GeneGo for steps 1 and 3 to identify biological functions associated with IDC genes and the malignancy-risk genes. We compared pathways of the two gene sets to reveal difference of biological processes between the IDC genes and the malignancy-risk genes.

6. RT-PCR validation: Pearson correlation was used to evaluate association of the malignancy-risk score between microarray and RT-PCR platforms. The malignancy-risk score was calculated using the 30 selected malignancy-risk signature genes (see Statistical Methods) for microarray and RT-PCR, respectively. Correlation analysis was also performed for each individual malignancy-risk gene. Analysis of variance was used to test the differences among the three groups (normal, IDC-like normal, and IDC) with the Tukey method[21] to adjust for p value for pair-wise comparison.

7. Clinical association: We assessed the prognostic potential of the malignancy-risk score on seven external independent data sets. Because each data set had a different set of available genes, we used whatever genes were in common with the malignancy-risk score to evaluate each data set (essentially a subset of the original malignancy-risk score). For binary clinical outcome (e.g., cancer development versus no development) or survival outcome (e.g., time to metastasis), the derived malignancy-risk score was dichotomized using the median cutoff (i.e., high risk with score >median and low risk with score <median). Logistic regression model was used to estimate odds ratio (OR) for binary outcome and log-rank test was used to test the difference of Kaplan-Meier survival curves for two risk groups for survival data. For ordinal clinical variable (e.g., from ADH, ductal carcinoma in situ (DCIS), to IDC), the continuous malignancy-risk score was used to correlate with disease severity using Pearson correlation to evaluate the trend of the malignancy-risk gene signature with cancer progression.

Example 14

ER/PR/Her2 Analysis

The 11 IDC-like normal breast tissues identified in Example 3 where analyzed for their ER, PR, and Her2/neu status. Fisher exact test showed no significant association of patients harboring IDC-like normal tissues with ER/PR/Her2 grade (Table 5)

Example 15

Cross-Validation

Figure 25B:
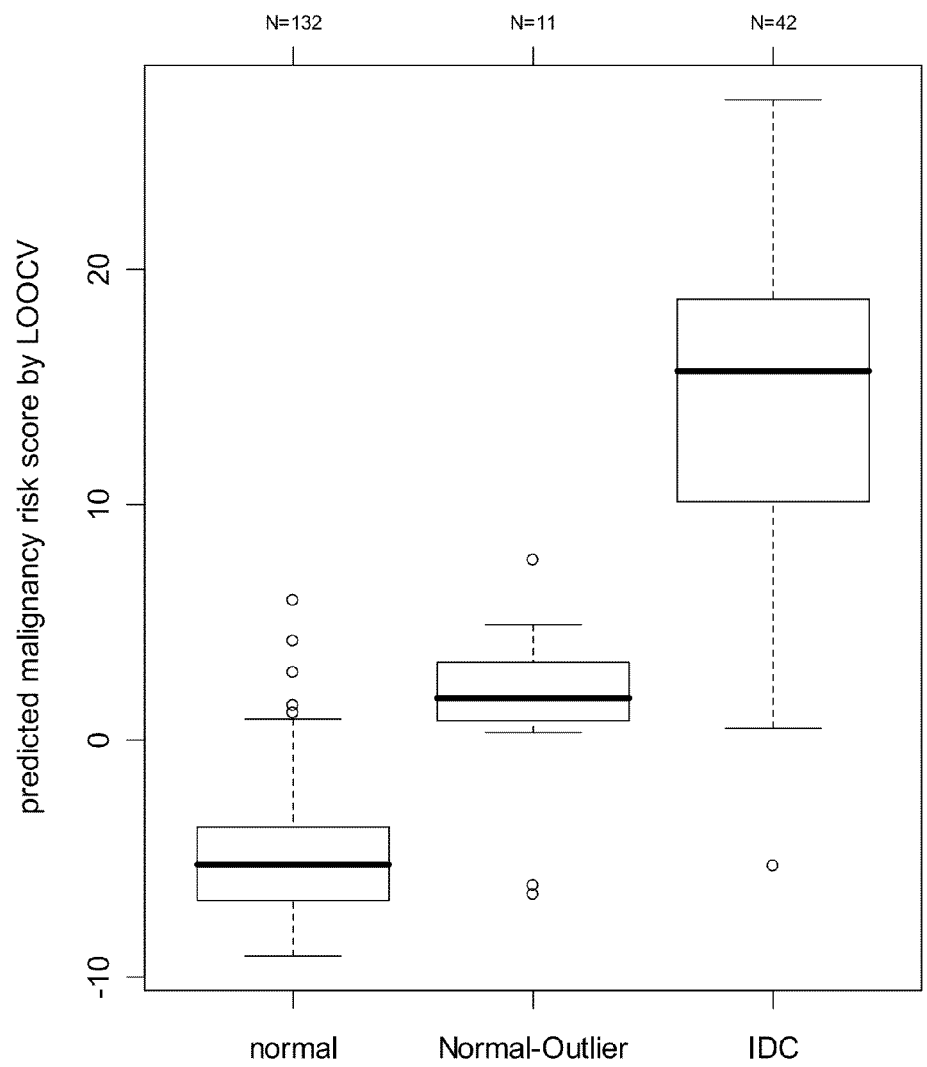
FIG. 25B depicts the distribution of the predicted malignancy-risk score by LOOCV among the three groups: normal, outlier (labeled as Normal-outlier), and IDC.

The malignancy-risk score (equivalent to PCA score) was analyzed by Leave-one-out crossvalidation (LOOCV). Leave-one-out cross validation (LOOCV) was implemented by excluding one sample at a time and repeating statistical steps 1-3 (i.e., IDC genes, outlier tissues (which can be used to represent IDC-like normal tissue), and malignancy-risk genes; see Statistical Methods). In other words, each time we hold one sample as a test sample and used the rest samples to identify an IDC gene set (step 1). The selected IDC genes were then used to identify outlier tissues (step 2). We used these selected outlier tissues to identify malignancy-risk genes (step 3). These malignancy-risk genes were used to predict the malignancy-risk score for the sample being hold. As a result, each time we collected four metrics: a set of IDC genes, a set of outlier tissues, a set of malignancy-risk genes, and the predicted malignancy-risk score (for the sample being hold). We examined the first three metrics from LOOCV to see how consistent with the ones from the whole dataset. Analysis of LOOCV yielded a high degree of consistency: most IDC genes (>98%), outlier tissues (>90%), and malignancy-risk genes (>90%) were identified at each leave-one-out iteration (FIG. 25A) Moreover, at each iteration, we calculated a predicted malignancy-risk score for the sample being excluded. Correlation analysis showed a high correlation of the predicted malignancy-risk score and the disease status (i.e., rank normal, outlier, and IDC from 0 to 2; Pearson correlation=0.89 and Spearman correlation=0.74 with p<0.0001; FIG. 25B).

Example 16

Weak Correlation of Malignancy-Risk Score with ER, PR, and Her2

Figure 26A:
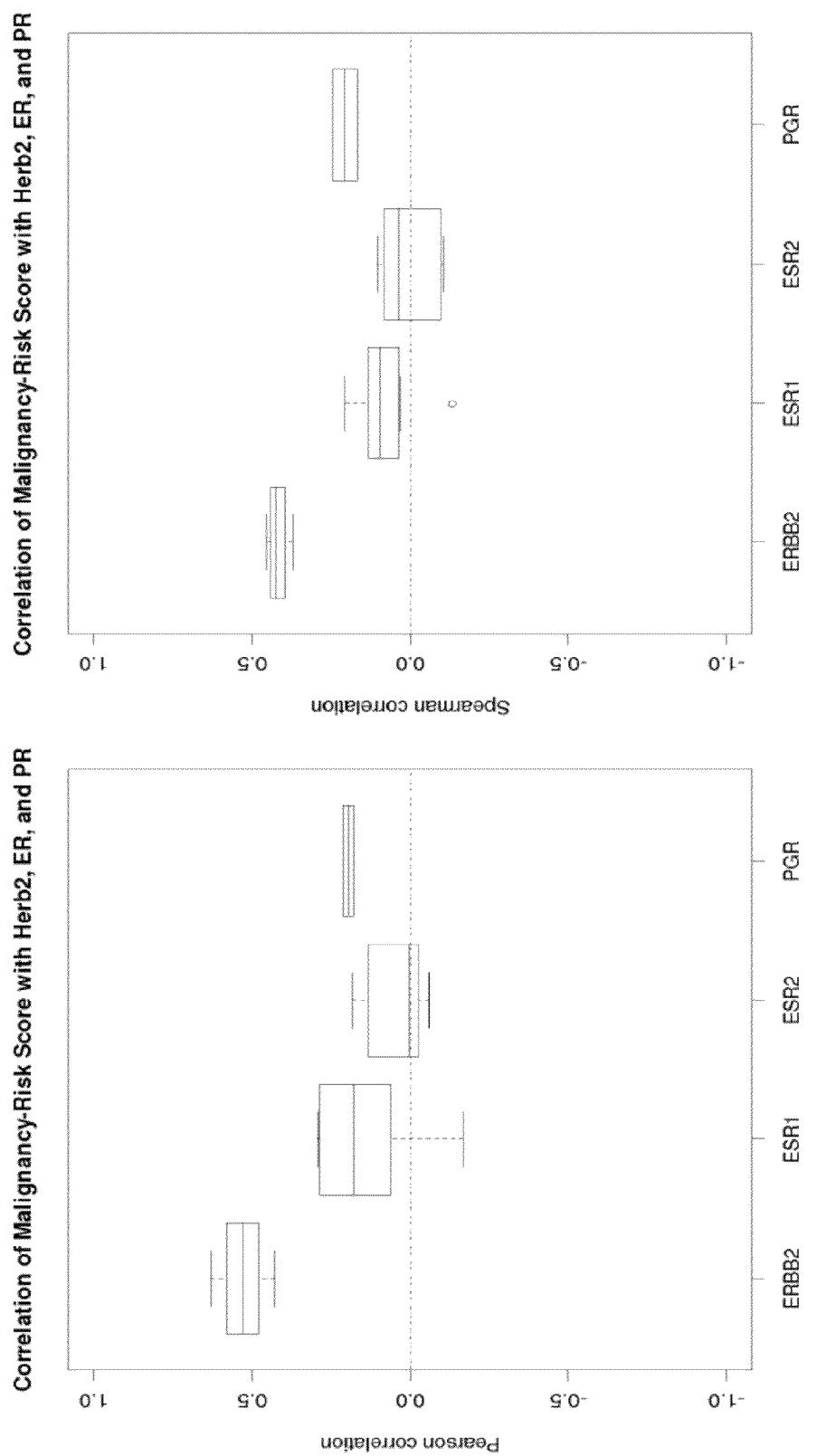
FIG. 26A depicts the distribution of correlation of ER, PR, and Herb2 genes with malignancy-risk score (Pearson and Spearman correlation).

Since ER, PR, and Her2 are key markers in cancer development, we examined their correlation with the malignancy-risk score. Results showed only a weak correlation for ER and PR (r=0.2~0.3) and a moderate correlation with Her2 (r=0.37~0.47 by spearman correlation and r=0.43~0.63 by Pearson correlation), suggesting relative independence of the risk score from these biomarkers (FIG. 26)

Example 17

Higher Malignancy-Risk Score of IDC-Like Normal Tissues

Figure 27A:
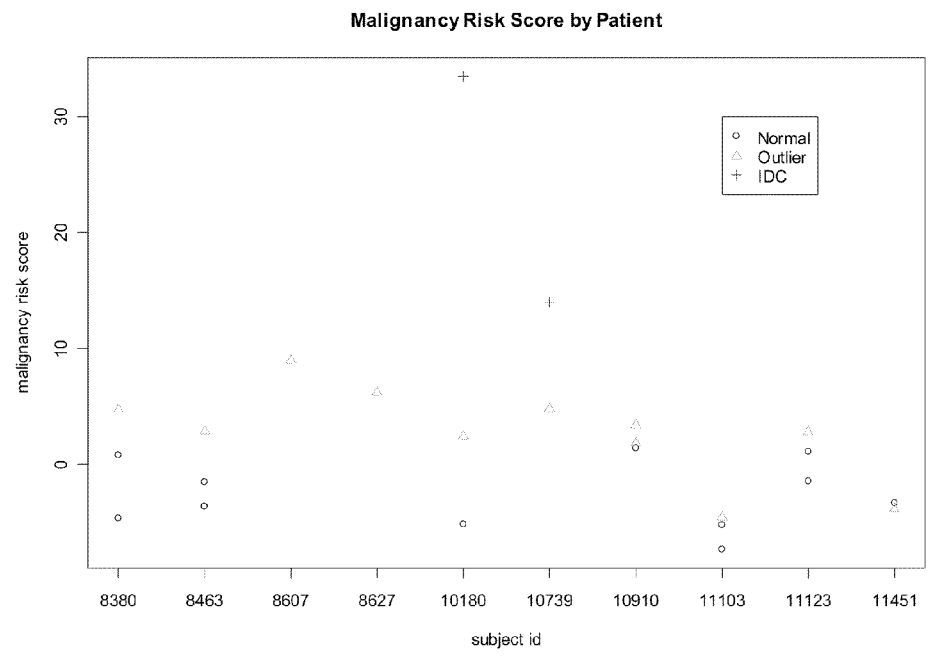
FIG. 27 shows the comparison of malignancy-risk score between IDC-like normal tissues, their matched normal tissues, and unmatched normal tissues.
Figure 27B:
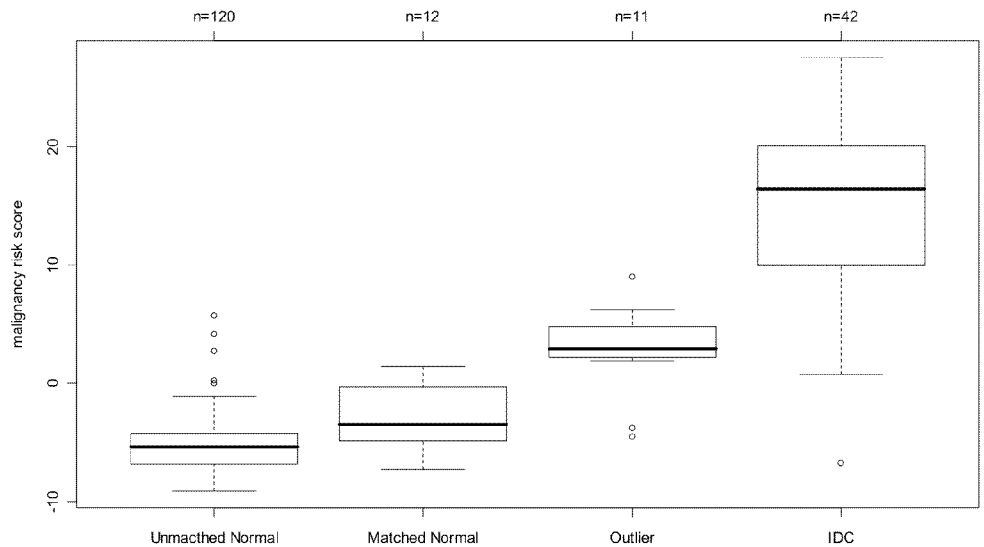
Figure 27C:
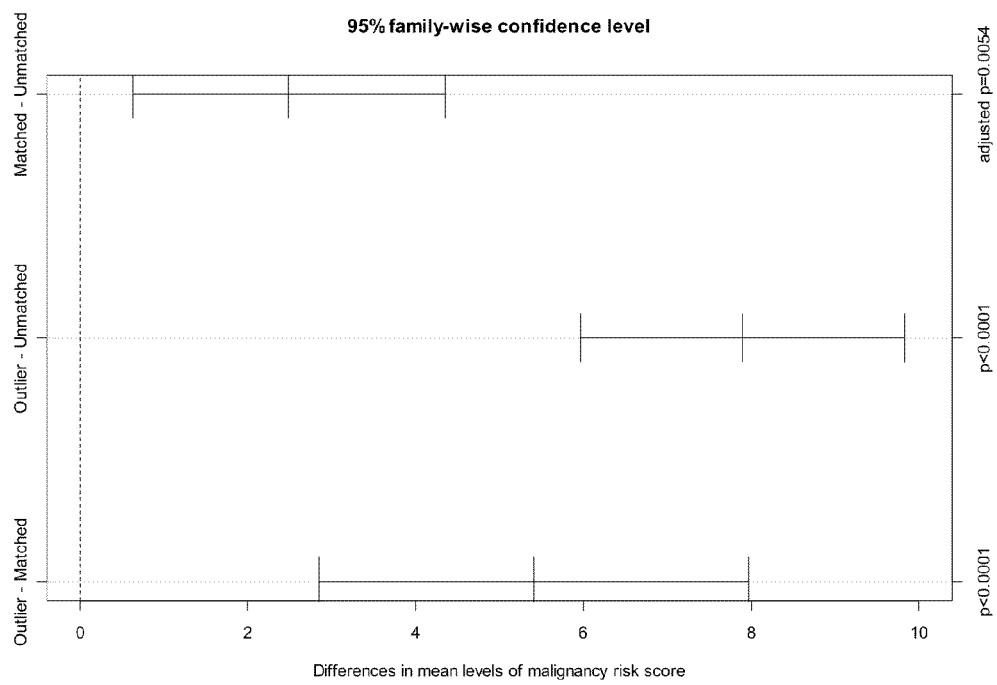

We identified 11 IDC-like normal tissues from 10 patients. There were another 12 normal tissues collected from the same 10 patients. These 12 normal tissues were molecularly and histologically normal and labeled as matched normal tissues to reflect they were derived from the same subject. The other normal tissues (n=120) from subjects without IDC-like normal tissues (i.e., not from the 10 subjects) were also molecularly and histologically normal and labeled as unmatched normal tissues for distinction. We found the malignancy-risk score was higher in the IDC-like normal tissues and the matched normal tissues than in the unmatched normal tissues. Difference of the risk score was statistically significant for (a) IDC-like normal tissues versus the matched normal tissues (adjusted p value <0.0001 using the Tukey method) and (b) matched versus unmatched normal tissues (adjusted p value=0.0054). An increasing trend of the malignancy-risk score was also seen from the unmatched normal tissues, the matched normal tissue, to the IDC-like normal tissues at the pooled data level (Pearson correlation=0.63 with p<0.0001; FIG. 27). Moreover, among the 10 patients with IDC-like normal tissues, analysis results showed a higher malignancy-risk score in the IDC-like normal tissues than in the matched normal tissues at subject level (p=0.01 using the random effect model; FIG. 27). Since the malignancy-risk score was derived without knowing subject information, a trend of the risk score decreasing from the IDC-like normal tissues, to the matched normal tissue, to the unmatched normal tissues would not be expected.

Example 18

RT-PCR Validation of Malignancy-Risk Genes

Figure 28:
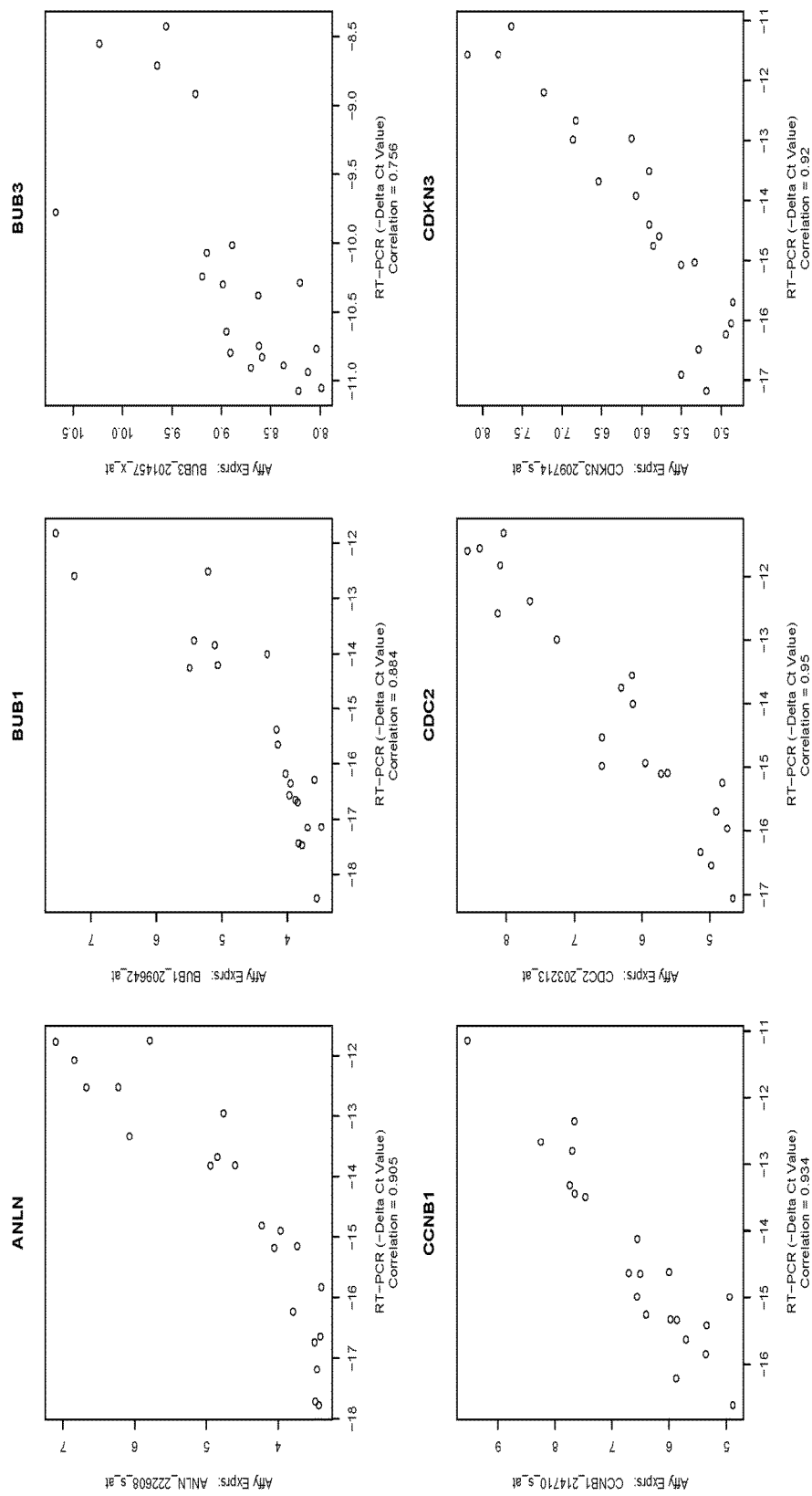
FIG. 28 shows the Correlation plot of RT-PCR versus microarray for the 30 malignancy-risk genes.
Figure 29:
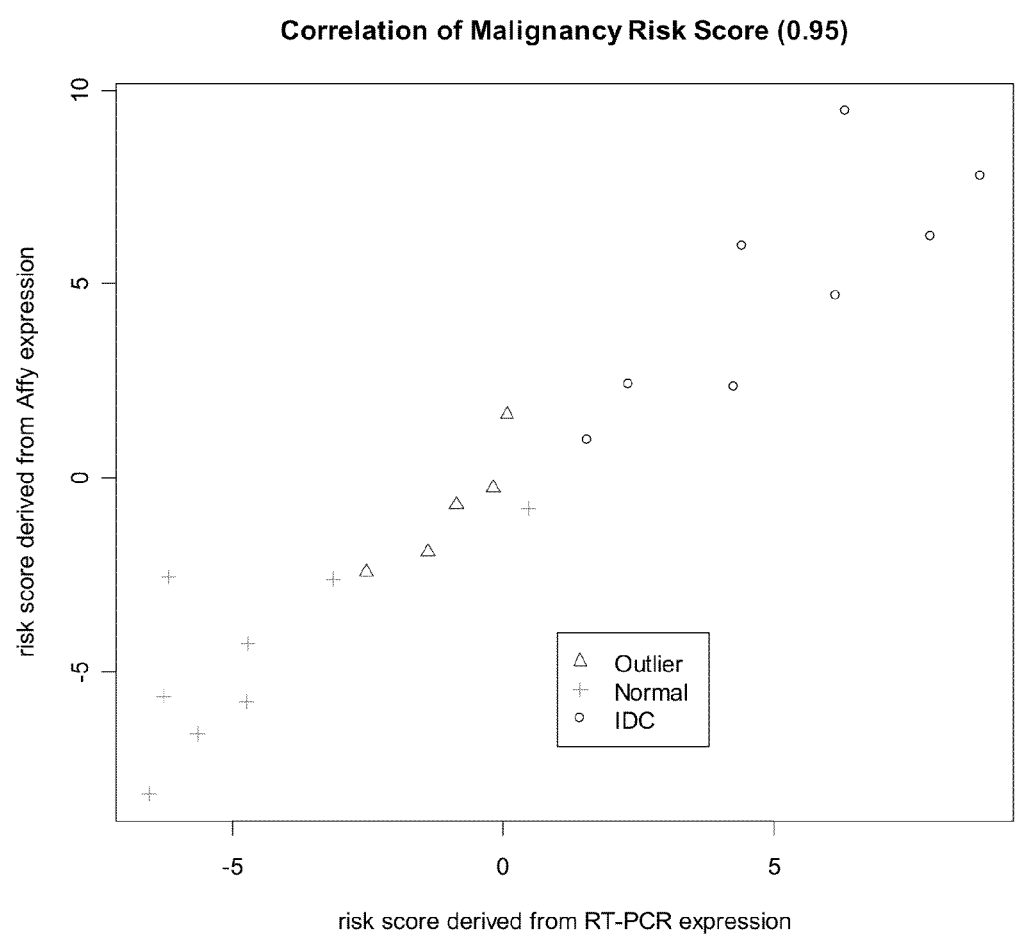
FIG. 29 is a graph showing the correlation of the malignancy-risk score derived from RT-PCR expression with the malignancy-risk score derived from Affymetrix gene expression assays.

Expression of the 30 selected malignancy-risk signature genes identified by microarray profiling was successfully validated by RT-PCR. The 30 genes were selected based on expression and biological relevance. There were 27 genes showing a strong Pearson correlation >0.7 (correlation >0.9: 12 genes, 0.8-0.9: 13, and 0.7-0.8: 2; the p values were <0.0001) (FIG. 28). The composite malignancy-risk score (based on microarray data from 30 genes) also demonstrated a very high correlation (0.95) with RT-PCR results. The risk score for the IDC-like normal tissues fell in the middle between the IDC and normal samples (FIG. 29).

Examples 19-21 describe the clinical association of malignancy-risk signature with cancer risk, cancer relapse/progression, and prognosis. We assessed the malignancy-risk score on three additional external independent datasets (see also Examples 8-12). Statistical procedures were described in Statistical Methods Section. These external datasets as well as the datasets presented in Examples 8-12 permitted the evaluation of a number of properties of the malignancy-risk signature including cancer risk, cancer relapse/progression, and cancer prognosis. Table 9 summarizes the results for all these datasets.

Example 19

Chanrion et al's Relapse Study[22]

Relapse of tamoxifen-treated primary breast cancers: (GEO: GSE9893)

Background: There were 155 patients (52 patients with relapse (R) and 103 patients with relapse-free (RF) who received adjuvant tamoxifen. The primary tumors from these patients were analyzed for expression profiles at the whole-genome level by 70-mer oligonucleotide microarrays (22,656 genes). There were 61 genes in common with the malignancy-risk gene signature, which was used to calculate the malignancy-risk score.

Results: Analysis by a median cutoff of the risk score (i.e., high risk with score >median and low risk with score <median) showed a significant association of the malignancy-risk score with the relapse of primary breast cancers (logistic regression: OR=7.82 with p<0.0001) Similarly, two sample t-test showed a statistically significant difference of the risk score between relapse versus relapse-free (p<0.0001; see FIG. 34A). Moreover, univariate analysis based on two-sample test showed most genes with p<0.05 (50 out of 61 genes; 82%; in contrast to 60% genes with p<0.05 when using all the 22,656 genes; see FIG. 34B).

Example 20

Wang et al's Breast Cancer Relapse Free Survival Study[23]

Background: The data includes 286 lymph-node negative breast patients with metastasis-free survival as clinical survival outcome. A 76 gene signature was derived from this dataset to predict distant metastasis. The microarray platform was Affymetrix Human U133a GeneChips. We normalized data using quantile-quantile method. There were 102 probe sets (from the ~20K probe sets) in common with the malignancy-risk gene signature. There were only 4 genes in common (FIG. 35A) between the 76 gene signature and the malignancy-risk gene signature.

Data analysis: We compared performance of survival analysis for the 3 gene signatures (malignancy-risk signature, 76 gene signature, and 4 genes in common) based on the malignancy-risk score.

Malignancy-risk score: We first evaluated the overall performance of the 102 probe sets for the malignancy-risk gene signature. The risk score was calculated by converting expression of the genes into the first principal component score (based on principal component analysis method; see Statistical Methods). We used median of the risk score as cutoff to dichotomize the 286 patients into two risk groups. Log-rank test showed a significant separation of KM survival curves between the two risk groups ($\chi2$=12.6; p=0.0004). The risk score was calculated in the same way for the 76 gene signature and 4 common genes, respectively. Univariate Cox proportional hazards model was also used to test individual gene effect (of the 102 genes) on the metastasis-free survival.

Figure 35C:
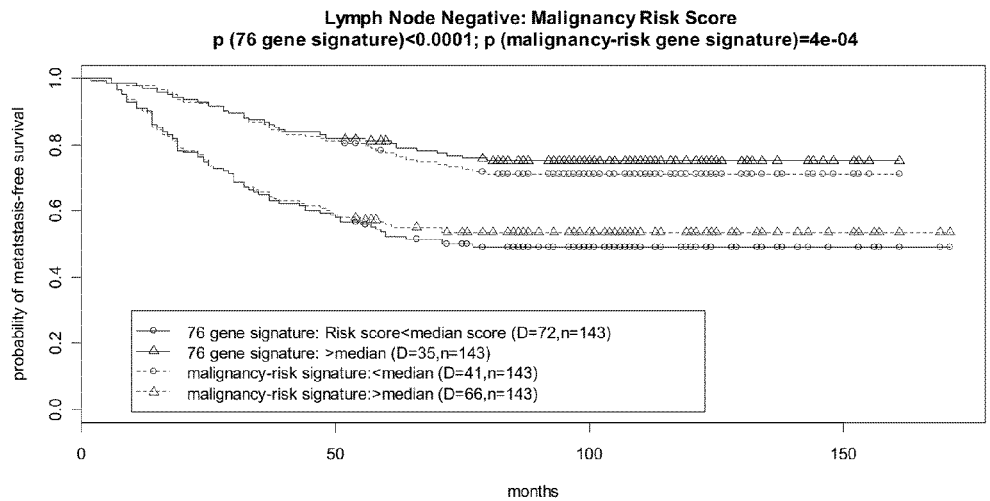
FIG. 35C depicts a graph of the malignancy-risk score based on the 76 gene signature.
Figure 35D:
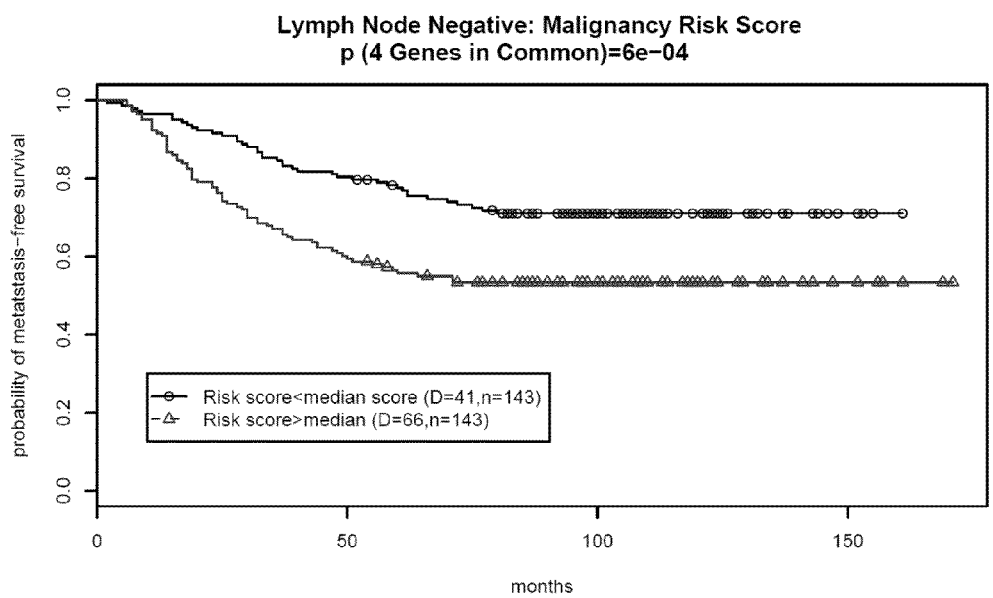
FIG. 35D depicts a graph of the malignancy-risk score based on the 4 gene signature.

Results: The three gene signatures performed well to separate survival curves of the two risk groups (FIG. 35C-D). The 76 gene signature performed the best because the signature was derived from this dataset (FIG. 35C). However, the performance for the malignancy-risk signature was almost comparable to the 76 gene signature. Even for the 4 genes in common, it also had a comparable performance (FIG. 35D). FIG. 35B listed 64 genes (of the 102 genes) with p value <0.05 based on the univariate analysis.

Example 21

Huang et al's Breast Lymph Node Study[24]

Background: The breast cancer microarray data reported by Huang et al. (Huang et al., 2003) contained 18 patients with positive lymph node (LN) and 19 patients with negative LN. The gene expressions were obtained from the Affymetrix human U95a chip. Data were pre-processed using RMA (Irizarry et al. 2003). There were 112 probe sets (82 unique genes) in common with the outlier gene signature.

Data analysis: We evaluated the association of the malignancy-risk gene signature with lymph node development using the malignancy-risk score and univariate analysis.

Figure 36B:
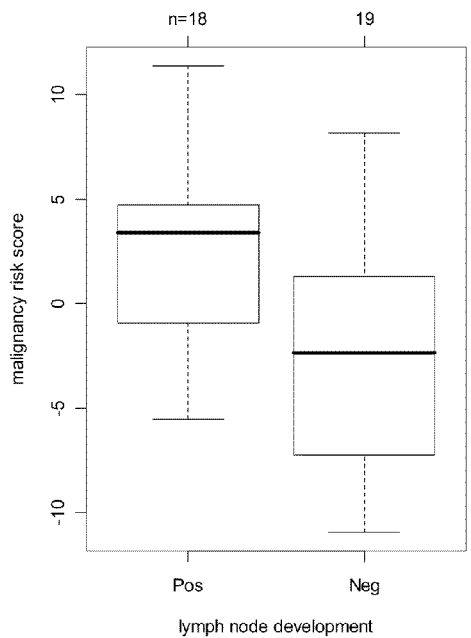
FIG. 36B depicts the difference of risk score between positive lymph node versus negative lymph node samples.

Results: 1. Malignancy-risk score: The malignancy-risk score was generated using expression data from the 112 probe sets. We used the median cutoff of the risk score to dichotomize patients into two risk groups: high risk with score >median and low risk with score <median. Logistic regression model showed a significant association of the median cutoff malignancy-risk score with the LN status (logistic regression: OR=7.29 with p=0.007). Similarly, two sample t-test showed a statistically significant difference of risk score between positive LN versus negative LN (p=0.004) (FIG. 36B).

2. Univariate analysis: There were 34 probe sets (34/122=30%) with p value <0.05 (two-sample t-test) (FIG. 36A). In contrast, there were only 7% genes (912 out of 12625 probe sets) with p<0.05 when using all probe sets. Fisher exact test showed a highly statistical significance (p<0.0001), indicating that it is unlikely by chance to have such large proportion of significant genes (30%).

Summary: Results suggested that the outlier gene signature was associated with lymph node development (LN positive tends to have a higher malignancy-risk score).

Discussion

Identification of normal tissue at risk for malignant conversion has great potential application in clinical practice, in both evaluating the risk associated with routine breast biopsies as well as the risk of local recurrence following lumpectomy. Detecting these high-risk normal appearing tissues, however, remains a challenging task. In one aspect of this invention, we developed an innovative approach to identify histologically-normal, but molecularly-abnormal tissue "at risk" for malignant degeneration. One rationale, to which the inventors are not bound, is that a histologically-normal tissue with "tumor-like" gene expression pattern might harbor substantial risk for future cancer development. Genes associated with these high-risk tissues were referred to as "malignancy-risk genes". Based on this rationale, we identified 11 "IDC-like" normal tissues (out of 143 normal breast tissues) and developed the malignancy-risk gene signature and risk score.

Figure 5:
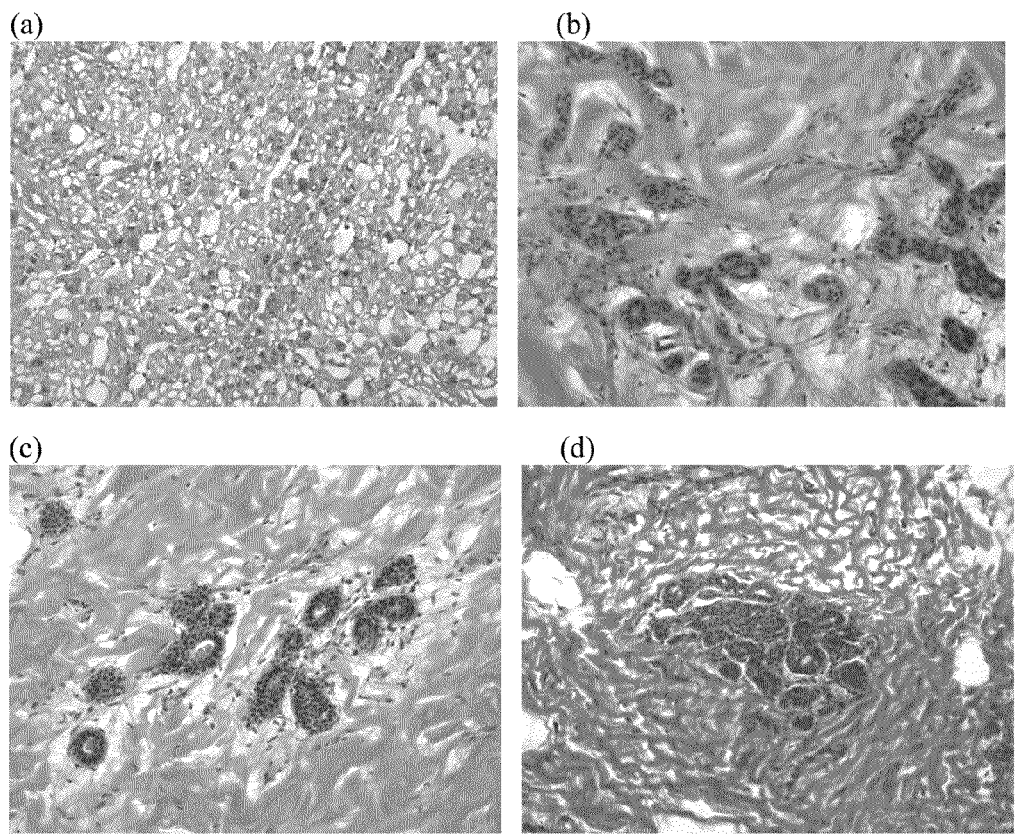
FIG. 5 shows histologic images of representative frozen breast tissues (original magnification×200): (a) Invasive ductal carcinoma (IDC) showing sheets of tumor cells and stromal strands, (b) Histologically normal breast lobule in a frozen breast tissue specimen that was collected at 1 cm from the tumor (IDC) shown in Figure A. This specimen was designated as 'outlier normal' based on its molecular profile, (c) Histologically normal breast lobule in a frozen breast tissue specimen that was collected at 2 cm from the tumor (IDC) shown in Figure (a), (d) Histologically normal breast lobule in a frozen breast tissue specimen that was collected from a different case of IDC.

A careful re-examination of all the IDC-like normal tissues showed that they were histologically-normal, with no evidence of in situ or invasive carcinoma of the breast, and no atypia (FIGS. 4-5). However, these IDC-like normal tissues showed gene expression profiles resembling invasive carcinomas, indicating that these tissues had already acquired the molecular fingerprint of cancer and, therefore, may be at increased risk for subsequent cancer development. Moreover, from these IDC-like normal tissues, we developed a "malignancy-risk" gene signature that may serve as a marker of subsequent risk of breast cancer development. The malignancy-risk gene signature was internally validated by RT-PCR and leave-one-out cross validation. Analysis of external datasets also demonstrated its clinical relevance to cancer-risk, cancer relapse/progression, and prognosis. This is an intriguing finding with substantive clinical implications. While several studies may have suggested that cell cycle/proliferation are one of the hallmarks of existing cancer[25-28], this is the first study to suggest the proliferative program of gene expression may be the earliest detectable event in normal breast tissues at risk for developing breast cancer. A recently reported study of 14 normal breast tissues from breast cancer cases identified genes differentially expressed in these tissues versus normal breast reduction mammoplasties, but did not decipher a predominantly proliferative gene function[18]. The large preponderance of proliferative genes in the malignancy-risk gene set was not expected. By comparison, IDC associated genes were biased towards both proliferative and adhesive gene sets. These findings suggest a temporal relationship between proliferative and adhesive gene expression programs, with the former being precursors to histological alterations and responsible for malignancy-risk. There was also no statistical association of the IDC-like normal tissues with ER/PR, Her2/neu, and grade suggesting the malignancy-risk signature may be not be dependent on these factors. The lack of association of the IDC-like normal tissues with the triple negative (ER/PR/Her2Neu) phenotype also suggests no link to BRCA1 and BRCA2.

Evaluation on external independent datasets demonstrated the clinical relevance of the malignancy-risk gene signature not only to cancer risk, but also to cancer relapse/progression, and prognosis. As such, the signature has promise for impacting clinical decisions. These include altering strategies for follow-up of histologically-normal, but molecularly abnormal breast biopsies, determining which patients might benefit from radiotherapy following lumpectomy, or determining which patients might benefit from mastectomy due to multi-focal disease risk.

REFERENCES

1. Kaplan, J., et al. Breast conservation in patients with multiple ipsilateral synchronous cancers. *Journal of the American College of Surgeons* 197, 726-729 (2003).
2. Fisher, B., et al. Ten-year results of a reandomized clinical trial comparing radical mastectomy and total mastectomy with or without radiation. *New England Journal of Medicine* 312, 674-681 (1985).
3. Price, P., et al. Duct carcinoma insitu: predictors of local recurrence and progreassion in patients treated by surgery alone. *British Journal of Cancer* 61, 869-872 (1990).
4. Page, D. L., Dupont, W. D., Rogers, L. W., Jensen, R. A. & Schuyler, P. A. Continued local recurrence of carcinoma 15-25 years after a diagnosis of low-grade ductal carcinoma in-situ of the breast treated only by biopsy. *Cancer* 76, 1197-1200 (1995).
5. Fredriksson, I., et al. Risk factors for local recurrence after breast-conserving surgery. *British Journal of Surgery* 90, 1093-1102 (2003).
6. Shah, V. I., et al. False-negative core needle biopsies of the breast—An analysis of clinical, radiologic, and pathologic findings in 27 consecutive cases of missed breast cancer. *Cancer* 97, 1824-1831 (2003).
7. Tusher, V. G., Tibshirani, R. & Chu, G. Significance analysis of microarrays applied to the ionizing radiation response. *Proceedings of the National Academy of Sciences of the United States of America* 98, 5116-5121 (2001).
8. Whitfield, M. L., et al. Identification of genes periodically expressed in the human cell cycle and their expression in tumors. *Molecular Biology of the Cell* 13, 1977-2000 (2002).
9. Turashvili, G., et al. Novel markers for differentiation of lobular and ductal invasive breast carcinomas by laser microdissection and microarray analysis. *Bmc Cancer* 7 (2007).
10. Ma, X. J., et al. Gene expression profiles of human breast cancer progression. *Proceedings of the National Academy of Sciences of the United States of America* 100, 5974-5979 (2003).
11. Poola, I., et al. Identification of MMP-1 as a putative breast cancer predictive marker by global gene expression analysis. *Nature Medicine* 11, 481-483 (2005).
12. van de Vijver, M. J., et al. A gene-expression signature as a predictor of survival in breast cancer. *New England Journal of Medicine* 347, 1999-2009 (2002).
13. Hartigan J A, W. M. A K-Means Clustering Algorithm. *Applied Statistics* 28, 100-108 (1979).
14. Breiman, L., Friedman, J., Olshen, R. & Stone, C. *Classification and Regression Trees*, (Wadsworth & Brooks, Monterey, Calif., 1984).
15. Carter, S. L., Eklund, A. C., Kohane, I. S., Harris, L. N. & Szallasi, Z. A signature of chromosomal instability inferred from gene expression profiles predicts clinical outcome in multiple human cancers. *Nature Genetics* 38, 1043-1048 (2006).
16. Tuttle, T. M., Habermann, E., Grund, E., Morris, T. & Virnig, B. Increasing use of contralateral prophylactic mastectomy among breast cancer patients: a trend toward more aggressive surgical treatment. *Annals of Surgical Oncology* 14, 7-7 (2007).
17. Robbins, P., et al. Histological grading of breast carcinomas—a study of interobserver agreement. *Human Pathology* 26, 873-879 (1995).
18. Tripathi A, King C, de la Morenas A, Perry V K, Burke B, Antoine G A, et al. Gene expression abnormalities in histologically normal breast epithelium of breast cancer patients. Int J Cancer 2008; 122(7):1557-66.
19. Irizarry R A, Bolstad B M, Collin F, Cope L M, Hobbs B, Speed T P. Summaries of Affymetrix GeneChip probe level data. In: Nucleic Acids Res; 2003. p. e15.
20. Tusher V G, Tibshirani R, Chu G. Significance analysis of microarrays applied to the ionizing radiation response. Proceedings of the National Academy of Sciences of the United States of America 2001; 98(9):5116-5121.
21. Miller R G. Simultaneous Statistical Inference: Springer; 1981.
22. Chanrion M, Negre V, Fontaine H, Salvetat N, Bibeau F, Mac Grogan G, et al. A gene expression signature that can predict the recurrence of tamoxifen-treated primary breast cancer. Clin Cancer Res 2008; 14(6):1744-52.
23. Wang Y, Klijn J G, Zhang Y, Sieuwerts A M, Look M P, Yang F, et al. Gene-expression profiles to predict distant metastasis of lymph-node-negative primary breast cancer. Lancet 2005; 365(9460):671-9.
24. Huang E, Cheng S H, Dressman H, Pittman J, Tsou M H, Horng C F, et al. Gene expression predictors of breast cancer outcomes. Lancet 2003; 361(9369):1590-6.
25. Sorlie T, Perou C M, Tibshirani R, Aas T, Geibreast cancerr S, Johnsen H, et al. Gene expression patterns of breast carcinomas distinguish tumor subclasses with clinical implications. Proc Natl Acad Sci USA 2001; 98(19): 10869-74.
26. Rosenwald A, Wright G, Wiestner A, Chan W C, Connors J M, Campo E, et al. The proliferation gene expression signature is a quantitative integrator of oncogenic events that predicts survival in mantle cell lymphoma. Cancer Cell 2003; 3(2):185-97.
27. Whitfield M L, George L K, Grant G D, Perou C M. Common markers of proliferation. Nat Rev Cancer 2006; 6(2):99-106.
28. Chung C H, Bernard P S, Perou C M. Molecular portraits and the family tree of cancer. Nat Genet 2002; 32 Suppl: 533-40.

TABLE 1

Pathological data of the patients used in the study, including ER, PR, Her2, and grade.

| ER/PR/Her2 status | ER | PR | Her2/neu |
|---|---|---|---|
| Negative | 25 | 38 | 43 |
| Positive | 55 | 42 | 12 |
| other* | 10 | 10 | 35 |
| Total cases | 90 | 90 | 90 |

| Grade | frequency |
|---|---|
| Well differentiated | 6 |
| Moderately differentiated | 27 |
| Poorly differentiated | 30 |
| Undifferentiated/anaplastic | 10 |
| No grade | 17 |
| Total cases | 90 |

*Results not available

Table 2: Distribution of tumor and normal tissues by subject and their geographical locations relative to the incident tumor, as well as their graphical representation.

TABLE 2A

Distribution of tumor and normal tissues per case and their geographical locations relative to the incident tumor.

| ID | Tumor site | Ipsilateral breast Zone 1 | 2 | 3 | 4 | 5 | Contralateral breast Zone 1 | 2 | 3 | 4 | 5 | Number of tissues Normal | IDC-like normal | Tumor |
|---|---|---|---|---|---|---|---|---|---|---|---|---|---|---|
| 7369 | | | | N | N | N | | | | | | 3 | 0 | 0 |
| 7397 | | N | | N | | N | | | | | | 3 | 0 | 0 |
| 7619 | | | N | N | | | | | | | | 2 | 0 | 0 |
| 7954 | | | | N | | | | | | | | 1 | 0 | 0 |
| 8380 | N | | O | | N | | | | | | | 2 | 1 | 0 |
| 8456 | | N | N | N | N | | | | | | | 4 | 0 | 0 |
| 8463 | | N | O | N | N | | | | | | | 3 | 1 | 0 |
| 8513 | | T* | | | | | | | | | | 0 | 0 | 1 |
| 8514 | | | | | N | N | | | | | | 2 | 0 | 0 |
| 8542 | T | | | | | | | | | | | 0 | 0 | 1 |
| 8607 | O | | | | | | | | | | | 0 | 1 | 0 |
| 8608 | | | N | | N | | | | | | | 2 | 0 | 0 |
| 8615 | | N | | N | N | | | N | | N | | 5 | 0 | 0 |
| 8626 | | N | | | | | | | | | | 1 | 0 | 0 |
| 8627 | | | O | | | | | | | | | 0 | 1 | 0 |
| 8628 | | N | | | | | | | | | | 1 | 0 | 0 |
| 8636 | T, T, T | | | | | | | | | | | 0 | 0 | 3 |
| 8642 | T, T, T, T | | T* | | | | | | | | | 0 | 0 | 5 |
| 8653 | | N | | | N | | | | | | | 2 | 0 | 0 |
| 8669 | | | | | N | | | | | | | 1 | 0 | 0 |
| 8671 | | | | | N | N | | | | | | 2 | 0 | 0 |
| 8672 | T | | | | | | | | | | | 0 | 0 | 1 |
| 8689 | | | | N | | | | | | | | 1 | 0 | 0 |
| 8696 | | N | N | N | | | | | | | | 3 | 0 | 0 |
| 8703 | T, T | | | | N | N | | | | | | 2 | 0 | 2 |
| 8706 | | | | | N | | | | | | N | 2 | 0 | 0 |
| 8717 | | | N | | | | | | | | | 1 | 0 | 0 |
| 8721 | | | | | N | | | | | | | 1 | 0 | 0 |
| 8735 | | N | | | | | | N | | | | 2 | 0 | 0 |
| 8803 | | N | | N | N | | | | N | N | | 5 | 0 | 0 |
| 8862 | T | | | | | | | | | | | 0 | 0 | 1 |
| 8880 | | | | | N | | | | | | | 1 | 0 | 0 |
| 8881 | | | | | N | | | | | | | 1 | 0 | 0 |
| 8936 | T | | | | | | | | | | | 0 | 0 | 1 |
| 9097 | T | | | | | | | | | | | 0 | 0 | 1 |
| 9100 | | N | | N | | | | | | | | 2 | 0 | 0 |
| 9112 | | | | | N | N | | | | | | 2 | 0 | 0 |
| 9393 | | | | N | | | | | | | | 1 | 0 | 0 |
| 9740 | T | | N | T* | N | | | | | | | 2 | 0 | 2 |
| 9744 | | | | | N | | | | | | | 1 | 0 | 0 |
| 10143 | T | | T* | | | | | | | | | 0 | 0 | 2 |
| 10176 | | | N | N | N | | | | | | | 3 | 0 | 0 |
| 10180 | T | | | O | N | | | | | | | 1 | 1 | 1 |
| 10443 | | | | N | | | | | | | | 1 | 0 | 0 |
| 10473 | T | | | | | N | | | | | | 1 | 0 | 1 |
| 10475 | | N | N | N | | | | | | | | 3 | 0 | 0 |
| 10481 | | N | | | | | | | | | | 1 | 0 | 0 |
| 10496 | T | | N | | | | | | | | | 1 | 0 | 1 |

TABLE 2A-continued

Distribution of tumor and normal tissues per case and their geographical locations relative to the incident tumor.

| ID | Tumor site | Ipsilateral breast Zone 1 | 2 | 3 | 4 | 5 | Contralateral breast Zone 1 | 2 | 3 | 4 | 5 | Number of tissues Normal | IDC-like normal | Tumor |
|---|---|---|---|---|---|---|---|---|---|---|---|---|---|---|
| 10535 |   | N |   |   |   |   |   |   |   |   |   | 1 | 0 | 0 |
| 10559 |   |   |   | N |   |   |   |   |   |   |   | 1 | 0 | 0 |
| 10563 |   |   |   | N |   |   |   |   |   |   |   | 1 | 0 | 0 |
| 10584 |   |   |   | N |   |   |   |   |   |   |   | 1 | 0 | 0 |
| 10608 |   |   | N | N | N | N |   |   |   |   |   | 4 | 0 | 0 |
| 10650 |   |   |   | N |   |   |   |   |   |   |   | 1 | 0 | 0 |
| 10686 | T |   |   |   |   |   |   |   |   |   |   | 0 | 0 | 1 |
| 10739 | T |   |   |   | O |   |   |   |   |   |   | 0 | 1 | 1 |
| 10781 | T |   | T* |   |   |   |   |   |   |   |   | 0 | 0 | 2 |
| 10786 | T |   |   |   |   |   |   |   |   |   |   | 0 | 0 | 1 |
| 10874 |   | N |   |   |   |   |   |   |   |   |   | 1 | 0 | 0 |
| 10910 |   |   | N | O | O |   |   |   |   |   |   | 1 | 2 | 0 |
| 10918 | T |   |   |   |   |   |   |   |   |   |   | 0 | 0 | 1 |
| 10928 | T |   |   |   |   |   |   |   |   |   |   | 0 | 0 | 1 |
| 10957 | T |   |   |   |   |   |   |   |   |   |   | 0 | 0 | 1 |
| 10962 | N* |   |   |   |   |   |   |   |   |   |   | 1 | 0 | 0 |
| 10964 |   | N | N |   | N |   |   |   |   |   |   | 3 | 0 | 0 |
| 11003 |   |   | N | N | N |   |   |   |   |   |   | 3 | 0 | 0 |
| 11063 | T |   | N |   | N | N |   |   |   |   |   | 3 | 0 | 1 |
| 11103 |   | N | O |   | N |   |   |   |   |   |   | 2 | 1 | 0 |
| 11123 |   |   | N | O | N |   |   |   |   |   |   | 2 | 1 | 0 |
| 11147 | T | N |   |   |   |   |   |   |   |   |   | 1 | 0 | 1 |
| 11196 |   |   | N | N | N | N |   |   |   |   |   | 4 | 0 | 0 |
| 11209 |   | N | N |   |   |   |   |   |   |   |   | 2 | 0 | 0 |
| 11286 | T |   |   |   |   |   |   |   |   |   |   | 0 | 0 | 1 |
| 11320 |   |   | N | N |   |   |   |   |   |   |   | 2 | 0 | 0 |
| 11354 |   | N |   | N | N | N |   |   |   |   |   | 4 | 0 | 0 |
| 11365 | T |   |   |   |   |   |   |   |   |   |   | 0 | 0 | 1 |
| 11451 |   |   | N |   | O |   |   |   |   |   |   | 1 | 1 | 0 |
| 11455 | T |   | N |   |   |   |   |   |   |   |   | 1 | 0 | 1 |
| 11464 |   | N |   | N |   |   |   |   |   |   | N | 3 | 0 | 0 |
| 11472 |   | N |   | N | N |   |   |   |   |   |   | 3 | 0 | 0 |
| 11478 | T, T |   |   |   | N |   |   | N | N |   |   | 3 | 0 | 2 |
| 11545 |   |   |   |   | N |   |   |   |   |   |   | 1 | 0 | 0 |
| 11580 | T |   |   | N | N | N |   |   |   |   |   | 3 | 0 | 1 |
| 11640 |   | N |   |   |   |   |   |   |   |   |   | 1 | 0 | 0 |
| 11688 | T |   |   |   | T* |   |   |   |   |   |   | 0 | 0 | 2 |
| 11689 |   |   |   |   | N |   |   |   |   |   |   | 1 | 0 | 0 |
| 11693 |   |   | N |   |   |   |   |   |   |   |   | 1 | 0 | 0 |
| 11732 |   |   | N |   | N | N |   |   |   |   |   | 3 | 0 | 0 |
| 11770 | T |   |   |   |   |   |   |   |   |   |   | 0 | 0 | 1 |
| 11792 |   | N |   |   |   |   |   |   |   |   |   | 1 | 0 | 0 |

N* = histological normal, but sampled as tumor
T* = histological tumor, but sampled as normal
O: IDC-like normal

TABLE 2B

Frequency of cases with number of IDC and normal tissues

| normal tissue per cases \ tumor tissue per case | 0 | 1 | 2 | 3 | 5 |
|---|---|---|---|---|---|
| 0 | 0 | 14 | 3 | 1 | 1 |
| 1 | 27 | 5 | 0 | 0 | 0 |
| 2 | 12 | 1 | 2 | 0 | 0 |
| 3 | 14 | 2 | 1 | 0 | 0 |
| 4 | 5 | 0 | 0 | 0 | 0 |
| 5 | 2 | 0 | 0 | 0 | 0 |

60 cases with normal tissue(s) only
19 cases with tumor tissue(s) only
11 cases with at least one tumor and one normal tissue
A total of 90 cases with 143 normal tissues and 42 IDCs.

TABLE 3

A list of 30 malignancy-risk genes for RT-PCR validation

| Gene name | Affymetrix probe set id |
|---|---|
| ANLN | 222608_s_at |
| BUB1 | 209642_at |
| BUB3 | 201457_x_at |
| CCNB1 | 214710_s_at |
| CDC2 | 203213_at |
| CDKN3 | 209714_s_at |
| CENPA | 204962_s_at |
| CENPF | 207828_s_at |
| CKS2 | 204170_s_at |
| DPP3 | 218567_x_at |
| DTL | 218585_s_at |
| FOXM1 | 202580_x_at |
| HN1 | 217755_at |
| KPNA2 | 211762_s_at |

TABLE 3-continued

A list of 30 malignancy-risk genes for RT-PCR validation

| Gene name | Affymetrix probe set id |
|---|---|
| MELK | 204825_at |
| MLF1IP | 218883_s_at |
| NDC80 | 204162_at |
| NME | 201577_at |
| NUSAP1 | 218039_at |
| PAFAH1B3 | 203228_at |
| PBK | 219148_at |
| PCNA | 201202_at |
| PRC1 | 218009_s_at |
| RACGAP1 | 222077_s_at |
| RRM2 | 201890_at |
| SMC4 | 201663_s_at |
| SQLE | 209218_at |
| TK1 | 202338_at |
| TOP2A | 201291_s_at |
| TYMS | 1554696_s_at |

Table 4: Simulation Study to Evaluate the Outlier Tissue (IDC-Like Normal Tissue) Approach.

TABLE 4A

Predictive Value Positive (PV+) versus Sensitivity.

| | | Fact | |
|---|---|---|---|
| | | Outlier normal tissue | Normal tissue |
| Test | Classify as outlier tissue | a | c |
| | Classify as normal tissue | b | d |

PV+ (= a/(a + c)): Probability of a selected normal tissue as an outlier tissue.
Sensitivity (= a/(a + b)): Probability of an outlier normal tissue being selected.

TABLE 4B

Sensitivity and PV+ of identification of outlier tissue over 100 simulations.

| Proportion of significant genes | Sensitivity | PV+ |
|---|---|---|
| 1% | 80.3% | 100% |
| 2% | 81.3% | 100% |
| 3% | 82.4% | 100% |
| 4% | 83.9% | 100% |
| 5% | 84.4% | 100% |
| 6% | 84.0% | 100% |
| 7% | 85.9% | 100% |
| 8% | 86.5% | 100% |
| 9% | 86.9% | 100% |
| 10% | 91.3% | 100% |

TABLE 5

Frequency of ER/PR/Her2/Grade for the patients with IDC-like normal tissues and the patients with the remaining normal tissues (labeled as non-IDC-like normal)

| | ER | | PR | | Her2/neu | |
|---|---|---|---|---|---|---|
| Type | Patients with non-IDS-like normal | Patients with IDC-like normal | Patients with non-IDC-like normal | Patients with IDC-like normal | Patients with non-IDC-like normal | Patients with IDC-like normal |
| Negative | 16 | 5 | 25 | 4 | 26 | 3 |
| Positive | 36 | 4 | 27 | 5 | 7 | 2 |
| Total available cases* | 52 | 9 | 52 | 9 | 33 | 5 |
| p value** | 0.25 | | 0.73 | | 0.57 | |

*Cases with negative or positive results
**p value was calculated using the Fisher exact test

| Grade Description | Patients with non-IDC-like normal | Patients with IDC-like normal |
|---|---|---|
| Well differentiated | 6 | 0 |
| Moderately differentiated | 16 | 4 |
| Poorly differentiated | 20 | 1 |
| Undifferentiated/anaplastic | 6 | 2 |
| Total available cases | 48 | 7 |
| p value* | | 0.21 |

*p value was calculated using the Fisher exact test.

| | Patients with non-IDS-like normal | Patients with IDC-like normal |
|---|---|---|
| Age < 50 | 26 | 6 |
| Age > 50 | 31 | 3 |
| Total available cases | 57 | 9 |
| p value* | | 0.30 |

*p value was calculated using the Fisher exact test.

TABLE 6

Malignancy-risk gene list.

| Affy probe set id | Gene Symbol | Fold change | FDR | Regulation | DNA replication | Mitosis | Poola et al | Turashvili et al | Chauvrion et al | Ma et al | van't Veer et al | Wang et al | Huang et al | Gene Title |
|---|---|---|---|---|---|---|---|---|---|---|---|---|---|---|
| 222608_s_at | ANLN | 4.01 | <0.01 | Up-Regulated | | Y | | | Y | Y | Y | | | anillin, actin binding protein (scraps homolog, *Drosophila*) |
| 206632_s_at | APOBEC3B | 3.11 | <0.01 | Up-Regulated | | | | | | | | | | apolipoprotein B mRNA editing enzyme, catalytic polypeptide-like 3B |
| 208750_s_at | ARF1 | 2.05 | <0.01 | Up-Regulated | | | | | Y | | | | | ADP-ribosylation factor 1 |
| 201096_s_at | ARF4 | 2.16 | <0.01 | Up-Regulated | | | | | Y | | | | | ADP-ribosylation factor 4 |
| 216266_s_at | ARFGEF1 | 2.43 | <0.01 | Up-Regulated | | | | Y | | | | | | ADP-ribosylation factor guanine nucleotide-exchange factor 1 (brefeldin A-inhibited) |
| 219918_s_at | ASPM | 4.16 | <0.01 | Up-Regulated | | | | | | | Y | Y | | asp (abnormal spindle)-like, microcephaly associated (*Drosophila*) |
| 208079_s_at | AURKA | 2.98 | <0.01 | Up-Regulated | | | | | | | Y | Y | | serine/threonine kinase 6 |
| 202095_s_at | BIRC5 | 2.95 | <0.01 | Up-Regulated | | | | | Y | Y | Y | Y | | baculoviral IAP repeat-containing 5 (survivin) |
| 209642_at | BUB1 | 2.71 | <0.01 | Up-Regulated | | Y | | | Y | Y | Y | Y | Y | BUB1 budding uninhibited by benzimidazoles 1 homolog (yeast) |
| 203755_at | BUB1B | 3.05 | <0.01 | Up-Regulated | | Y | | | Y | | Y | Y | Y | BUB1 budding uninhibited by benzimidazoles 1 homolog beta (yeast) |
| 201457_x_at | BUB3 | 2.03 | <0.01 | Up-Regulated | | | | | Y | | Y | | | BUB3 budding uninhibited by benzimidazoles 3 homolog (yeast) |
| 223361_at | C6orf115 | 2.4 | <0.01 | Up-Regulated | | | | | | | | | | chromosome 6 open reading frame 115 |

TABLE 6-continued

Malignancy-risk gene list.

| Affy probe set id | Gene Symbol | Fold change | FDR | Regulation | DNA replication | Mitosis | Poola et al | Turashvili et al | Chanrion et al | Ma et al | van't Veer et al | Wang et al | Huang et al | Gene Title |
|---|---|---|---|---|---|---|---|---|---|---|---|---|---|---|
| 228323_at | CASC5 | 2.26 | <0.01 | Up-Regulated | | | | | | | | | | cancer susceptibility candidate 5 |
| 214710_s_at | CCNB1 | 4.03 | <0.01 | Up-Regulated | | Y | | | Y | | Y | Y | Y | cyclin B1 |
| 202705_at | CCNB2 | 2.35 | <0.01 | Up-Regulated | | Y | | Y | Y | | Y | Y | Y | cyclin B2 |
| 205034_at | CCNE2 | 3.99 | <0.01 | Up-Regulated | Y | | | | Y | Y | Y | Y | | cyclin E2 |
| 203213_at | CDC2 | 5.5 | <0.01 | Up-Regulated | | Y | | | Y | | Y | Y | Y | Cell division cycle 2, G1 to S and G2 to M |
| 203214_x_at | CDC2 | 2.89 | <0.01 | Up-Regulated | | Y | | | Y | | Y | | Y | cell division cycle 2, G1 to S and G2 to M |
| 210559_s_at | CDC2 | 4.14 | <0.01 | Up-Regulated | | Y | Y | | Y | | Y | | Y | cell division cycle 2, G1 to S and G2 to M |
| 202870_s_at | CDC20 | 3.34 | <0.01 | Up-Regulated | | Y | | | | | | Y | | CDC20 cell division cycle 20 homolog (S. cerevisiae) |
| 223307_at | CDCA3 | 2.24 | <0.01 | Up-Regulated | | Y | | Y | | | | | | cell division cycle associated 3 |
| 224753_at | CDCA5 | 2.21 | <0.01 | Up-Regulated | Y | | | | | | | | | cell division cycle associated 5 |
| 1555758_a_at | CDKN3 | 2.85 | <0.01 | Up-Regulated | | | | | Y | Y | Y | Y | Y | cyclin-dependent kinase inhibitor 3 (CDK2-associated dual specificity phosphatase) |
| 209714_s_at | CDKN3 | 2.97 | <0.01 | Up-Regulated | | | Y | | Y | Y | Y | Y | Y | cyclin-dependent kinase inhibitor 3 (CDK2-associated dual specificity phosphatase) |
| 204962_s_at | CENPA | 2.71 | <0.01 | Up-Regulated | | | | | Y | Y | Y | Y | Y | centromere protein A, 17 kDa |
| 207828_s_at | CENPF | 2.6 | <0.01 | Up-Regulated | | | | | Y | | Y | Y | Y | centromere protein F, 350/400ka (mitosin) |
| 222848_at | CENPK | 2.18 | <0.01 | Up-Regulated | | | | Y | | | | | | leucine zipper protein FKSG14 |
| 218542_at | CEP55 | 3.46 | <0.01 | Up-Regulated | | | Y | Y | | | Y | Y | | chromosome 10 open reading frame 3 |
| 218252_at | CKAP2 | 2.72 | <0.01 | Up-Regulated | | | Y | | Y | | | Y | | cytoskeleton associated protein 2 |
| 204170_s_at | CKS2 | 6.32 | <0.01 | Up-Regulated | | | | | Y | Y | | Y | | CDC28 protein kinase regulatory subunit 2 |
| 205538_at | CORO2A | 2.24 | <0.01 | Up-Regulated | | | | | | | | | | coronin, actin binding protein, 2A |
| 202613_at | CTPS | 2.04 | <0.01 | Up-Regulated | | Y | | | Y | | Y | | | CTP synthase |

TABLE 6-continued

Malignancy-risk gene list.

| Affy probe set id | Gene Symbol | Fold change | FDR | Regulation | DNA replication | Mitosis | Poola et al | Turashvili et al | Chanrion et al | Ma et al | van't Veer et al | Wang et al | Huang et al | Gene Title |
|---|---|---|---|---|---|---|---|---|---|---|---|---|---|---|
| 222958_s_at | DEPDC1 | 2.4 | <0.01 | Up-Regulated | | | | | | | Y | | | DEP domain containing 1 |
| 218726_at | DKFZp762E1312 | 2 | <0.01 | Up-Regulated | | Y | | Y | | | Y | | | hypothetical protein DKFZp762E1312 |
| 203764_at | DLG7 | 2.84 | <0.01 | Up-Regulated | | Y | | | | | Y | Y | | discs, large homolog 7 (Drosophila) |
| 221677_s_at | DONSON | 2.42 | <0.01 | Up-Regulated | Y | | | | Y | | | Y | | downstream neighbor of SON |
| 218567_x_at | DPP3 | 2.33 | <0.01 | Up-Regulated | | | | | Y | | | | | dipeptidylpeptidase 3 |
| 232510_s_at | DPP3 | 2.2 | <0.01 | Up-Regulated | | | | | Y | | | | | dipeptidylpeptidase 3 |
| 218585_s_at | DTL | 4.78 | <0.01 | Up-Regulated | | | | Y | | | Y | | | denticleless homolog (Drosophila) |
| 219787_s_at | ECT2 | 3.89 | <0.01 | Up-Regulated | | Y | | | | | | Y | | epithelial cell transforming sequence 2 oncogene |
| 203358_s_at | EZH2 | 2.69 | <0.01 | Up-Regulated | Y | | | | | | Y | | Y | enhancer of zeste homolog 2 (Drosophila) |
| 225687_at | FAM83D | 3.33 | <0.01 | Up-Regulated | | | | | | | | | | chromosome 20 open reading frame 129 |
| 213007_at | FANCI | 2.25 | <0.01 | Up-Regulated | | | | Y | | | | | | hypothetical protein FLJ10719 |
| 202580_x_at | FOXM1 | 2.37 | <0.01 | Up-Regulated | | Y | | | Y | | | Y | | forkhead box M1 |
| 206102_at | GINS1 | 3.27 | <0.01 | Up-Regulated | | | | | | | | Y | | DNA replication complex GINS protein PSF1 |
| 205436_s_at | H2AFX | 2.14 | <0.01 | Up-Regulated | | | | | Y | | | | | H2A histone family, member X |
| 200853_at | H2AFZ | 2.23 | <0.01 | Up-Regulated | | | | | Y | | Y | Y | | H2A histone family, member Z |
| 213911_s_at | H2AFZ | 2.21 | <0.01 | Up-Regulated | | | | | Y | | Y | Y | | H2A histone family, member Z |
| 208490_x_at | HIST1H2BF | 2.5 | <0.01 | Up-Regulated | | | | | | | | | | histone 1, H2bf |
| 203744_at | HMGB3 | 2.71 | <0.01 | Up-Regulated | | | | | | | Y | | | high-mobility group box 3 |
| 207165_at | HMMR | 3.05 | <0.01 | Up-Regulated | | | | | Y | | | Y | | hyaluronan-mediated motility receptor (RHAMM) |
| 217755_at | HN1 | 3.4 | <0.01 | Up-Regulated | | | | | Y | Y | Y | | | hematological and neurological expressed 1 |

TABLE 6-continued

Malignancy-risk gene list.

| Affty probe set id | Gene Symbol | Fold change | FDR | Regulation | DNA replication | Mitosis | Poola et al | Turashvili et al | Chanrion et al | Ma et al | van't Veer et al | Wang et al | Huang et al | Gene Title |
|---|---|---|---|---|---|---|---|---|---|---|---|---|---|---|
| 229538_s_at | IQGAP3 | 2.51 | <0.01 | Up-Regulated | | | | Y | | | | | | IQ motif containing GTPase activating protein 3 |
| 202503_s_at | KIAA0101 | 5.89 | <0.01 | Up-Regulated | | | | | | | Y | Y | Y | KIAA0101 |
| 204444_at | KIF11 | 3.22 | <0.01 | Up-Regulated | | Y | | | Y | | Y | Y | Y | kinesin family member 11 |
| 218755_at | KIF20A | 2.93 | <0.01 | Up-Regulated | | | | | | | Y | | | kinesin family member 20A |
| 204709_s_at | KIF23 | 2.14 | <0.01 | Up-Regulated | | Y | | | | | Y | Y | Y | kinesin family member 23 |
| 218355_at | KIF4A | 2.67 | <0.01 | Up-Regulated | | | | | Y | | Y | Y | | kinesin family member 4A |
| 211762_s_at | KPNA2 | 3.03 | <0.01 | Up-Regulated | | | Y | | | | Y | | Y | karyopherin alpha 2 (RAG cohort 1, importin alpha 1) /// karyopherin alpha 2 (RAG cohort 1, importin alpha 1) |
| 219061_s_at | LAGE3 | 2.29 | <0.01 | Up-Regulated | | | | | | | Y | | | DNA segment on chromosome X (unique) 9879 expressed sequence |
| 202779_s_at | LOC731049 /// UBE2S | 2.36 | <0.01 | Up-Regulated | | | | | | | Y | | | ubiquitin-conjugating enzyme E2S |
| 1554768_a_at | MAD2L1 | 2.29 | <0.01 | Up-Regulated | | Y | | | | | Y | | Y | MAD2 mitotic arrest deficient-like 1 (yeast) |
| 210058_at | MAPK13 | 2.01 | <0.01 | Up-Regulated | | Y | | | Y | | | | | mitogen-activated protein kinase 13 |
| 202107_s_at | MCM2 | 2.08 | <0.01 | Up-Regulated | Y | | | Y | Y | | | Y | | MCM2 minichromosome maintenance deficient 2, mitotin (S. cerevisiae) |
| 212141_at | MCM4 | 2.14 | <0.01 | Up-Regulated | Y | | | | Y | | | Y | | MCM4 minichromosome maintenance deficient 4 (S. cerevisiae) |
| 222036_s_at | MCM4 | 2.69 | <0.01 | Up-Regulated | Y | | | | Y | | | Y | | MCM4 minichromosome maintenance deficient 4 (S. cerevisiae) |
| 204825_at | MELK | 3.76 | <0.01 | Up-Regulated | | Y | Y | | | | Y | Y | | maternal embryonic leucine zipper kinase |

TABLE 6-continued

Malignancy-risk gene list.

| Affy probe set id | Gene Symbol | Fold change | FDR | Regulation | DNA replication | Mitosis | Poola et al | Turashvili et al | Chanrion et al | Ma et al | van't Veer et al | Wang et al | Huang et al | Gene Title |
|---|---|---|---|---|---|---|---|---|---|---|---|---|---|---|
| 218883_s_at | MLF1IP | 4.23 | <0.01 | Up-Regulated | Y | | Y | | | | | | | MLF1 interacting protein |
| 201298_s_at | MOBK1B | 2.1 | <0.01 | Up-Regulated | | | | | | | | Y | | MOB1, Mps One Binder kinase activator-like 1B (yeast) |
| 217919_s_at | MRPL42 | 2.03 | <0.01 | Up-Regulated | | | | | Y | | | | | mitochondrial ribosomal protein L42 |
| 218663_at | NCAPG | 2.11 | <0.01 | Up-Regulated | | | | | | | | Y | | chromosome condensation protein G |
| 209520_s_at | NCBP1 | 2.3 | <0.01 | Up-Regulated | | | | | Y | | | | | nuclear cap binding protein subunit 1, 80 kDa |
| 204162_at | NDC80 | 2.41 | <0.01 | Up-Regulated | | | | | | | Y | | | kinetochore associated 2 |
| 204641_at | NEK2 | 5.55 | <0.01 | Up-Regulated | | | | Y | | | Y | | Y | NIMA (never in mitosis gene a)-related kinase 2 |
| 201577_at | NME1 | 2.15 | <0.01 | Up-Regulated | | | | | Y | Y | | Y | Y | non-metastatic cells 1, protein (NM23A) expressed in |
| 212316_at | NUP210 | 2.23 | <0.01 | Up-Regulated | | | | | | | | | | nucleoporin 210 kDa |
| 218039_at | NUSAP1 | 6.41 | <0.01 | Up-Regulated | | Y | | Y | | | Y | Y | | nucleolar and spindle associated protein 1 |
| 219978_s_at | NUSAP1 | 5 | <0.01 | Up-Regulated | | Y | Y | | | | | Y | | nucleolar and spindle associated protein 1 |
| 203228_at | PAFAH1B3 | 2.68 | <0.01 | Up-Regulated | | | | | Y | Y | | Y | | platelet-activating factor acetylhydrolase, isoform Ib, gamma subunit 29 kDa |
| 219148_at | PBK | 3.06 | <0.01 | Up-Regulated | | Y | | | | | | Y | | PDZ binding kinase |
| 201202_at | PCNA | 2.45 | <0.01 | Up-Regulated | Y | | | | | | Y | Y | | proliferating cell nuclear antigen |
| 201490_s_at | PPIF | 2.4 | <0.01 | Up-Regulated | | | | | Y | | | | | peptidylprolyl isomerase F (cyclophilin F) |
| 218009_s_at | PRC1 | 3.72 | <0.01 | Up-Regulated | | | | | | Y | Y | Y | | protein regulator of cytokinesis 1 |
| 222077_s_at | RACGAP1 | 3.36 | <0.01 | Up-Regulated | | | | Y | Y | Y | Y | Y | | Rac GTPase activating protein 1 |

TABLE 6-continued

Malignancy-risk gene list.

| Affy probe set id | Gene Symbol | Fold change | FDR | Regulation | DNA replication | Mitosis | Poola et al | Turashvili et al | Chanrion et al | Ma et al | van't Veer et al | Wang et al | Huang et al | Gene Title |
|---|---|---|---|---|---|---|---|---|---|---|---|---|---|---|
| 204146_at | RAD51AP1 | 2.79 | <0.01 | Up-Regulated | Y | | | | | | | Y | | RAD51 associated protein 1 |
| 201890_at | RRM2 | 8.07 | <0.01 | Up-Regulated | Y | | | | | Y | Y | Y | | ribonucleotide reductase M2 polypeptide |
| 209773_s_at | RRM2 | 6.73 | <0.01 | Up-Regulated | Y | | Y | | | Y | Y | Y | | ribonucleotide reductase M2 polypeptide |
| 204240_s_at | SMC2 | 2.01 | <0.01 | Up-Regulated | Y | | Y | | | | | | | SMC2 structural maintenance of chromosomes 2-like 1 (yeast) |
| 201663_s_at | SMC4 | 2.44 | <0.01 | Up-Regulated | Y | | | | | Y | | Y | | SMC4 structural maintenance of chromosomes 4-like 1 (yeast) |
| 209875_s_at | SPP1 | 5.7 | <0.01 | Up-Regulated | | | | | Y | | | Y | | secreted phosphoprotein 1 (osteopontin, bone sialoprotein I, early T-lymphocyte activation 1) |
| 209218_at | SQLE | 3.25 | <0.01 | Up-Regulated | | | | Y | Y | Y | | | Y | squalene epoxidase |
| 203046_s_at | TIMELESS | 2.12 | <0.01 | Up-Regulated | | | | | Y | | | Y | | timeless homolog (Drosophila) |
| 1554408_a_at | TK1 | 2.72 | <0.01 | Up-Regulated | Y | | | | Y | Y | Y | Y | | thymidine kinase 1, soluble |
| 202338_at | TK1 | 2.86 | <0.01 | Up-Regulated | Y | | | | Y | Y | Y | Y | | thymidine kinase 1, soluble |
| 222642_s_at | TMEM33 | 2.01 | <0.01 | Up-Regulated | | | | | | | | | | transmembrane protein 33 |
| 201291_s_at | TOP2A | 7.56 | <0.01 | Up-Regulated | | Y | | | Y | Y | | Y | Y | topoisomerase (DNA) II alpha 170 kDa |
| 201292_at | TOP2A | 6.03 | <0.01 | Up-Regulated | | Y | | | Y | Y | | Y | Y | topoisomerase (DNA) II alpha 170 kDa |
| 210052_s_at | TPX2 | 3.73 | <0.01 | Up-Regulated | | Y | Y | | Y | | | | | TPX2, microtubule-associated, homolog (Xenopus laevis) |
| 204822_at | TTK | 3.27 | <0.01 | Up-Regulated | | Y | | | Y | | Y | | | TTK protein kinase |
| 1554696_s_at | TYMS | 2.05 | <0.01 | Up-Regulated | Y | | | | Y | | Y | Y | | thymidylate synthetase |

TABLE 6-continued

Malignancy-risk gene list.

| Affy probe set id | Gene Symbol | Fold change | FDR | Regulation | DNA replication | Mitosis | Poola et al | Turashvili et al | Chanrion et al | Ma et al | van't Veer et al | Wang et al | Huang et al | Gene Title |
|---|---|---|---|---|---|---|---|---|---|---|---|---|---|---|
| 202954_at | UBE2C | 3.26 | <0.01 | Up-Regulated | | | | | | | Y | | Y | ubiquitin-conjugating enzyme E2C |
| 223229_at | UBE2T | 4.99 | <0.01 | Up-Regulated | | | | Y | | | Y | | | ubiquitin-conjugating enzyme E2T (putative) |
| 225655_at | UHRF1 | 6.34 | <0.01 | Up-Regulated | | | | | | | Y | | | ubiquitin-like, containing PHD and RING finger domains, 1 |
| 222804_x_at | WDR32 | 2.04 | <0.01 | Up-Regulated | | | | Y | | | | | | WD repeat domain 32 |
| 225676_s_at | WDSOF1 | 2.26 | <0.01 | Up-Regulated | | | | | | | | | | WD repeats and SOF1 domain containing |
| 218349_s_at | ZWILCH | 2.11 | <0.01 | Up-Regulated | | | Y | | | | | | | Zwilch, kinetochore associated, homolog (Drosophila) |
| 204026_s_at | ZWINT | 4.46 | <0.01 | Up-Regulated | | | | Y | Y | | Y | Y | Y | ZW10 interactor |
| 228273_at | FLJ11029 | 3.77 | <0.01 | Up-Regulated | | | | | | | | | | Hypothetical protein FLJ11029 |
| 229490_s_at | IQGAP3 | 2.52 | <0.01 | Up-Regulated | | | | | | | | | | IQ motif containing GTPase activating protein 3 |
| 203002_at | AMOTL2 | 2.39 | <0.01 | Down-Regulated | | | | | | | | | | angiomotin like 2 |
| 212914_at | CBX7 | 2.61 | <0.01 | Down-Regulated | | | Y | | | | | | | chromobox homolog 7 |
| 228693_at | CCDC50 | 3.07 | <0.01 | Down-Regulated | | | | | | | | Y | | chromosome 3 open reading frame 6 |
| 213348_at | CDKN1C | 3.65 | <0.01 | Down-Regulated | | | | Y | Y | | | | Y | Cyclin-dependent kinase inhibitor 1C (p57, Kip2) |
| 224352_s_at | CFL2 | 2.42 | <0.01 | Down-Regulated | | | | Y | Y | | | | | cofilin 2 (muscle) /// cofilin 2 (muscle) |
| 209763_at | CHRDL1 | 8.05 | <0.01 | Down-Regulated | | | | | | | | | | chordin-like 1 |
| 204455_at | DST | 11.94 | <0.01 | Down-Regulated | | | | Y | | | | | | dystonin |
| 206101_at | ECM2 | 2.97 | <0.01 | Down-Regulated | | | | | Y | | | | | extracellular matrix protein 2, female organ and adipocyte specific |

TABLE 6-continued

Malignancy-risk gene list.

| Affy probe set id | Gene Symbol | Fold change | FDR | Regulation | DNA replication | Mitosis | Poola et al | Turashvili et al | Chanrion et al | Ma et al | van't Veer et al | Wang et al | Huang et al | Gene Title |
|---|---|---|---|---|---|---|---|---|---|---|---|---|---|---|
| 204363_at | F3 | 2.5 | <0.01 | Down-Regulated | | | | | | | | | Y | coagulation factor III (thromboplastin, tissue factor) |
| 209220_at | GPC3 | 3.87 | <0.01 | Down-Regulated | | | | Y | Y | | | | | glypican 3 |
| 204793_at | GPRASP1 | 3.04 | <0.01 | Down-Regulated | | | | | | | | | | G protein-coupled receptor associated sorting protein 1 |
| 209894_at | LEPR | 5.51 | <0.01 | Down-Regulated | | | | | Y | | Y | | | leptin receptor |
| 225956_at | LOC153222 | 2.22 | <0.01 | Down-Regulated | | Y | | | | | | | | adult retina protein |
| 209737_at | MAGI2 | 2.06 | <0.01 | Down-Regulated | | | | | | | | | | membrane associated guanylate kinase, WW and PDZ domain containing 2 |
| 217546_at | MT1M | 3.14 | <0.01 | Down-Regulated | | | | Y | | | | | | metallothionein 1M |
| 209493_at | PDZD2 | 2.38 | <0.01 | Down-Regulated | | | | Y | | | | | | PDZ domain containing 3 |
| 238447_at | RBMS3 | 5.26 | <0.01 | Down-Regulated | | | | | | | Y | | | RNA binding motif, single stranded interacting protein |
| 222717_at | SDPR | 6.01 | <0.01 | Down-Regulated | | | | | Y | | | | | serum deprivation response (phosphatidylserine binding protein) |
| 227662_at | SYNPO2 | 4.91 | <0.01 | Down-Regulated | | | | Y | | | | | | synaptopodin 2 |
| 225093_at | UTRN | 2.24 | <0.01 | Down-Regulated | | | | Y | Y | | | | | utrophin (homologous to dystrophin) |
| 235308_at | ZBTB20 | 2.89 | <0.01 | Down-Regulated | | | | Y | | | | | | zinc finger and BTB domain containing 20 |
| 213158_at | | 3.84 | <0.01 | Down-Regulated | | | | | | | | | | MRNA; cDNA DKFZp586B211 (from clone DKFZp586B211) |
| 226250_at | | 2.81 | <0.01 | Down-Regulated | | | | | | | | | | CDNA FLJ34585 fis, clone KIDNE2008758 |
| 226252_at | | 2.89 | <0.01 | Down-Regulated | | | | | | | | | | CDNA FLJ34585 fis, clone KIDNE2008758 |

TABLE 6-continued

Malignancy-risk gene list.

| Affy probe set id | Gene Symbol | Fold change | FDR | Regulation | DNA replication | Mitosis | Poola et al | Turashvili et al | Chanrion et al | Ma et al | van't Veer et al | Wang et al | Huang et al | Gene Title |
|---|---|---|---|---|---|---|---|---|---|---|---|---|---|---|
| 227082_at | | 3.51 | <0.01 | Down-Regulated | | | | | | | | | | MRNA; cDNA DKFZp586K1922 (from clone DKFZp586K1922) |
| 227121_at | | 2.55 | <0.01 | Down-Regulated | | | | | | | | | | MRNA; cDNA DKFZp586K1922 (from clone DKFZp586K1922) |
| 227646_at | EBF | 5.35 | <0.01 | Down-Regulated | | | | | | | | | | Early B-cell factor |
| 227719_at | | 2.21 | <0.01 | Down-Regulated | | | | | | | | | | CDNA FLJ37828 fis, clone BRSSN2006575 |
| 235556_at | | 2.18 | <0.01 | Down-Regulated | | | | | | | | | | Transcribed locus, weakly similar to NP_703324.1 glutamic acid-rich protein (garp) [*Plasmodium falciparum* 3D7] |
| 235570_at | RBMS3 | 4.02 | <0.01 | Down-Regulated | | | | | | | | | | RNA binding motif, single stranded interacting protein |
| 243584_at | | 3.93 | <0.01 | Down-Regulated | | | | | | | | | | Transcribed locus, weakly similar to NP_060190.1 signal-transducing adaptor protein-2; brk kinase substrate [*Homo sapiens*] |

TABLE 7

A subset of malignancy-risk genes associated with DNA replication, mitosis, cancer risk, disease relapse/progression, and metastasis*.

| Affy probe set id | Gene Symbol | Fold change | FDR | Regulation | DNA replication | Mitosis | Poola et al | Turashvili et al | Chanrion et al | Ma et al | van't Veer et al | Wang et al | Huang et al | Gene Title |
|---|---|---|---|---|---|---|---|---|---|---|---|---|---|---|
| 222608_s_at | ANLN | 4.01 | <0.01 | Up-Regulated | | Y | | | Y | Y | Y | | | anillin, actin binding protein (scraps homolog, *Drosophila*) |
| 202095_s_at | BIRC5 | 2.95 | <0.01 | Up-Regulated | | Y | | | Y | Y | Y | Y | | baculoviral IAP repeat-containing 5 (survivin) |
| 209642_at | BUB1 | 2.71 | <0.01 | Up-Regulated | | Y | | | Y | Y | Y | Y | Y | BUB1 budding uninhibited by benzimidazoles 1 homolog (yeast) |
| 203755_at | BUB1B | 3.05 | <0.01 | Up-Regulated | | Y | | | Y | | Y | Y | Y | BUB1 budding uninhibited by benzimidazoles 1 homolog beta (yeast) |
| 214710_s_at | CCNB1 | 4.03 | <0.01 | Up-Regulated | | Y | | | Y | | | Y | Y | cyclin B1 |
| 202705_at | CCNB2 | 2.35 | <0.01 | Up-Regulated | | Y | | Y | Y | | Y | Y | Y | cyclin B2 |
| 205034_at | CCNE2 | 3.99 | <0.01 | Up-Regulated | Y | | | | Y | Y | Y | Y | | cyclin E2 |
| 203213_at | CDC2 | 5.5 | <0.01 | Up-Regulated | | Y | | | Y | | Y | Y | Y | Cell division cycle 2, G1 to S and G2 to M |
| 203214_x_at | CDC2 | 2.89 | <0.01 | Up-Regulated | | Y | | | Y | | Y | Y | Y | cell division cycle 2, G1 to S and G2 to M |
| 210559_s_at | CDC2 | 4.14 | <0.01 | Up-Regulated | | Y | Y | | Y | | Y | Y | Y | cell division cycle 2, G1 to S and G2 to M |
| 1555758_a_at | CDKN3 | 2.85 | <0.01 | Up-Regulated | | | | | Y | Y | Y | Y | Y | cyclin-dependent kinase inhibitor 3 (CDK2-associated dual specificity phosphatase) |
| 209714_s_at | CDKN3 | 2.97 | <0.01 | Up-Regulated | | | Y | | Y | Y | Y | Y | Y | cyclin-dependent kinase inhibitor 3 (CDK2-associated dual specificity phosphatase) |
| 204962_s_at | CENPA | 2.71 | <0.01 | Up-Regulated | | | | | | | | | | |
| 207828_s_at | CENPF | 2.6 | <0.01 | Up-Regulated | | | | | | | | | | |
| 218542_at | CEP55 | 3.46 | <0.01 | Up-Regulated | | | Y | Y | | | | | | |
| 218252_at | CKAP2 | 2.72 | <0.01 | Up-Regulated | | Y | Y | | | | | | | |
| 203764_at | DLG7 | 2.84 | <0.01 | Up-Regulated | | Y | Y | | | | | | | |
| 203358_s_at | EZH2 | 2.69 | <0.01 | Up-Regulated | Y | | | | | | | | | |
| 213911_s_at | H2AFZ | 2.21 | <0.01 | Up-Regulated | | | Y | | | | | | | |
| 202503_s_at | KIAA0101 | 5.89 | <0.01 | Up-Regulated | | | | | | | | | | |
| 204709_s_at | KIF23 | 2.14 | <0.01 | Up-Regulated | | Y | | | | | | | | |
| 202107_s_at | MCM2 | 2.08 | <0.01 | Up-Regulated | Y | | | Y | | | | | | |
| 204825_at | MELK | 3.76 | <0.01 | Up-Regulated | | Y | Y | | | | | | | |
| 204641_at | NEK2 | 5.55 | <0.01 | Up-Regulated | | | | Y | | | | | | |
| 201577_at | NME1 | 2.15 | <0.01 | Up-Regulated | | | | | | | | | | |
| 218039_at | NUSAP1 | 6.41 | <0.01 | Up-Regulated | | Y | | Y | | | | | | |
| 219978_s_at | NUSAP1 | 5 | <0.01 | Up-Regulated | | Y | Y | | | | | | | |
| 222077_s_at | RACGAP1 | 3.36 | <0.01 | Up-Regulated | | | | Y | | | | | | |
| 201890_at | RRM2 | 8.07 | <0.01 | Up-Regulated | Y | | | | | | | | | |
| 209773_s_at | RRM2 | 6.73 | <0.01 | Up-Regulated | Y | | Y | | | | | | | |
| 209218_at | SQLE | 3.25 | <0.01 | Up-Regulated | | | | Y | | | | | | |
| 1554408_a_at | TK1 | 2.72 | <0.01 | Up-Regulated | Y | | | | | | | | | |
| 202338_at | TK1 | 2.86 | <0.01 | Up-Regulated | Y | | | | | | | | | |
| 201291_s_at | TOP2A | 7.56 | <0.01 | Up-Regulated | | Y | | | | | | | | |
| 201292_at | TOP2A | 6.03 | <0.01 | Up-Regulated | | Y | | | | | | | | |
| 204822_at | TTK | 3.27 | <0.01 | Up-Regulated | | Y | | | | | | | | |
| 204026_s_at | ZWINT | 4.46 | <0.01 | Up-Regulated | | | | | | | | | | |

TABLE 7-continued

A subset of malignancy-risk genes associated with DNA replication, mitosis, cancer risk, disease relapse/progression, and metastasis*.

| Probe set | | | | | | Description |
|---|---|---|---|---|---|---|
| 204962_s_at | Y | Y | Y | Y | Y | centromere protein A, 17 kDa |
| 207828_s_at | Y | | Y | Y | Y | centromere protein F, 350/400ka (mitosin) |
| 218542_at | | | Y | Y | | chromosome 10 open reading frame 3 |
| 218252_at | Y | | | Y | | cytoskeleton associated protein 2 |
| 203764_at | | | Y | Y | | discs, large homolog 7 (*Drosophila*) |
| 203358_s_at | | | Y | Y | Y | enhancer of zeste homolog 2 (*Drosophila*) |
| 213911_s_at | Y | | Y | Y | | H2A histone family, member Z |
| 202503_s_at | Y | | Y | Y | Y | KIAA0101 |
| 204709_s_at | | | Y | Y | Y | kinesin family member 23 |
| 202107_s_at | Y | | | Y | | MCM2 minichromosome maintenance deficient 2, mitotin (*S. cerevisiae*) |
| 204825_at | | | Y | Y | | maternal embryonic leucine zipper kinase |
| 204641_at | | | Y | Y | Y | NIMA (never in mitosis gene a)-related kinase 2 |
| 201577_at | Y | Y | | Y | Y | non-metastatic cells 1, protein (NM23A) expressed in |
| 218039_at | | | Y | Y | | nucleolar and spindle associated protein 1 |
| 219978_s_at | | | Y | Y | | nucleolar and spindle associated protein 1 |
| 222077_s_at | Y | Y | Y | Y | | Rac GTPase activating protein 1 |
| 201890_at | | | Y | Y | Y | ribonucleotide reductase M2 polypeptide |
| 209773_s_at | | | Y | Y | Y | ribonucleotide reductase M2 polypeptide |
| 209218_at | Y | Y | | Y | Y | squalene epoxidase |
| 1554408_a_at | Y | Y | Y | Y | | thymidine kinase 1, soluble |
| 202338_at | Y | Y | Y | Y | | thymidine kinase 1, soluble |
| 201291_s_at | Y | Y | | Y | Y | topoisomerase (DNA) II alpha 170 kDa |
| 201292_at | Y | Y | | Y | Y | topoisomerase (DNA) II alpha 170 kDa |
| 204822_at | Y | | Y | Y | | TTK protein kinase |
| 204026_s_at | Y | | Y | Y | Y | ZW10 interactor |

*"Y" symbol was used to indicate the association of each malignancy-risk gene with DNA replication, mitosis, cancer risk (Poola et al or Turashvili et al), cancer relapse/progression (Chanrion et al or Ma et al), or metastasis (van't Veer et al, Wang et al, or Huang et al).

TABLE 8

External evaluation for classification of normal and IDC tissues in Turashvili et al's study. Malignancy-risk genes with p value < 0.05

| Affy.probe.set.id | Gene Symbol | Regulation | P value |
|---|---|---|---|
| 216266_s_at | ARFGEF1 | Up-Regulated | 0.0318 |
| 202705_at | CCNB2 | Up-Regulated | 0.0398 |
| 223307_at | CDCA3 | Up-Regulated | 0.0210 |
| 213348_at | CDKN1C | Down-Regulated | 0.0306 |
| 222848_at | CENPK | Up-Regulated | 0.0223 |
| 218542_at | CEP55 | Up-Regulated | 0.0397 |
| 224352_s_at | CFL2 | Down-Regulated | 0.0301 |
| 218726_at | DKFZp762E1312 | Up-Regulated | 0.0391 |
| 204455_at | DST | Down-Regulated | 0.0455 |
| 218585_s_at | DTL | Up-Regulated | 0.0126 |
| 213007_at | FANCI | Up-Regulated | 0.0015 |
| 209220_at | GPC3 | Down-Regulated | 0.0272 |
| 229538_s_at | IQGAP3 | Up-Regulated | 0.0320 |
| 202107_at | MCM2 | Up-Regulated | 0.0185 |
| 217546_at | MT1M | Down-Regulated | 0.0439 |
| 204641_at | NEK2 | Up-Regulated | 0.0380 |
| 218039_at | NUSAP1 | Up-Regulated | 0.0243 |
| 209493_at | PDZD2 | Down-Regulated | 0.0356 |
| 222077_s_at | RACGAP1 | Up-Regulated | 0.0353 |
| 209218_at | SQLE | Up-Regulated | 0.0458 |
| 223229_at | UBE2T | Up-Regulated | 0.0478 |
| 225093_at | UTRN | Down-Regulated | 0.0269 |
| 222804_x_at | WDR32 | Up-Regulated | 0.0371 |
| 235308_at | ZBTB20 | Down-Regulated | 0.0081 |
| 228273_at | | Up-Regulated | 0.0243 |

TABLE 9

Summary table of analysis results on seven external datasets for the clinical association of the malignancy-risk gene signature.

| Dataset | Sample size (n) | Endpoint | Statistics method | Test statistics | p value |
|---|---|---|---|---|---|
| Cancer risk | | | | | |
| Turashvili et al.'s IDC study | 10 | IDC versus normal | random effect model | | p = 0.029 |
| Poola et al's ADH study | 8 | cancer (ADHC) versus no cancer (ADH) | logistic regression | OR = 1.4 (continuous risk score); OR = 9 (binary score) | p = 0.131 (cont.) and p = 0.178 (binary) |
| Cancer relapse/progression | | | | | |
| Chanrion et al's Tamoxifen-Treated Primary Breast Cancer | 155 | relapse of primary breast cancer | logistic regression | OR = 7.82 | <0.0001 |
| Ma et al's breast cancer study | 61 | disease status (ADH, DCIS, IDC) | correlation analysis | r = 0.50 (Pearson or Spearman) | <0.0001 |
| | | | logistic regression | OR (DCIS) = 2.28 (compared to ADH) | p = 0.016 |
| | | | logistic regression | OR (IDC) = 3.31 (compared to ADH) | p = 0.008 |
| Prognosis | | | | | |
| van't Veer et al's breast metastasis dataset | training = 78 test = 263 | time to metastasis | log-rank test | $X^2$ = 12.2 (training set); $X^2$ = 22.4 (test set) | p = 0.0005 (training); <0.0001 (test) |
| Wang et al's breast cancer relapse free survival study | 286 | metastasis-free survival | log-rank test | $X^2$ = 12.6 | p = 0.0004 |
| Huang et al's breast lymph node study | 37 | lynph node (pos vs. neg) | logistic regression | OR = 7.29 | p = 0.007 |

What is claimed is:

1. A method for treating invasive ductal carcinoma, ductal carcinoma in situ, lobular carcinoma in situ or invasive lobular carcinoma in a human patient, the method comprising:
   (a) staining a breast tissue sample from the patient;
   (b) Identifying and isolating a stained breast tissue comprising only histologically normal cells;
   (c) assaying the identified and isolated breast tissue comprising only histologically normal cells for mRNA levels of malignancy-risk genes comprising BIRC5, BUB1B, CCNB1, CCNB2, CDC20, CEP55 and PRC1 to obtain a first mRNA expression profile;
   (d) comparing the first mRNA expression profile to a control mRNA expression profile obtainable by analyzing mRNA levels of the malignancy-risk genes in normal breast tissue;
   (e) observing the first mRNA expression profile is at least 2-fold higher than the control mRNA expression profile obtained from normal breast tissue; and
   (f) treating the patient for invasive ductal carcinoma, ductal carcinoma in situ, lobular carcinoma in situ or invasive lobular carcinoma.

2. The method of claim 1 wherein the patient is suspected of having breast cancer or has had breast cancer.

3. The method of claim 1 wherein the patient has had or currently has atypical hyperplasia.

4. The method of claim 1 wherein the patient has had or currently has fibroadenoma.

5. The method of claim 1 wherein the breast cancer is invasive ductal carcinoma (IDC) or ductal carcinoma in situ (DCIS).

6. The method of claim 1 wherein the patient has had a surgical procedure to remove breast cancer, breast tumor, or breast lesion.

7. The method of claim 6 wherein the surgical procedure is a lumpectomy or a mastectomy.

8. The method of claim 7 wherein the patient has initiated chemotherapy treatment either before, or after the surgical procedure.

9. The method of claim 1 wherein the breast tissue sample is obtained ipsilaterally with the cancer, tumor, or lesion.

10. A method for treating the spread of invasive ductal carcinoma, ductal carcinoma in situ, lobular carcinoma in situ or invasive lobular carcinoma in a human patient, the method comprising:
   (a) staining a breast tissue sample from the patient;
   (b) Identifying and isolating a stained breast tissue comprising only histologically normal cells;
   (c) assaying the identified and isolated breast tissue sample comprising only histologically normal cells for mRNA levels of malignancy-risk genes comprising BIRC5, BUB1B, CCNB1, CCNB2, CDC20, CEP55 and PRC1 to obtain a first mRNA expression profile;
   (d) comparing the first mRNA expression profile to a control mRNA expression profile obtainable by analyzing mRNA levels of the malignancy-risk genes in normal breast tissue;
   (e) observing the first mRNA expression profile is at least 2-fold higher than the control mRNA expression profile obtained from normal breast tissue; and
   (f) treating the patient for the spread of invasive ductal carcinoma, ductal carcinoma in situ, lobular carcinoma in situ or invasive lobular carcinoma.

11. The method of claim 10 wherein the breast cancer is invasive ductal carcinoma (IDC) or ductal carcinoma in situ (DCIS).

12. The method of claim 10 wherein the spread of cancer is metastasis.

13. The method of claim 10 wherein the patient had had a surgical procedure to remove breast cancer.

14. The method of claim 13 wherein the surgical procedure is a lumpectomy or a mastectomy.

15. The method of claim 14 wherein the patient has initiated chemotherapy or radiation treatment before or after the surgical procedure.

16. The method of either claim 1 or 10 wherein the malignancy-risk genes further comprise one or more genes selected from ANLN, BUB1, BUB3, CDC2, CDKN3, CENPA, CENPF, CKS2, DPP3, DTL, FOXM1, HN1, KPNA2, MELK, MLF1IP, NDC80, NME, NUSAP1, PAFAH1B3, PBK, PCNA, RACGAP1, RRM2, SMC4, SQLE, TK1, TOP2A and TYMS.

17. The method of either claim 1 or 10 wherein the malignancy-risk genes further comprise one or more genes selected from the group consisting of APOB EC3B, C60rf115, CASC5, CORO2A, FAM83D, HIST1H2BF, MOBK1B, WDSOF1, IQGAP3, AMOTL2, CCDC50, CHRDL1, GPRASP1, MAGI2, RBMS3, SYNPO2, Affymetrix probe set id 213158_at, Affymetrix probe set id 226250_at, Affymetrix probe set id 226252_at, Affymetrix probe set id 227082_at, Affymetrix probe set id 227121_at, Affymetrix probe set id 227646_at, Affymetrix probe set id 227719_at, Affymetrix probe set id 235556_at, Affymetrix probe set id 235570_at, and Affymetrix probe set id 243584_at.

18. The method of either claim 1 or 10 wherein the malignancy-risk genes further comprise one or more genes selected from the genes in ANLN, BUB1, CCNE2, CDC2, CDKN3, CENPA, CENPF, CKAP2, DLG7, EZH2, H2AFZ, KIAA0101, KIF23, MCM2, MELK, NEK2, NME1, NUSAP1, RACGAP1, RRM2, SQLE, TK1, TOP2A, TTK and ZWINT.

19. The method of either claim 1 or 10 wherein the malignancy-risk genes further comprise one or more genes selected from the genes in ARFGEF1, CDCA3, CDKN1C, CENPK, CFL2, DKFZp762E1312, DST, DTL, FANCI, GPC3, IQGAP3, MCM2, MT1M, NEK2, NUSAP1, PDZD2, RACGAP1, SQLE, UBE2T, UTRN, WDR32, ZBTB20 and FLJ11029.

20. The method of either claim 1 or 10 wherein the malignancy-risk genes further comprise one or more genes selected from the genes in ANLN, AURKA, BUB1, BUB3, CCNE2, CDC2, CDKN3, CENPA, CENPF, CTPS, DEPDC1, DKFZp762E1312, DLG7, DTL, EZH2, H2AFZ, HMGB3, HN1, KIAA0101, KIF20A, KIF23, KIF4A, KNTC2, KPNA2, LAGE3, LEPR, MAD2L1, MELK, NEK2, NUSAP1, PAK3, PCNA, RACGAP1, RRM2, TK1, TTK, TYMS, UBE2S, UBE2T, UHRF1 and ZWINT.

21. The method of either claim 1 or 10 wherein the malignancy-risk genes further comprise one or more genes selected from the genes in ANLN, ARF1, ARF4, BUB1, BUB3, CCNE2, CDC2, CDKN1C, CDKN3, CENPA, CENPF, CFL2, CKAP2, CKS2, CTPS, DONSON, DPP3, ECM2, FOXM1, GPC3, H2AFX, H2AFZ, HMMR, HN1, KIAA0101, KIF4A, LEPR, MAPK13, MCM2, MCM4, MRPL42, NCPB1, NME1, PAFAH1B3, PPIF, RACGAP1, CDPR, SPP1, SQLE, TIMELESS, TK1, TOP2A, TTK, TYMS, UTRN and ZWINT.

22. The method of either claim 1 or 10 wherein the malignancy-risk genes further comprise one or more genes selected from the genes in BUB1, C20orf1, CBX7, CDC2, CDKN1C, CDKN3, CENPA, CENPF, DXS9879E, E2-EPF, EZH2, KIAA0101, KIF11, KIF23, KPNA2, MAD2L1, NEK2, NME1, SMC4L1, SQLE, STK6, TOP2A, UBE2C and ZWINT.

* * * * *